(12) United States Patent
Hayashi et al.

(10) Patent No.: US 7,700,623 B2
(45) Date of Patent: Apr. 20, 2010

(54) ARYLAMIDINE DERIVATIVE, SALT THEREOF, AND ANTIFUNGAL CONTAINING THESE

(75) Inventors: Kazuya Hayashi, Uozu (JP); Kazuto Kunitani, Kosugi (JP); Sayuri Uehara, Toyama (JP); Teiichi Morita, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 418 days.

(21) Appl. No.: 11/631,399

(22) PCT Filed: Jun. 28, 2005

(86) PCT No.: PCT/JP2005/011809

§ 371 (c)(1),
(2), (4) Date: Dec. 29, 2006

(87) PCT Pub. No.: WO2006/003881

PCT Pub. Date: Jan. 12, 2006

(65) Prior Publication Data

US 2008/0319016 A1  Dec. 25, 2008

(30) Foreign Application Priority Data

Jun. 30, 2004  (JP) .............................. 2004-193386

(51) Int. Cl.
*A61K 31/445* (2006.01)
*A01N 43/42* (2006.01)
*A61K 31/435* (2006.01)
*C07D 211/20* (2006.01)

(52) U.S. Cl. ........................ 514/317; 514/277; 514/318; 514/345; 544/336; 546/236; 546/193; 546/304; 546/290; 546/152

(58) Field of Classification Search ................. 514/317, 514/318, 252.1, 345, 357, 336; 544/336; 546/192, 193, 304, 290
See application file for complete search history.

(56) References Cited

FOREIGN PATENT DOCUMENTS

WO  03 074476  9/2003

OTHER PUBLICATIONS

Ando et al. Remington pharmaceutical sceinces, 20th edition, copyright 2000, pp. 704-712.*
U.S. Appl. No. 12/159,527, filed Jun. 27, 2008, Hayashi.
U.S. Appl. No. 12/443,750, filed Mar. 31, 2009, Nishikawa.

* cited by examiner

*Primary Examiner*—Ardin Marschel
*Assistant Examiner*—Savitha Rao
(74) *Attorney, Agent, or Firm*—Oblon, Spivak, McClelland, Maier & Neustadt, L.L.P.

(57) ABSTRACT

An arylamidine derivative represented by the general formula (wherein $R^1$ represents optionally protected or substituted amidino; and $R^2$ and $R^3$ are the same or different and each represents hydrogen or halogeno) or a salt of the derivative. The derivative and salt have potent activity against fungi including ones having tolerance to azole type drugs and further have high safety and excellent properties in a repeated dose toxicity test. They are hence useful as an excellent antifungal.

3 Claims, 1 Drawing Sheet

ARYLAMIDINE DERIVATIVE, SALT THEREOF, AND ANTIFUNGAL CONTAINING THESE

This application is a 371 of PCT/JP2005/011809 filed Jun. 28, 2005.

TECHNICAL FIELD

The present invention relates to a novel arylamidine derivative or a salt thereof having an antifungal activity, and an antifungal agent comprising the same as an active ingredient.

BACKGROUND ART

Serious deep mycosis such as invasive candidiasis often becomes a fatal disease. Originally, it has been considered that a principal protective mechanism on the side of a host organism to fungi such as candida would be nonspecific immunization by neutrophils. When this protective mechanism normally functions, there is little risk of becoming infected with fungi. However, in recent years, a risk of suffering from deep mycosis has been boosted because of the increased number of patients with underlying diseases decreasing the immunological function of an organism, such as malignant tumors and AIDS, frequent use of anticancer agents or immunosuppressive agents, heavy use of antibacterial antibiotics or steroid hormone, long-term use of central venous hyperalimentation or venous catheterization, and the like (Non-Patent Document 1).

There are only 6 agents, i.e., amphotericin B, flucytosine, miconazole, fluconazole, itraconazole, and micafungin as agents for such deep mycosis. Amphotericin B has an extremely strong fungicidal action; however, it has a problem regarding side effects such as nephrotoxicity, and its clinical use is therefore limited. Flucytosine is rarely used alone at present because the agent has problems, e.g., development of resistance. Micafungin has a low activity against the genus *Cryptococcus*. The other agents are generically called an azole antifungal agent, and are most frequently used at present considering a balance between effectiveness and safety although their antifungal action tends to be generally inferior compared to that of amphotericin B (Non-Patent Document 2).

Currently, fluconazole-resistant *Candida albicans* (*C. albicans*) has been detected with a high frequency in oropharyngeal candidiasis lesions of AIDS patients to whom fluconazole has been repeatedly administered. What is more, most of the resistant strains show cross resistance to itraconazole and other azole agents. Further, such resistant strains have also been reported to be isolated from non-AIDS patients who developed chronic mucocutaneous candidiasis or deep candidiasis (Non-Patent Document 3). The problems regarding resistance seriously affect the management of patients with deep mycosis, the number of which has been steadily increasing (Non-Patent Document 3).

[Non-patent document 1]: Rinsho to Biseibutsu (Clinics and Microorganisms), Vol. 17: pp. 265-266, 1990

[Non-patent document 2]: Rinsho to Biseibutsu (Clinics and Microorganisms), Vol. 21: pp. 277-283, 1994

[Non-patent document 3]: Rinsho to Biseibutsu (Clinics and Microorganisms), Vol. 28: pp. 51-58, 2001

DISCLOSURE OF THE INVENTION

Problems to be Solved by the Invention

There is strongly desired an antifungal agent whose action mechanism differs from those of the existing agents and which is effective even against fungi resistant to azole agents while having reduced side effects. WO03/074476 describes that an arylamidine derivative has strong antifungal activities and is useful as an antifungal agent; however, there is a need for a compound having more reduced side effects and improved in physical properties such as hygroscopicity and deliquescence, and, in addition, a compound also having an excellent effect against protozoans and the like.

Means for Solving the Problems

As a result of intensive studies under such circumstances, the present inventors have found that a compound represented by general formula (1):

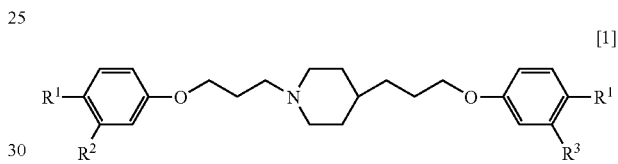

[1]

wherein $R^1$ represents an optionally protected or substituted amidino group; and $R^2$ and $R^3$ are identical or different and each represent a hydrogen atom or a halogen atom; or a salt thereof is effective even against fungi resistant to azole agents while having reduced side effects; particularly, a compound of general formula (1) wherein $R^1$ is an amidino group and $R^2$ and $R^3$ are each a hydrogen atom exhibits strong activities against fungi including those resistant to azole agents while having high safety; and, further, a trihydrochloride pentahydrate of a compound of general formula (1) wherein $R^1$ is an amidino group and $R^2$ and $R^3$ are each a hydrogen atom is excellent in chemical stability while having no deliquescence or hygroscopicity and suitable as a drug substance, and additionally has excellent activities against protozoans, thereby accomplishing the invention.

Advantages of the Invention

The compound of the invention is highly active against fungi including those resistant to azole agents, has excellent physical properties along with high safety, and is useful as an antifungal agent. In addition, the compound has excellent activities against protozoans and is useful as an antiprotozoan.

BEST MODE FOR CARRYING OUT THE INVENTION

The present invention is described below in detail.
In the description, unless otherwise noted, a halogen atom refers to a fluorine atom, a chlorine atom, a bromine atom, or an iodine atom; an alkyl group, for example, to a straight-chain or branched $C_{1-12}$ alkyl group such as methyl, ethyl, propyl, isopropyl, butyl, sec-butyl, isobutyl, tert-butyl, pentyl, isopentyl, hexyl, heptyl, and octyl; a lower alkyl group, for example, to a straight-chain or branched $C_{1-6}$ alkyl group such as methyl, ethyl, propyl, isopropyl, butyl, sec-butyl, isobutyl, tert-butyl, pentyl, and isopentyl; an alkenyl group, for example, to a straight-chain or branched $C_{2-12}$ alkenyl group such as vinyl, allyl, propenyl, isopropenyl, butenyl, isobutenyl, pentenyl, hexenyl, heptenyl, and octenyl; an aryl group, for example, to a group such as phenyl and naphthyl; an aralkyl group, for example, to an ar-$C_{1-6}$-alkyl group such as benzyl, diphenylmethyl, trityl, phenethyl, and naphthylmethyl; an alkoxy group, for example, to a straight-chain or branched $C_{1-6}$ alkyloxy group such as methoxy, ethoxy, propoxy, isopropoxy, butoxy, isobutoxy, sec-butoxy, tert-butoxy, pentyloxy, and isopentyloxy; an aralkyloxy group, for example, to an ar-$C_{1-6}$-alkyloxy group such as benzyloxy, diphenylmethyloxy, trityloxy, phenethyloxy, and naphthylmethyloxy; an alkoxyalkyl group, for example, to a $C_{1-6}$-alkyloxy-$C_{1-6}$-alkyl group such as methoxymethyl and 1-ethoxyethyl; a cycloalkyloxy group, for example, to a $C_{3-8}$ cycloalkyloxy group such as cyclopropoxy, cyclobutoxy, cyclopentyloxy, and cyclohexyloxy; an aralkyloxyalkyl group, for example, to an ar-$C_{1-6}$-alkyloxy-$C_{1-6}$-alkyl group such as benzyloxymethyl and phenethyloxymethyl; an acyl group, for example, to a straight-chain or branched $C_{2-12}$ alkanoyl group such as formyl, acetyl, propionyl, and isovaleryl, an ar-$C_{1-6}$-alkylcarbonyl group such as benzylcarbonyl, an aroyl group such as benzoyl and naphthoyl, a heterocyclic carbonyl group such as nicotinoyl, thenoyl, pyrrolidinocarbonyl, and furoyl, a carboxy-$C_{1-6}$-alkylcarbonyl group such as 3-carboxypropanoyl and 4-carboxybutanoyl, a $C_{1-6}$-alkyloxycarbonyl-$C_{1-6}$-alkylcarbonyl group such as 3-(methoxycarbonyl)propanoyl and 4-(methoxycarbonyl)butanoyl, a succinyl group, a glutaryl group, a maleoyl group, a phthaloyl group, or a straight-chain or branched α-aminoalkanoyl group whose N-terminal is optionally protected, derived from an amino acid (including, for example, glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, or hydroxyproline); an alkyloxycarbonyl group, for example, to a straight-chain or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl, and tert-pentyloxycarbonyl; a cycloalkyloxycarbonyl group, for example, to a $C_{3-8}$ cycloalkyloxycarbonyl group such as cyclopentyloxycarbonyl and cyclohexyloxycarbonyl; an aralkyloxycarbonyl group, for example, an ar-$C_{1-6}$-alkyloxycarbonyl group such as benzyloxycarbonyl and phenethyloxycarbonyl; an aryloxycarbonyl group, for example, to a group such as phenyloxycarbonyl; an acyloxy group, for example, to a straight-chain or branched $C_{2-6}$ alkanoyloxy group such as acetyloxy and propionyloxy or an aroyloxy group such as benzoyloxy; an arylthio group, for example, to a group such as phenylthio; an alkanesulfonyl group, for example, to a $C_{1-6}$ alkanesulfonyl group such as methanesulfonyl, ethanesulfonyl, and propanesulfonyl; an arylsulfonyl group, for example, to a group such as benzenesulfonyl, toluenesulfonyl, and naphthalenesulfonyl; an alkanesulfonyloxy group, for example, to a $C_{1-6}$ alkanesulfonyloxy group such as methanesulfonyloxy and ethanesulfonyloxy; an arylsulfonyloxy group, for example, to a group such as benzenesulfonyloxy and toluenesulfonyloxy; an alkylthiocarbonyl group, for example, to a $C_{1-6}$ alkylthiocarbonyl group such as methylthiocarbonyl and ethylthiocarbonyl; a cycloalkylidene group, for example, to a group such as cyclopentylidene and cyclohexylidene; an aralkylidene group, for example, to a group such as benzylidene and naphthylmethylene; a dialkylaminoalkylidene group, for example, to a group such as N,N-dimethylaminomethylene and N,N-diethylaminomethylene; a diaralkylphosphoryl group, for example, to a group such as dibenzylphosphoryl; a diarylphosphoryl group, for example, to a group such as diphenylphosphoryl;

an oxygen-containing heterocyclic group, for example, to a group such as tetrahydrofuryl and tetrahydropyranyl; an oxygen-containing heterocyclic alkyl group, for example, to a group such as 5-methyl-2-oxo-2H-1,3-dioxol-4-ylmethyl; a sulfur-containing heterocyclic group, for example, to a group such as tetrahydrothiopyranyl; a heterocyclic oxycarbonyl group, for example, to a group such as 2-furfuryloxycarbonyl and 8-quinolyloxycarbonyl; a nitrogen-containing heterocyclic alkylidene group, for example, to a group such as 3-hydroxy-4-pyridylmethylene; and a substituted silyl group, for example, to a group such as trimethylsilyl, triethylsilyl, and tributylsilyl.

Each of the above-described groups may be further substituted with one or more groups selected from a halogen atom, an optionally protected amino group, an optionally protected hydroxyl group, a nitro group, a lower alkyl group, an alkenyl group, an alkoxy group, an aralkyloxy group, an aryl group, an acyl group, and an oxo group.

The amino-protecting groups encompass all of the conventional groups which can be used as protective groups for an amino group, and include, for example, an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group, a dialkylaminoalkylidene group, an aralkylidene group, a nitrogen-containing heterocyclic alkylidene group, a cycloalkylidene group, a diarylphosphoryl group, a diaralkylphosphoryl group, an oxygen-containing heterocyclic alkyl group, and a substituted silyl group.

The hydroxyl-protecting groups encompass all of the conventional groups which can be used as protective groups for a hydroxyl group, and include, for example, an acyl group, an alkyloxycarbonyl group, an aralkyloxycarbonyl group, a heterocyclic oxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkanesulfonyl group, an arylsulfonyl group, and a substituted silyl group.

The amidino-protecting groups encompass all of the conventional groups which can be used as protective groups for an amidino group, and include, for example, an acyl group, an alkyloxycarbonyl group, an aralkyloxycarbonyl group, an aryloxycarbonyl group, a cycloalkyloxycarbonyl group, an aralkyl group, an alkoxyalkyl group, an aralkyloxyalkyl group, an arylthio group, an alkanesulfonyl group, an arylsulfonyl group, a cycloalkyloxycarbonyl group, an alkylthiocarbonyl group, a dialkylaminoalkylidene group, an aralkylidene group, a nitrogen-containing heterocyclic alkylidene group, a cycloalkylidene group, an oxygen-containing heterocyclic alkyl group, and a substituted silyl group.

The substituents for an amidino group include, for example, a hydroxyl group optionally substituted with an acyl group, and optionally substituted alkoxy and aralkyloxy groups.

The leaving groups include, for example, a halogen atom, an alkanesulfonyloxy group, an arylsulfonyloxy group, and an acyloxy group.

The salts of a compound of formula (1) include, for example, salts with mineral acids such as hydrochloric acid, hydrobromic acid, phosphoric acid, and sulfuric acid; salts with organic carboxylic acids such as formic acid, acetic acid, trichloroacetic acid, L-lactic acid, L-tartaric acid, citric acid, succinic acid, maleic acid, fumaric acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Preferred salts of a compound of formula (1) include pharmacologically acceptable salts.

According to the invention, preferred compounds include the following compounds.

A compound wherein $R^1$ is an amidino group optionally substituted with a hydroxyl group optionally substituted with an acyl group is preferable; a compound wherein $R^1$ is an amidino group optionally substituted with a hydroxyl group is more preferable; and a compound wherein $R^1$ is an amidino group is still more preferable.

A compound wherein $R^2$ and $R^3$ are identical or different and each a hydrogen atom or a fluorine atom is preferable; and a compound wherein $R^2$ and $R^3$ are each a hydrogen atom is more preferable.

The compound wherein $R^1$ is an amidino group and $R^2$ and $R^3$ are each a hydrogen atom is preferably a salt with hydrochloric acid, phosphoric acid, sulfuric acid, acetic acid, L-lactic acid, or methanesulfonic acid, more preferably a salt with hydrochloric acid, phosphoric acid, or sulfuric acid, still more preferably a salt with hydrochloric acid.

The hydrochloride of the compound wherein $R^1$ is an amidino group and $R^2$ and $R^3$ are each a hydrogen atom is preferably a dihydrochloride or trihydrochloride, more preferably a trihydrochloride.

The trihydrochloride is preferably a monohydrate or pentahydrate thereof, more preferably a pentahydrate thereof.

A method for producing the compound of the invention is then described.

The compound of the invention is produced by combining methods known per se, and, for example, by production methods given in the following.

wherein $R^4$ represents a lower alkyl group; and $R^2$ and $R^3$ have the same meanings as described above.

The compound of general formula (1a) can be produced by reacting the compound of general formula (2) with the compound of general formula (4) to convert to the compound of general formula (3), followed by reacting the compound of general formula (3) with ammonia or an ammonium salt. This reaction may be conducted by a method described, for example, in WO96/16947 and J. Org. Chem., 64: 12-13, 1999, or by a method equivalent thereto.

This series of reactions will be now described in detail.

(1-1)

The compound of general formula (3) can be produced by reacting the compound of general formula (2) with the compound of general formula (4) in the presence of an acid.

The solvent used in this reaction is not particularly limited, provided that it does not adversely affect the reaction, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; sulfoxides such as dimethylsulfoxide; ketones such as acetone and 2-butanone; esters such as ethyl acetate; and carboxylic acids such as acetic acid. These may be used in the form of a mixture. The compound of general formula (4) may be also used as a solvent.

Example of the acid used in the reaction include hydrogen chloride, hydrogen bromide, perchloric acid, p-toluenesulfonic acid, and methanesulfonic acid, and the usage amount thereof is 1- to 200-fold moles, preferably 5- to 100-fold moles based on the compound of general formula (2).

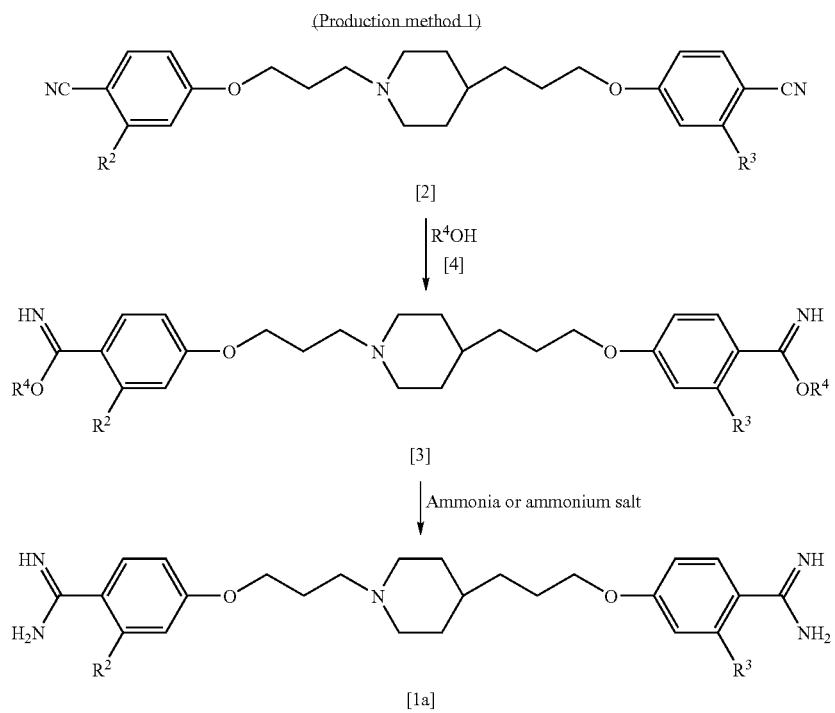

In the reaction, the usage amount of the compound of general formula (4) may be 2- to 1,000-fold moles based on the compound of general formula (2), and is preferably used as a solvent.

amount of ammonia or the ammonium salt may be 3- to 100-fold moles, preferably 3- to 10-fold moles based on the compound of general formula (3).

The reaction may be conducted at 0 to 150° C., preferably 20 to 120° C. for one minute to 24 hours.

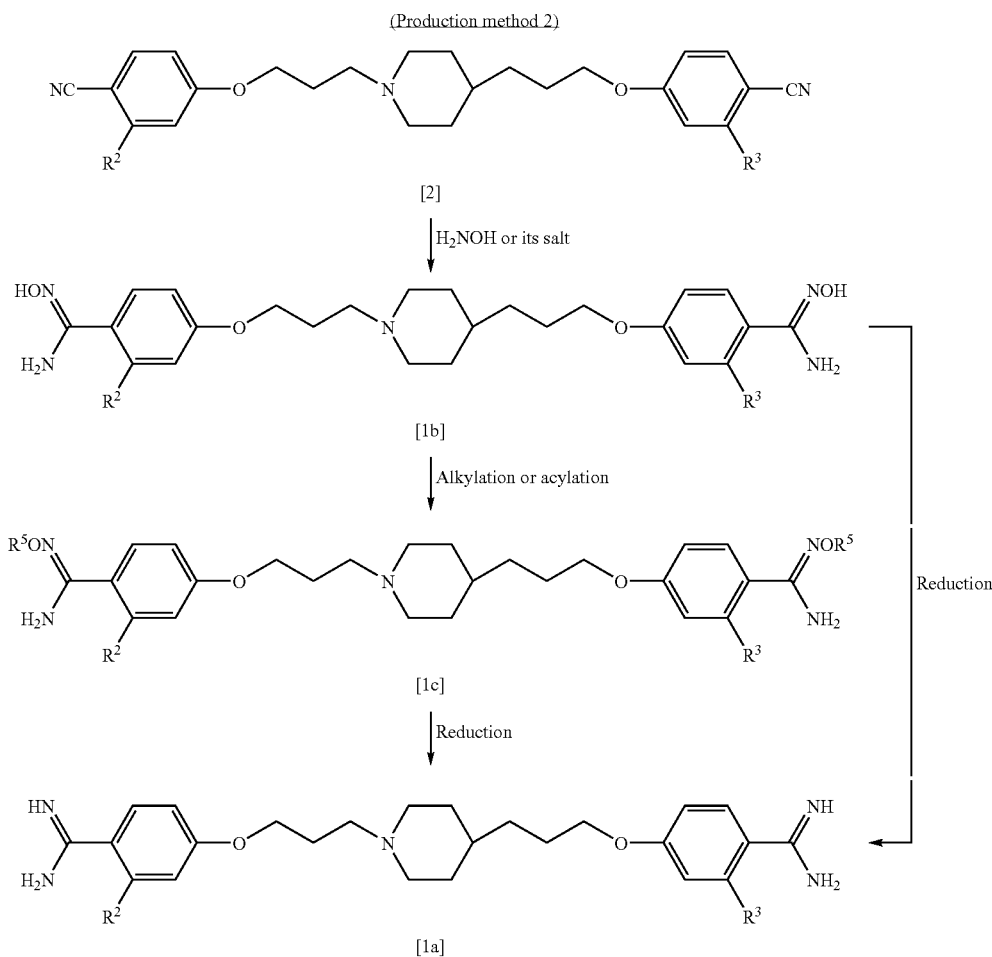

The reaction may be conducted at −30 to 150° C., preferably 10 to 50° C. for 30 minutes to 24 hours.

(1-2)

The compound of general formula (1a) can be produced by reacting the compound of general formula (3) with ammonia or an ammonium salt.

The solvent used in this reaction is not particularly limited, provided that it does not adversely affect the reaction, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; nitriles such as acetonitrile; sulfoxides such as dimethylsulfoxide; heteroaromatics such as pyridine; and water. These may be used in the form of a mixture Examples of the ammonium salt include ammonium chloride, ammonium bromide, and ammonium acetate. The usage wherein $R^5$ represents an optionally substituted acyl, lower alkyl or aralkyl group; and $R^2$ and $R^3$ have the same meanings as described above.

The compound of general formula (1b) can be produced from the compound of general formula (2). The compound of general formula (1b) can be then alkylated or acylated to produce the compound of general formula (1c). The compound of general formula (1c) can be further reduced to produce the compound of general formula (1a). In addition, the compound of general formula (1b) can be reduced to produce the compound of general formula (1a). These reactions may be conducted by methods described, for example, in Tetrahedron, 51: 12047-12068, 1995; Synthetic Communication, 26: 4351-4367, 1996; Synthesis, 16: 2467-2469, 2003;

Heterocycles, 60: 1133-1145, 2003; and Bioorganic and Medicinal Chemistry Letter, 12: 1203-1208, 2002, or by methods equivalent thereto.

This series of reactions will be now described in detail.

(2-1)

The compound of general formula (1b) can be produced by reacting the compound of general formula (2) with hydroxylamine or its salt in the presence or absence of a base.

The solvent used in this reaction is not particularly limited, provided that it does not adversely affect the reaction, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; sulfoxides such as dimethylsulfoxide; ketones such as acetone and 2-butanone; heteroaromatics such as pyridine; and water. These may be used in the form of a mixture.

Examples of the base used in the reaction, if desired, include metal alkoxides such as sodium methoxide, sodium ethoxide, potassium tert-butoxide, and sodium tert-butoxide; inorganic salts such as sodium hydroxide, potassium hydroxide, sodium hydrogencarbonate, sodium carbonate, potassium carbonate, sodium hydride, and potassium hydride; and organic bases such as triethylamine and pyridine.

The usage amount of the base may be 2- to 100-fold moles, preferably 2- to 20-fold moles based on the compound of general formula (2).

Examples of the salt of hydroxylamine include hydrochlorides and sulfates.

The usage amount of hydroxylamine or its salt may be 2- to 100-fold moles, preferably 2- to 20-fold moles based on the compound of general formula (2).

The reaction may be conducted at 0 to 150° C., preferably 50 to 150° C. for one minute to 24 hours.

(2-2)

The compound of general formula (1c) can be produced by reacting the compound of general formula (1b) with a reactive derivative or an alkylating agent in the presence or absence of a base.

The solvent used in this reaction is not particularly limited, provided that it does not adversely affect the reaction, and examples thereof include amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; nitriles such as acetonitrile; sulfoxides such as dimethylsulfoxide; ketones such as acetone and 2-butanone; esters such as ethyl acetate; carboxylic acids such as acetic acid; heteroaromatics such as pyridine; and water. These may be used in the form of a mixture.

Examples of the reactive derivative include acid anhydrides such as acetylformyloxide, acetic anhydride, trichloroacetic anhydride, and trifluoroacetic anhydride; mixed acid anhydrides of organic carboxylic acids such as acetic acid with carbonic acid monoalkyl esters such as ethyl chlorocarbonate and isobutyl chlorocarbonate; mixed acid anhydrides of organic carboxylic acids such as acetic acid with organic acids such as pivalic acid; acid chlorides such as acetyl chloride, trichloroacetyl chloride, and trifluoroacetyl chloride; acid bromides such as acetyl bromide; and active esters such as p-nitrophenyl ester, N-hydroxysuccinimide ester, and N-hydroxyphthalimide ester. These reactive derivatives may be used without isolation.

The reactive derivative may be generated in the system using a coupling agent. Examples of the coupling agent include carbodiimides such as N,N'-dicyclohexylcarbodiimide and N-ethyl-N'-(3-dimethylaminopropyl)carbodiimide; carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium=hexafluorophosphate; and O-(7-azabenzotriazol-1-yl)-1,1,3,3-tetramethyluronium=hexafluorophosphate.

Examples of the alkylating agent include halogenated alkyls such as methyl iodide and ethyl iodide; halogenated aralkyls such as benzyl chloride and benzyl bromide; and sulfates such as dimethyl sulfate.

Examples of the base used in the reaction, if desired, include metal alkoxides such as sodium methoxide, sodium ethoxide, potassium tert-butoxide, and sodium tert-butoxide; inorganic salts such as sodium hydroxide, potassium hydroxide, sodium bicarbonate, sodium carbonate, potassium carbonate, sodium hydride, and potassium hydride; and organic bases such as triethylamine and pyridine.

The usage amounts of the reactive derivative, alkylating agent and base may be each 2- to 100-fold moles, preferably 2- to 10-fold moles based on the compound of general formula (1b).

The reaction may be conducted at −20 to 100° C., preferably 0 to 50° C. for one minute to 24 hours.

(2-3)

The compound of general formula (1a) can be produced by subjecting the compound of general formula (1b) to reduction reaction. In addition, the compound of general formula (1a) can be produced by subjecting the compound of general formula (1c) to reduction reaction.

Examples of the reduction reaction used here include catalytic hydrogenation reaction employing a metal catalyst and reduction employing a metal and acid such as zinc-acetic acid.

When the compound of general formula (1b) or the compound of general formula (1c) is subjected to catalytic hydrogenation reaction, the solvent used is not particularly limited, provided that it does not adversely affect the reaction, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; nitriles such as acetonitrile; ketones such as acetone and 2-butanone; esters such as ethyl acetate; carboxylic acids such as acetic acid; heteroaromatics such as pyridine; and water. These may be used in the form of a mixture.

Examples of the metal catalyst include palladium catalysts such as palladium-carbon, palladium oxide, palladium hydroxide, and palladium black, nickel catalysts such as Raney nickel, and platinum oxide, and the usage amount thereof may be 0.001- to 1-fold (w/w), preferably 0.01- to 0.5-fold (w/w) that of the compound of general formula (1b) or the compound of general formula (1c).

Examples of reducing agents other than hydrogen include formic acid; formates such as sodium formate, ammonium formate, and triethylammonium formate; cyclohexene; and cyclohexadiene, and the usage amount thereof may be 2- to 100-fold moles, preferably 2- to 10-fold moles based on the compound of general formula (1b) or the compound of general formula (1c).

When the compound of general formula (1b) is subjected to catalytic hydrogenation reaction, the hydrogen pressure may be normal pressure to 30 atmospheric pressures, preferably 2 to 10 atmospheric pressures.

When the compound of general formula (1c) is subjected to catalytic hydrogenation reaction, the hydrogen pressure may be normal pressure.

The reaction may be conducted at 0 to 200° C., preferably 0 to 100° C. for one minute to 24 hours.

pound of general formula (1d) can be reduced to produce the compound of general formula (1a).

This series of reactions will be now described in detail.

(3-1)

The compound of general formula (1d) can be produced by reacting the compound of general formula (3) with the compound of general formula (5) or a salt thereof.

Examples of the compound of general formula (5) include O-methylhydroxylamine and O-benzylhydroxylamine.

Examples of the salt of the compound of general formula (5) include hydrochlorides and sulfates.

This reaction may be conducted according to production method (1-2).

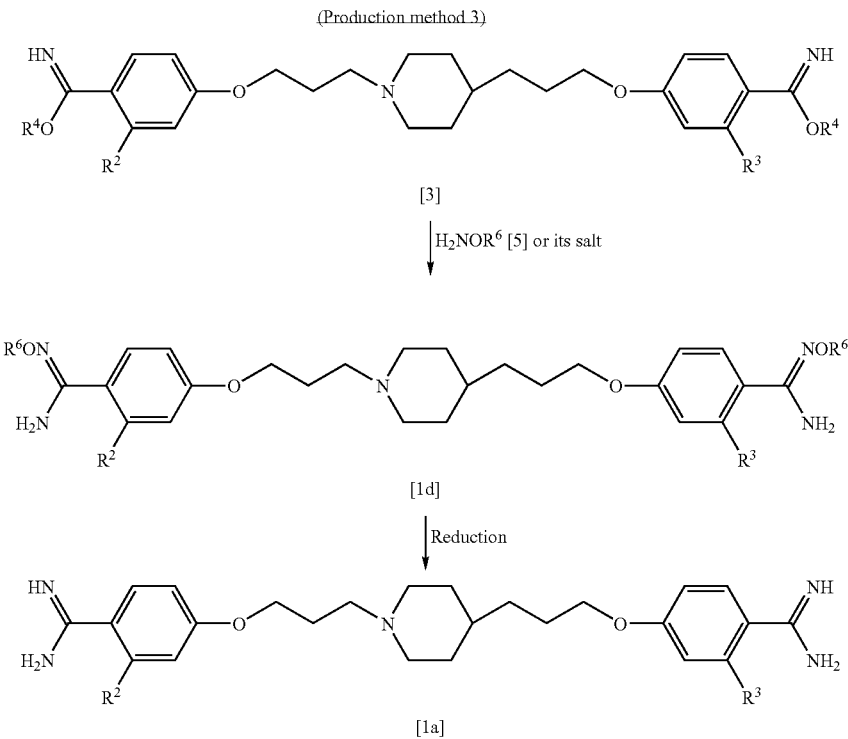

wherein $R^6$ represents an optionally substituted lower alkyl or aralkyl group; and $R^2$, $R^3$, and $R^4$ have the same meanings as described above.

The compound of general formula (1d) can be produced from the compound of general formula (3). Then, the com- (3-2)

The compound of general formula (1a) can be produced by reducing the compound of general formula (1d). This reaction may be conducted according to production method (2-3).

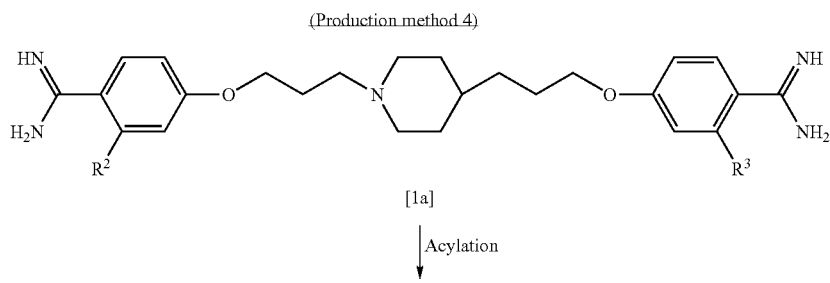

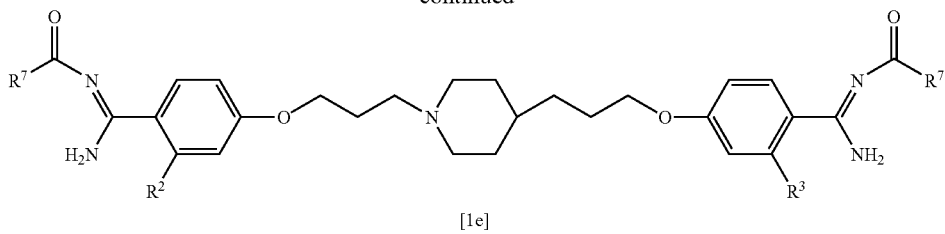

[1e]

wherein $R^7$ represents an optionally substituted lower alkyl, aralkyl, aryl, alkoxy, cycloalkyloxy or aralkyloxy group; $R^2$ and $R^3$ have the same meanings as described above.

The compound of general formula (1e) can be produced by reacting the compound of general formula (1a) with a reactive derivative in the presence or absence of a base.

This reaction may be conducted according to production method (2-2).

This series of reactions will be now described in detail.

(5-1)

The compound of general formula (7) can be produced by converting the hydroxyl group of the compound of general formula (6) to a leaving group.

When the leaving group is an alkanesulfonyloxy group or an arylsulfonyloxy group, the compound of general formula

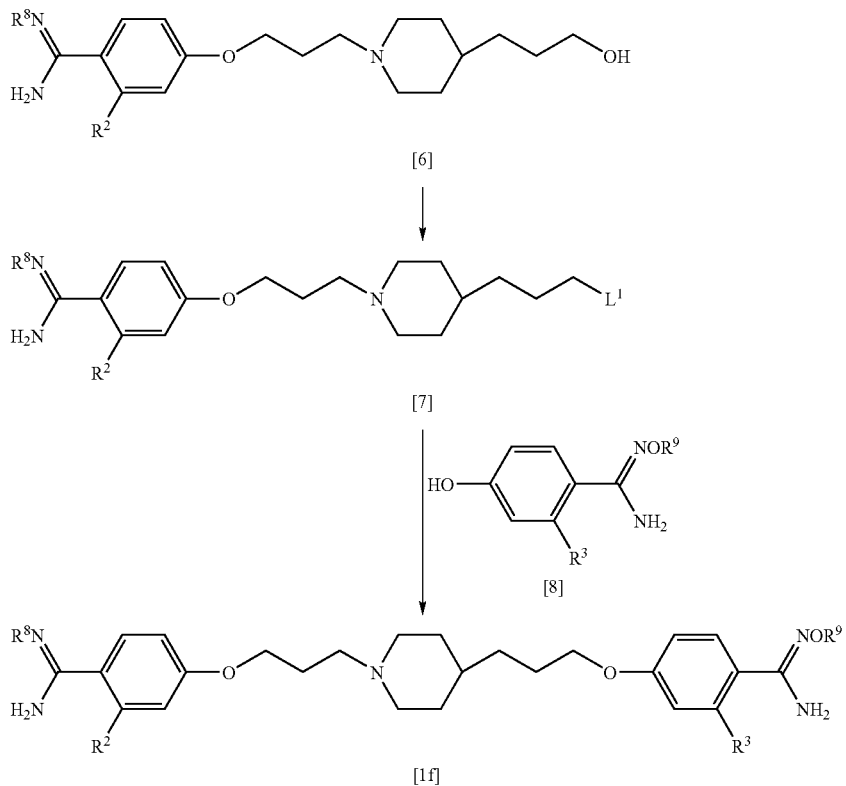

wherein $R^8$ represents an amidino-protecting group; $R^9$ represents a hydrogen atom or an optionally substituted lower alkyl or aralkyl group; $L^1$ represents a leaving group; and $R^2$ and $R^3$ have the same meanings as described above.

The compound of general formula (7) can be produced from the compound of general formula (6). The compound of general formula (7) can be then reacted with the compound of general formula (8) to produce the compound of general formula (1f).

(6) may be reacted in the presence or absence of a base, for example, with an alkanesulfonyl chloride such as methanesulfonyl chloride or an arylsulfonyl chloride such as p-toluenesulfonic acid chloride.

Examples of the base used in this reaction, if desired, include metal alkoxides such as sodium methoxide, sodium ethoxide, potassium tert-butoxide, and sodium tert-butoxide; inorganic bases such as sodium hydroxide, potassium hydroxide, sodium bicarbonate, sodium carbonate, potassium carbonate, sodium hydride, and potassium hydride; and organic bases such as triethylamine, N,N-diisopropylethylamine, and pyridine.

The usage amount of the alkanesulfonyl chloride or arylsulfonyl chloride may be 1- to 10-fold moles, preferably 1- to 3-fold moles based on the compound of general formula (6).

When the leaving group is a halogen atom, the compound of general formula (6) may be reacted, for example, with thionyl chloride, thionyl bromide, boron tribromide, or carbon tetrabromide-triphenylphosphine.

The usage amounts of these reagents may be each 1- to 10-fold moles, preferably 1- to 3-fold moles based on the compound of general formula (6).

The solvent used in this reaction is not particularly limited, provided that it does not adversely affect the reaction, and examples thereof include amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; nitriles such as acetonitrile; sulfoxides such as dimethylsulfoxide; and heteroaromatics such as pyridine. These may be used in the form of a mixture.

(5-2)

The compound of general formula (1f) can be produced by reacting the compound of general formula (7) with the compound of general formula (8) in the presence or absence of a base.

The solvent used in this reaction is not particularly limited, provided that it does not adversely affect the reaction, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; nitrites such as acetonitrile; sulfoxides such as dimethylsulfoxide; ketones such as acetone and 2-butanone; esters such as ethyl acetate; heteroaromatics such as pyridine; and water. These may be used in the form of a mixture.

Examples of the base used in this reaction, if desired, include metal alkoxides such as sodium methoxide, sodium ethoxide, potassium tert-butoxide, and sodium tert-butoxide; inorganic bases such as sodium hydroxide, potassium hydroxide, sodium bicarbonate, sodium carbonate, potassium carbonate, sodium hydride, and potassium hydride; and organic bases such as triethylamine, N,N-diisopropylethylamine, and pyridine.

The usage amount of the base may be 1- to 10-fold moles, preferably 1- to 3-fold moles based on the compound of general formula (7).

The usage amount of the compound of general formula (8) used in this reaction may be 1- to 20-fold moles, preferably 1- to 5-fold moles based on the compound of general formula (7).

The reaction may be conducted at 0 to 200° C., preferably 0 to 150° C. for one minute to 24 hours.

The removal of the amidino-protecting group represented by Re may be carried out by a method described, for example, in Protective Groups in Organic Synthesis, 3: 494-653, 1999, or by a method equivalent thereto.

(Production method 6)

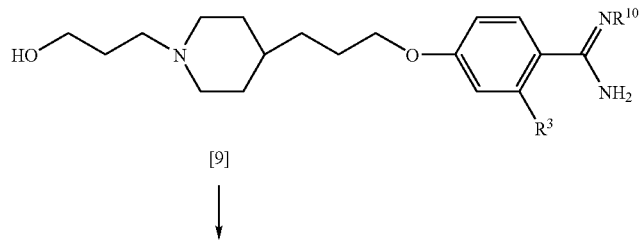

[9]

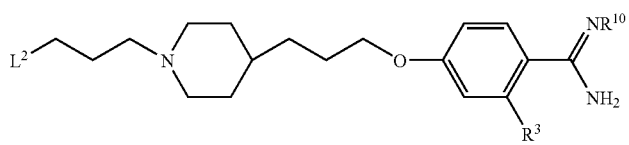

[10]

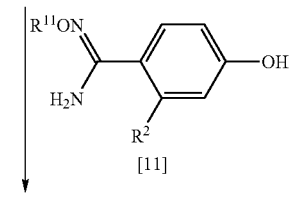

[11]

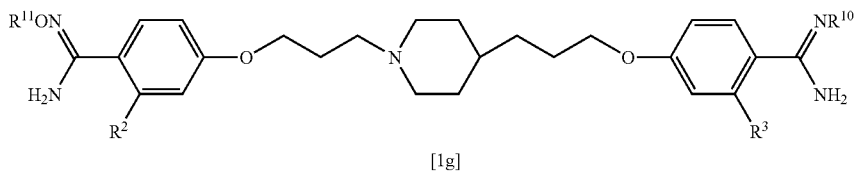

[1g]

wherein $R^{10}$ represents an amidino-protecting group; $R^{11}$ represents a hydrogen atom or an optionally substituted lower alkyl or aralkyl group; $L^2$ represents a leaving group; and $R^2$ and $R^3$ have the same meanings as described above.

The compound of general formula (10) can be produced from the compound of general formula (9). The compound of general formula (10) can be then reacted with the compound of general formula (11) to produce the compound of general formula (1g).

This series of reactions will be now described in detail.

(6-1)

The compound of general formula (10) can be produced by converting the hydroxyl group of the compound of general formula (9) to a leaving group.

This reaction may be conducted according to production method (5-1).

(6-2)

The compound of general formula (1g) can be produced by reacting the compound of general formula (10) with the compound of general formula (11) in the presence or absence of a base. This reaction may be conducted according to production method (5-2).

The removal of the amidino-protecting group represented by $R^{10}$ may be carried out by a method described, for example, in Protective Groups in Organic Synthesis, 3: 494-653, 1999, or by a method equivalent thereto.

Each of the compounds in the above-described production methods 1 to 6 may be also used in the form of a salt, and examples of the salt include the same salts as those described for the compound of general formula (1).

Each of the production intermediates obtained in the above-described production methods (1) to (6) may be also used without isolation for the subsequent reaction.

The compounds of general formulas (1a), (1b), (1c), (1d), (1e), (1f), and (1g) thus obtained or salts thereof can be derivatized into other compounds of general formula (1) or salts thereof, for example, by subjecting to a reaction known per se such as condensation, addition, oxidation, reduction, rearrangement, substitution, halogenation, dehydration, or hydrolysis, or by properly combining these reactions.

When isomers (e.g., optical isomer, geometrical isomer, and tautomer) are present in the compounds in the above-described production methods, these isomers may be also used, and solvates, hydrates, and crystals in various forms may be also employed.

In the following, description will be given of methods for producing compounds of general formulas (2), (6), (8), (9), and (11) as raw materials in the production of the compounds of the invention. The compounds of general formulas (2), (6), (8), (9), and (11) are produced by combining methods known per se, and, for example, can be prepared by the following production methods.

(Production method A)

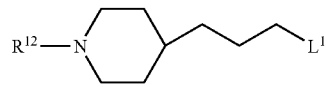

[12]

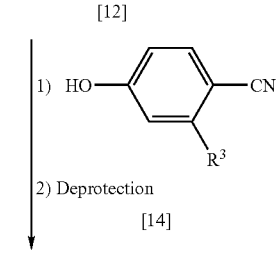

[14]

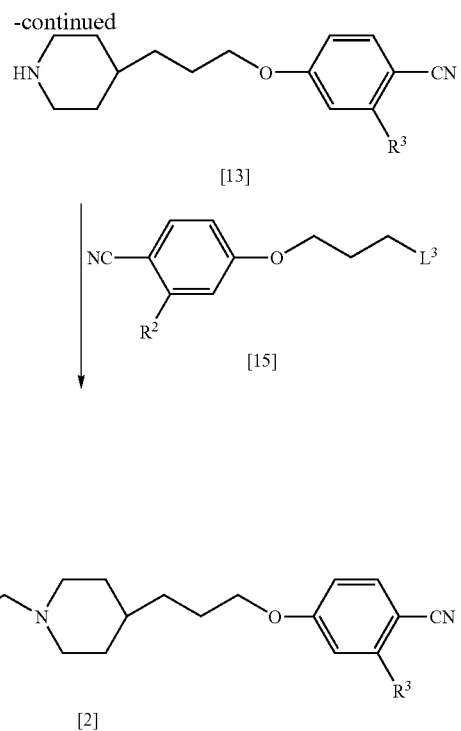

wherein $R^{12}$ represents an amino-protecting group; $L^3$ represents a leaving group; and $R^2$, $R^3$, and $L^1$ have the same meanings as described-above.

Examples of the compound of general formula (12) include benzyl=4-(3-bromopropyl)piperidine-1-carboxylate (J. Med. Chem., 46: 2606-2620, 2003), tert-butyl=4-(3-bromopropyl)-1-piperidinecarboxylate (Tetrahedron, 55: 11619-11639, 1999), and 3-[N-[(tert-butoxy)carbonyl]piperidin-4-yl]propyl iodide (J. Med. Chem., 37: 2537-2551, 1994). In addition, the synthesis can be carried out by combining known methods using tert-butyl=4-(3-hydroxypropyl)-1-piperidinecarboxylate or the like as a raw material.

Examples of the compound of general formula (14) include 4-cyanophenol and 4-cyano-3-fluorophenol.

(A-1)

The Compound of General Formula (13) can be produced by reacting the compound of general formula (12) with the compound of general formula (14) in the presence or absence of a base, followed by deprotection.

The solvent used in this reaction is not particularly limited, provided that it does not adversely affect the reaction, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, diethylene glycol dimethyl ether, diethylene glycol diethyl ether, and ethylene glycol monomethyl ether; nitrites such as acetonitrile; sulfoxides such as dimethylsulfoxide; ketones such as acetone and 2-butanone; esters such as ethyl acetate; heteroaromatics such as pyridine; and water. These may be used in the form of a mixture.

Examples of the base used in this reaction, if desired, include metal alkoxides such as sodium methoxide, sodium ethoxide, potassium tert-butoxide, and sodium tert-butoxide; inorganic bases such as sodium hydroxide, potassium hydroxide, sodium bicarbonate, sodium carbonate, potassium carbonate, sodium hydride, and potassium hydride; and organic bases such as triethylamine, N,N-diisopropylethylamine, and pyridine.

The usage amount of the base may be 1- to 10-fold moles, preferably 1- to 3-fold moles based on the compound of general formula (12).

The usage amount of the compound of general formula (14) used in this reaction may be 1- to 20-fold moles, preferably 1- to 5-fold moles based on the compound of general formula (12).

The reaction may be conducted at 0 to 200° C., preferably 0 to 150° C. for one minute to 24 hours.

The removal of the amino-protecting group represented by $R^{12}$ may be carried out by a method described, for example, in Protective Groups in Organic Synthesis, 3: 494-653, 1999, or by a method equivalent thereto.

(A-2)

The Compound of General Formula (2) can be produced by reacting the compound of general formula (13) with the compound of general formula (15). This reaction may be conducted according to production method (A-1).

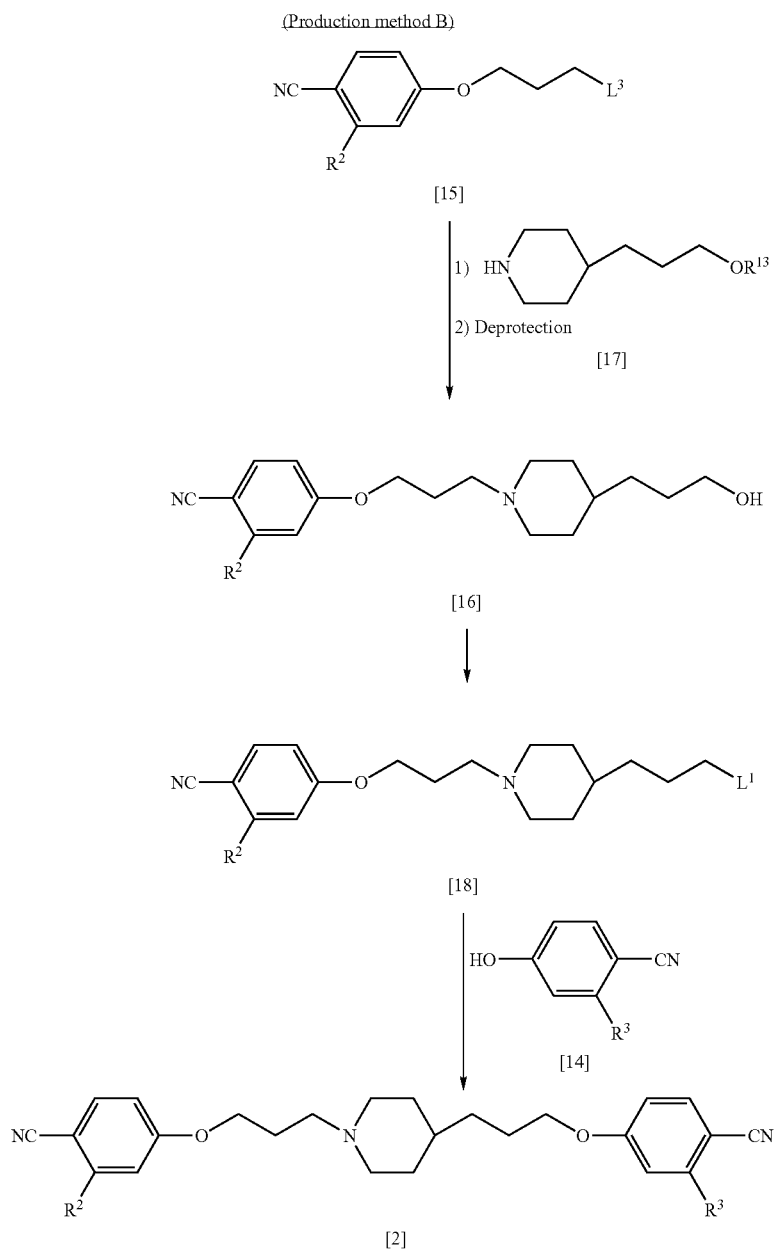

wherein $R^{13}$ represents a hydroxyl-protecting group; and $R^1$, $R^3$, $L^1$, and $L^3$ have the same meanings as described above.

The compound of general formula (17) can be produced by combining known methods, using tert-butyl=4-(3-hydroxypropyl)-1-piperidinecarboxylate or the like as a raw material.

(B-1)

The Compound of General Formula (16) can be produced by reacting the compound of general formula (15) with the compound of general formula (17), followed by deprotection. This reaction may be conducted according to production method (A-1).

The removal of the hydroxyl-protecting group represented by $R^{13}$ may be carried out by a method described, for example, in Protective Groups in Organic Synthesis, 3: 17-245, 1999, or by a method equivalent thereto.

(B-2)

The Compound of General Formula (18) can be produced by converting the hydroxyl group of the compound of general formula (16) to a leaving group.

This reaction may be conducted according to production method (5-1).

(B-3)

The Compound of General Formula (2) can be produced by reacting the compound of general formula (18) with the compound of general formula (14). This reaction may be conducted according to production method (A-1).

(Production method C)

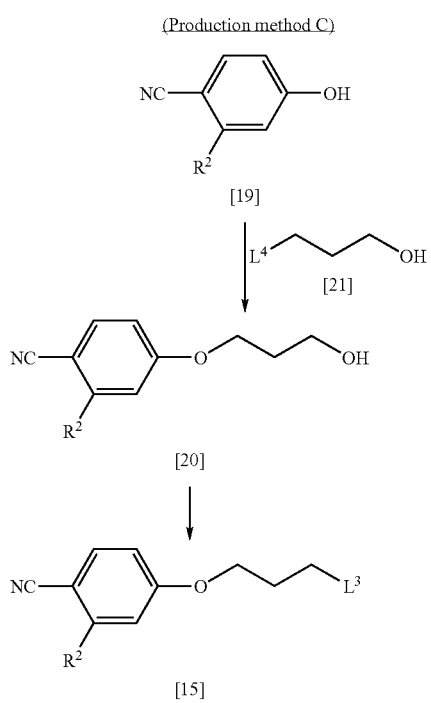

wherein $L^4$ represents a leaving group; and $R^2$ and $L^3$ have the same meanings as described above.

Examples of the compound of general formula (19) include 4-cyanophenol. Examples of the compound of general formula (21) include 3-bromo-1-propanol.

(C-1)

The compound of general formula (20) can be produced by reacting the compound of general formula (19) with the compound of general formula (21). This reaction may be conducted according to production method (A-1).

(C-2)

The compound of general formula (15) can be produced by converting the hydroxyl group of the compound of general formula (20) to a leaving group. This reaction may be conducted according to production method (5-1).

(Production method D)

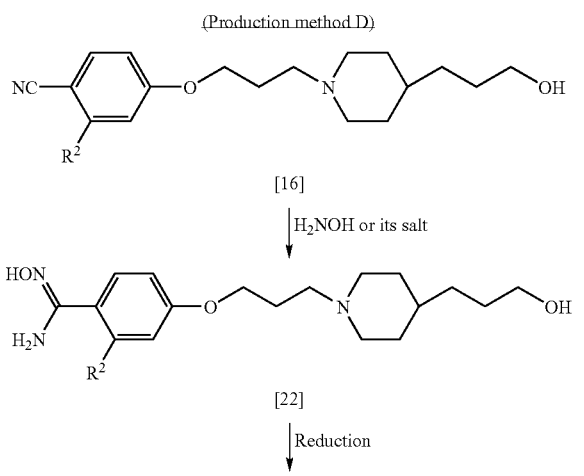

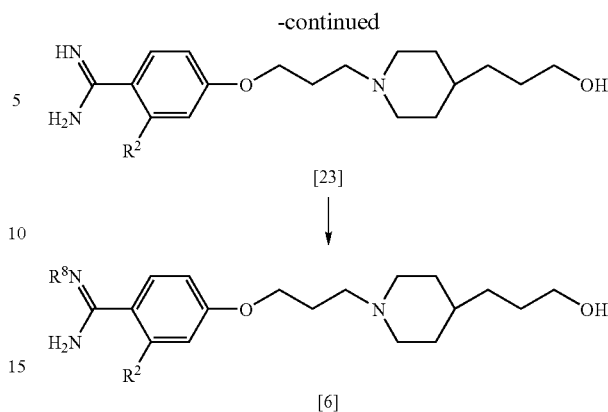

wherein $R^2$ and $R^8$ have the same meanings as described above.

(D-1)

The Compound of General Formula (22) can be produced by reacting the compound of general formula (16) with hydroxylamine or its salt in the presence or absence of a base. This reaction may be conducted according to production method (2-1).

(D-2)

The Compound of General Formula (23) can be produced by subjecting the compound of general formula (22) to reduction reaction. This reaction may be conducted according to production method (2-3).

(D-3)

The Compound of General Formula (6) can be produced by protecting the amidino group of the compound of general formula (23). This reaction may be carried out by a method described, for example, in Protective Groups in Organic Synthesis, 3: 494-653, 1999, or by a method equivalent thereto.

(Production method E)

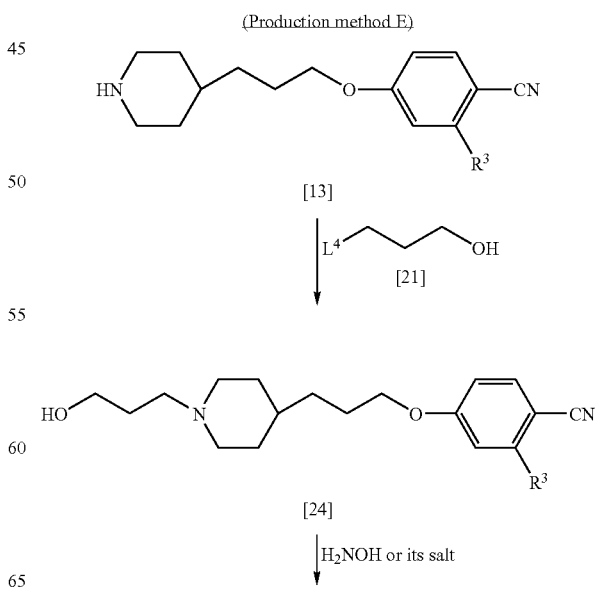

-continued

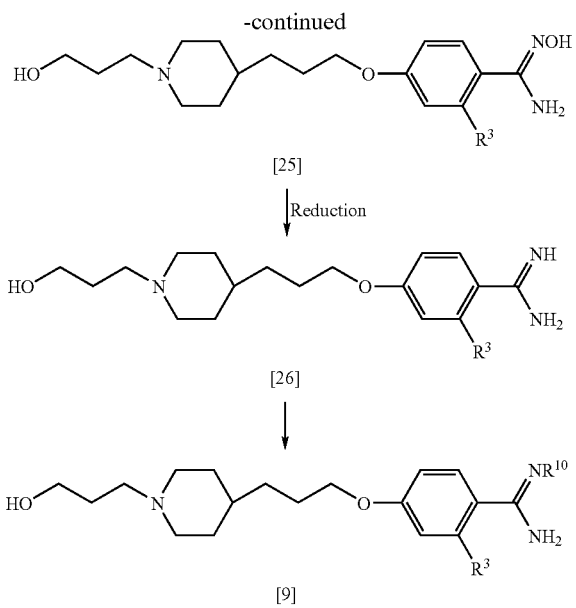

wherein $R^3$, $R^{10}$, and $L^4$ have the same meanings as described above.

(E-1)

The Compound of General Formula (24) can be produced by reacting the compound of general formula (13) with the compound of general formula (21). This reaction may be conducted according to production method (A-1).

(E-2)

The Compound of General Formula (25) can be produced by reacting the compound of general formula (24) with hydroxylamine or its salt in the presence or absence of a base. This reaction may be conducted according to production method (2-1).

(E-3)

The Compound of General Formula (26) can be produced by subjecting the compound of general formula (25) to reduction reaction. This reaction may be conducted according to production method (2-3).

(E-4)

The Compound of General Formula (9) can be produced by protecting the amidino group of the compound of general formula (26). This reaction may be conducted according to production method (D-3).

(Production method F)

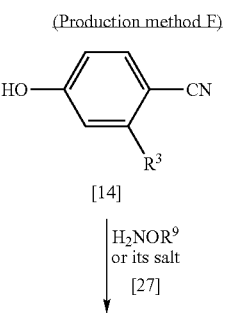

-continued

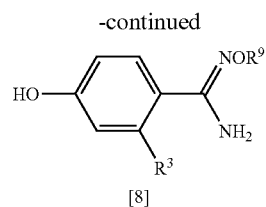

wherein $R^3$ and $R^9$ have the same meanings as described above.

The compound of general formula (8) can be produced by reacting the compound of general formula (14) with the compound of general formula (27) or a salt thereof. This reaction may be conducted according to production method (2-1).

(Production method G)

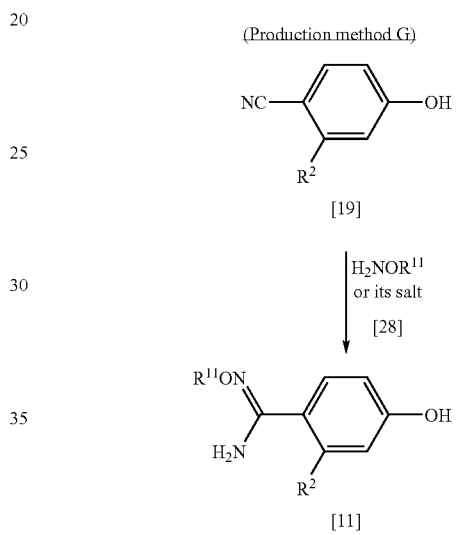

wherein $R^2$ and $R^{11}$ have the same meanings as described above.

The compound of general formula (11) can be produced by reacting the compound of general formula (19) with the compound of general formula (28) or a salt thereof. This reaction may be conducted according to production method (2-1).

When used as a medicine, the compound of the invention may generally be properly mixed with a pharmaceutical auxiliaries such as an excipient, a carrier, and a diluent, used for formulation, which can be orally or parenterally administered in the form of tablets, capsules, powders, syrups, granules, pills, suspensions, emulsions, solutions, powder preparations, suppositories, eye drops, nasal drops, ear drops, patches, ointments, or injections, according to the ordinary method. In addition, the administration method, dosage, and administration frequency can be properly selected depending on the age, body weight and symptoms of a patient. Typically, 0.01 to 1,000 mg/kg thereof may be administered orally or parenterally (e.g., by injection, drip infusion, or rectal administration) to an adult once or in several divided portions in a day.

To establish the usefulness of the compound of the invention, tests on the antifungal action, repeated toxicity, Vero cell proliferation inhibiting activity, stability, and antiprotozoan action thereof were carried out.

Test Example 1

Antifungal Action

The compound of Example 4 was selected as a compound of the invention. The compound described in the Example of WO03/074476, having a structure most analogous to that of the compound of the invention, was selected as a comparative compound. Their chemical structures are as follows.

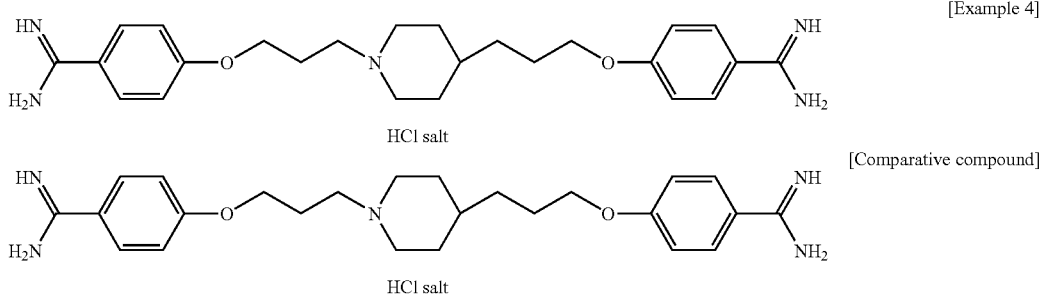

Susceptibility testing of fungi was carried out using a microbroth dilution method. The medium used in the susceptibility test was RPMI1640 (RPMI/MOPS) adjusted to pH 7.0 employing 0.165 mol/L morpholinepropanesulfonic acid (MOPS) and 1.0 mol/L sodium hydroxide. A test compound was dissolved in sterile water, which was then subjected to two-fold serial dilution using 100 μL of RPMI/MOPS on a 96-well round bottom plate. *Candida albicans* TIMM1623 cultured overnight at 35° C. on Sabouraud agar medium was suspended in a sterilized physiological saline. The number of cells was counted under a biological microscope; a suspension of inoculum organism $2 \times 10^3$ cells/mL) was prepared using RPMI/MOPS, and 100 μL thereof was then dispensed into each well; and a microplate containing a predetermined concentration of the test compound, the medium, and fungal cells was finally prepared. The plate was cultured at 35° C. for 48 hours. After the end of cultivation, absorbance was determined at 630 nm using an automatic spectrophotometer. The lowest test compound concentration at which 50% growth inhibition was observed as compared to growth control where no test compound was added was defined as $IC_{50}$. The results are shown in Table 1.

TABLE 1

| Compound | Example 4 | Comparative compound |
|---|---|---|
| $IC_{50}$ (μg/mL) | ≦0.0039 | 0.0039* |

*Value described in W003/074476

The compound of Example 4 had an equivalent or higher antifungal activity than the comparative compound.

Test Example 2

Repeated-Dose Toxicity Test in Mice (1)

The compound of Example 4 was selected as a compound of the invention. Among compounds described in the Examples of WO03/074476, a compound having a structure most analogous to that of the compound of the invention was selected as a comparative compound. Their chemical structures are as follows.

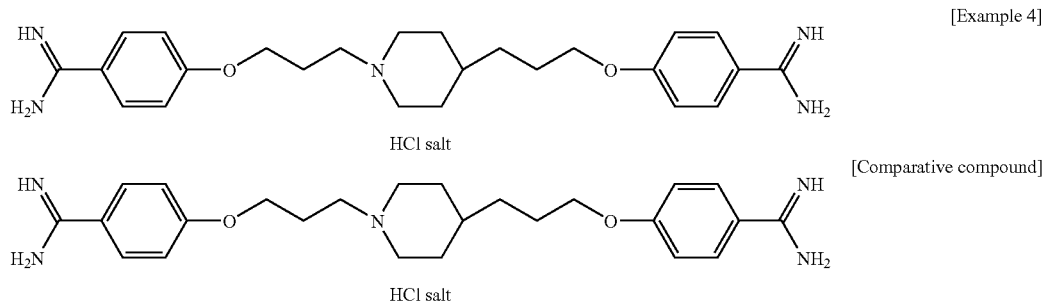

Six-week old male ICR mice (body weight range: 30.6 to 34.8 g, the number of animals allocated to each group: 5) were used to examine the repeated-dose toxicity. A solution of each test compound was prepared by dissolution in distilled water. Each compound was subcutaneously administered at a dose of 6.25 mg/kg once a day for 7 days. A sterilized physiological saline was administered to a control group. At the end of the administration period, each mouse was anesthetized with ether. An injection syringe containing a heparin solution (Novo-Heparin Injection 1000, Aventis Pharma K.K.) as an anticoagulant was used for blood collection from abdominal portion of the vena cava. A hematological test was carried out for the following items. Values in the test compound-treated groups when a value in the control group is set to 100 are shown in Table 2.

(Hematological Test Items and Determination Methods)

Red blood cell count (RBC): Two-angle laser flow cytometry

Reticulocyte count: Flow cytometry after RNA staining

TABLE 2

| Compound | Example 4 | Comparative compound |
| --- | --- | --- |
| Red blood cell count (RBC) | 94 | 105 |
| Reticulocyte count (Reticulocyte) | 103 | 62* |

*p < 0.01

The compound of Example 4 did not decrease the reticulocyte count and therefore had a higher safety than the comparative compound.

Test Example 3

Repeated-Dose Toxicity Test in Mice (2)

The compound of Example 3 was selected as a compound of the invention. Among compounds described in the Examples of WO03/074476, a compound having a structure most analogous to that of the compound of the invention was selected as a comparative compound. Their chemical structures are as follows.

the test compound-treated groups when a value in the control group is set to 100 are shown in Table 3.

(Hematological Test Items and Determination Methods)

Red blood cell count (RBC): Two-angle laser flow cytometry

Reticulocyte count: Flow cytometry after RNA staining

TABLE 3

| Compound | Example 3 | | Comparative compound |
| --- | --- | --- | --- |
| Dose (mg/kg) | 6.25 | 3.13 | 3.13 |
| Red blood cell count (RBC) | 98.7 | 96.4 | 96.2 |
| Reticulocyte count (Reticulocyte) | 96.4 | 93.5 | 76.7* |

*p < 0.01

The comparative compound decreased the reticulocyte count at a dose of 3.13 mg/kg. On the other hand, the compound of Example 3 did not decrease the reticulocyte count even at a dose of 6.25 mg/kg, and therefore had a much higher safety than the comparative compound.

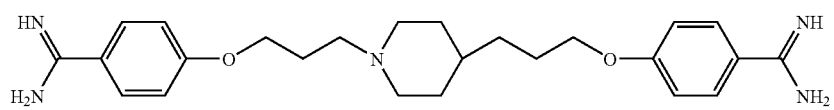

[Example 3]

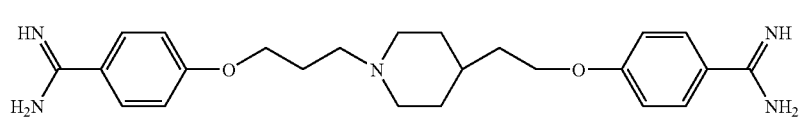

[Comparative compound]

Six-week old male ICR mice (body weight range: 27.4 to 33.7 g, the number of animals allocated to each group: 5) were used to examine the repeated-dose toxicity. A solution of each test compound was prepared by dissolution in 0.1 mol/L hydrochloric acid. Each compound was subcutaneously administered at a dose of 6.25 or 3.13 mg/kg once a day for 14 days. A sterilized physiological saline was administered to a control group. At the end of the administration period, each mouse was anesthetized with ether. An injection syringe containing a heparin solution (Novo-Heparin Injection 1000, Aventis Pharma K.K.) as an anticoagulant was used for blood collection from abdominal portion of vena cava. A hematological test was carried out for the following items. Values in Test Example 4

Vero Cell Proliferation Inhibition Test

The compound of Example 4 was selected as a compound of the invention. Among compounds described in the Examples of WO03/074476, a compound having a structure most analogous to that of the compound of the invention was selected as a comparative compound. Their chemical structures are as follows.

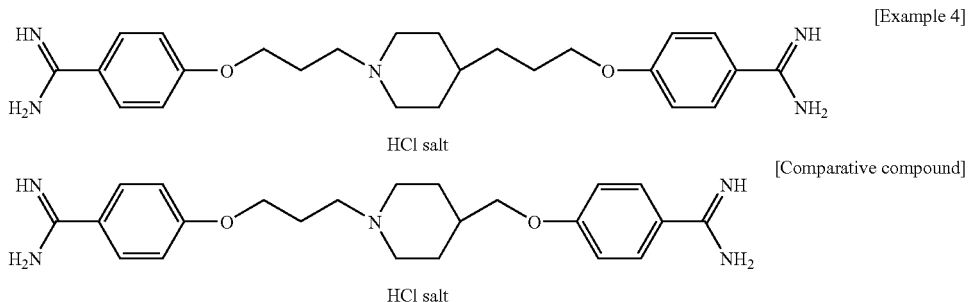

The cytotoxicity of each compound was evaluated using Vero cells. Each test compound was dissolved in dimethylsulfoxide (DMSO), which was then subjected to serial dilution with 10% FBS-containing E'MEM and added to a 96-well plate. The cells were suspended in 10% FBS-containing E'MEM, inoculated in an amount of 3,000 cells/well (96-well plate), and cultured in a $CO_2$ incubator at 37° C. for 3 days. The degree of growth of Vero cells was evaluated using a 2,3-bis-(2-methoxy-4-nitro-5-sulfophenyl)-5-[(phenylamino)carbonyl]-2H-tetrazolium=inner salt=monosodium salt (XTT) assay. Thus, an XTT solution containing 1 mg/mL XTT and 25 μmol/L phenazine=methosulfate (PMS) was added to each well, which was then incubated in a $CO_2$ incubator for 2 hours, followed by determining the absorbance of the well at 450 nm (reference: 655 nm) using a micro plate reader. The absorbance ratio between the control (no added compound) and each of the wells was calculated, and the concentration ($CC_{50}$; μg/mL) of compound inhibiting cell proliferation by 50% was computed. The results are shown in Table 4.

TABLE 4

| Compound | Example 4 | Comparative compound |
|---|---|---|
| $CC_{50}$ (μg/mL) | 25 | 6 |

The compound of Example 4 had a higher safety than the comparative compound.

Test Example 5

Hygroscopicity Test (1)

The compound of Example 4 was selected as a compound of the invention. Among compounds described in the Examples of WO03/074476, a compound having a structure most analogous to that of the compound of the invention was selected as a comparative compound. Their chemical structures are as follows.

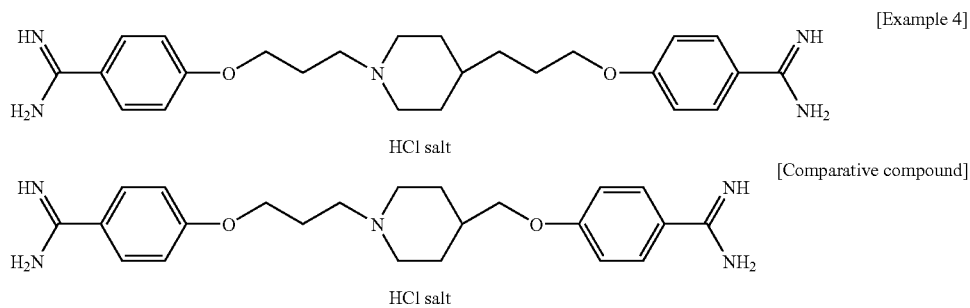

The compound of Example 4 and the comparative compound were stored under conditions of room temperature and a relative humidity of 75% or 60° C. and a relative humidity of 75% for one week. As a result, the compound of Example 4 was powder without any change in the appearance under any of the conditions. On the other hand, the comparative compound was changed into a paste form under both of the conditions.

The compound of Example 4 had a higher stability than the comparative compound.

Test Example 6

Hygroscopicity Test (2)

The compound of Example 10 was selected as a compound of the invention. Among compounds described in the Examples of WO03/074476, a compound having a structure most analogous to that of the compound of the invention was selected as a comparative compound. Their chemical structures are as follows.

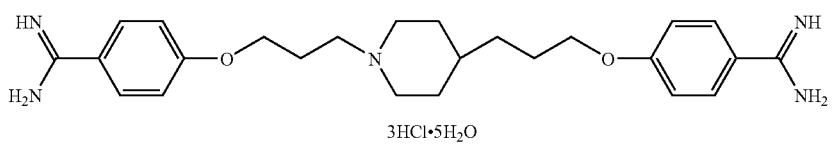

[Example 10]

3HCl·5H₂O

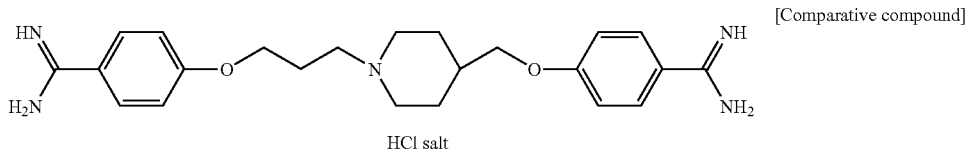

[Comparative compound]

HCl salt

The compound of Example 10 and the comparative compound were stored under conditions of room temperature and a relative humidity of 100% for one week, and weighed. The results are shown in Table 5.

TABLE 5

| Compound | Example 10 | Comparative compound |
|---|---|---|
| Weight increase ratio (%) | 0 | 25 |

The compound of Example 10 was not hygroscopic at all, and had a higher stability than the comparative compound.

Test Example 7

Hygroscopicity Test (3)

The compound of Example 10 was selected as a compound of the invention. Among compounds described in the Examples of WO03/074476, a compound having a structure most analogous to that of the compound of the invention was selected as a comparative compound. Their chemical structures are as follows.

The compound of Example 10 and the comparative compound were stored under conditions of 60° C. and a relative humidity of 100% for one week. As a result, the comparative compound deliquesced. On the other hand, the compound of Example 10 did not deliquesce and was stable.

Test Example 8

Antiprotozoan Action

The antiprotozoan activity of the compound of Example 3 was determined.

Trichomonas vaginalis CDC337 was cultured in a Diamond's trypticase-yeast-maltose medium (pH 6.8) containing 8% fetal bovine serum (FBS). The protozoan bodies which had been cultured 37° C. for 2 days were centrifuged (1,500 rpm, 10 minutes) and subjected to medium replacement with a fresh medium before adjustment to $2 \times 10^4$ bodies/mL, followed by dispensing them in an amount of 100 μL/well in a micro plate (96-well, flat bottom). The test compound was dissolved using 0.1 mol/L hydrochloric acid, which was then diluted to a predetermined concentration with the medium, followed by dispensing 100 μL/well thereof into a micro plate. The minimal test compound concentration at which the movement of the bodies was not observed after culture 37° C. under anaerobic conditions for 2 days was defined as MIC.

The MIC of the compound of Example 10 was 16 μg/mL.

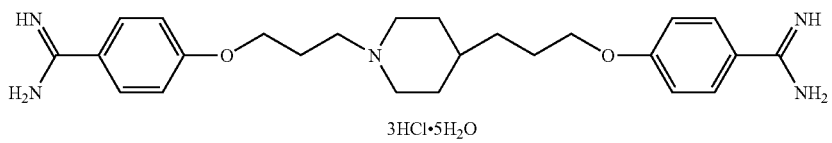

[Example 10]

3HCl·5H₂O

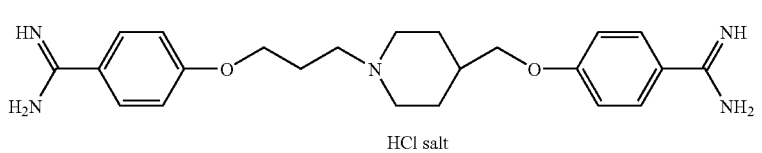

[Comparative compound]

HCl salt

Test Example 9

Mouse *Candida* Infection Model Test (Oral Administration)

The compound of Example 47 was selected as a compound of the invention. The chemical structure thereof is as follows.

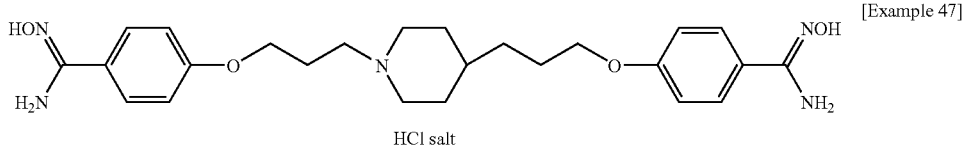

[Example 47]

HCl salt

*Candida albicans* TIMM1623 on a SDA plate, which had been cultured overnight at 35° C. was suspended in a sterilized physiological saline, which was then diluted to prepare a suspension of inoculum organism. To make mice in a transiently compromised state, cyclophosphamide was intraperitoneally administered at 200 mg/kg 4 days before infection and at 100 mg/kg the next day after infection. Into the tail vein of mice was inoculated 0.2 mL of the prepared solution of inoculum *Candida albicans* TIMM1623 to induce infection (about $3 \times 10^4$ CFU/mouse). The test compound was suspended in 0.5% methylcellulose and orally administered at 1 mg/kg of mouse body weight. The treatment was started from 2 hours after infection and carried out for 7 days. The survival number of mice was observed for 21 days after infection, and recorded.

As a result, all mice died in a group to which no test compound was administered, but 80% of mice survived in the group to which the compound of Example 47 was administered.

The compound of Example 47 also had an excellent therapeutic effect even when orally administered.

In the in vitro and in vivo tests, the compounds of the invention had equivalent or more excellent antifungal activities than the comparative compound. In the repeated-dose toxicity tests, the compounds of the invention did not decrease the reticulocyte count and had a higher safety than the comparative compound. In addition, the comparative compound was difficult in quality control because it was hygroscopic and deliquescent, but the compounds of the invention were not hygroscopic, and more excellent as drug substance than the comparative compound. Further, the compounds of the invention had an excellent effect against protozoa.

EXAMPLES

The present invention will be now described in the following Reference Examples and Examples. However, the invention is not intended to be limited thereto.

Mixing ratios in eluents are all volume mixing ratios, and the carrier used in column chromatography is B.W. Silica Gel or BW-127ZH (Fuji Silysia Chemical Ltd.) unless otherwise described.

The abbreviations in Examples mean the following.

Ac: acetyl, Boc: tert-butoxycarbonyl, $^t$Bu: tert-butyl, Et: ethyl, Me: methyl, Ms: methanesulfonyl DMSO-$d_6$: dimethylsulfoxide-$d_6$

REFERENCE EXAMPLE 1

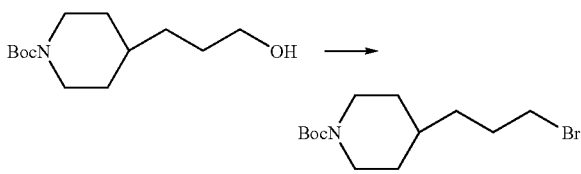

To a tetrahydrofuran (110 mL) solution of 10.7 g of tert-butyl=4-(3-hydroxypropyl)-1-piperidinecarboxylate was added 19.0 g of carbon tetrabromide under cooling with water, to which 15.0 g of triphenylphosphine was then added over a period of 13 minutes. This mixture was stirred at room temperature for 2 hours and 30 minutes and allowed to stand for 13 hours. To the reaction mixture were added water, ethyl acetate, and a saturated sodium chloride aqueous solution. The organic layer was separated, washed with a saturated sodium chloride aqueous solution, and dried with anhydrous magnesium sulfate, followed by distilling off the solvent under reduced pressure. The resultant residue was purified using silica gel column chromatography (eluent; hexane: ethyl acetate=3:1) to provide 13.2 g of tert-butyl=4-(3-bromopropyl)-1-piperidinecarboxylate as colorless oily form.

$^1$H-NMR (CDCl$_3$) δ value: 1.00-1.20(2H, m), 1.20-1.50 (3H, m), 1.45(9H, s), 1.60-1.70(2H, m), 1.80-1.95(2H, m), 2.60-2.75(2H, m), 3.40(2H, t, J=6.8 Hz), 3.90-4.25(2H, m).

REFERENCE EXAMPLE 2

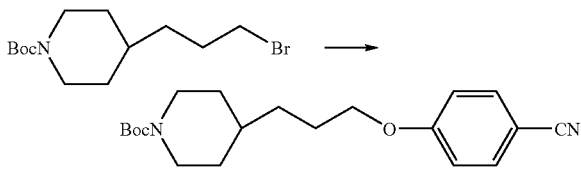

To a dimethylsulfoxide (130 mL) solution of 13.2 g of tert-butyl=4-(3-bromopropyl)-1-piperidinecarboxylate were added 5.13 g of 4-cyanophenol and 11.9 g of potassium carbonate at room temperature, which was then stirred at the same temperature for 26 hours. The reaction mixture was added to a mixture of toluene and water. The organic layer was separated, washed with a saturated sodium chloride aqueous solution, and dried with anhydrous magnesium sulfate, followed by distilling off the solvent under reduced pressure to provide 14.5 g of tert-butyl=4-[3-(4-cyanophenoxy)propyl]-1-piperidinecarboxylate as white solid form.

¹H-NMR (CDCl₃). δ value: 1.05-1.20(2H, m), 1.40-1.50 (3H, m), 1.46(9H, s), 1.65-1.75(2H, m), 1.75-1.90(2H, m), 2.60-2.80(2H, m), 3.99(2H, t, J=6.3 Hz), 4.00-4.20(2H, m), 6.93(2H, d, J=8.7 Hz), 7.58(2H, d, J=8.7 Hz).

REFERENCE EXAMPLE 3

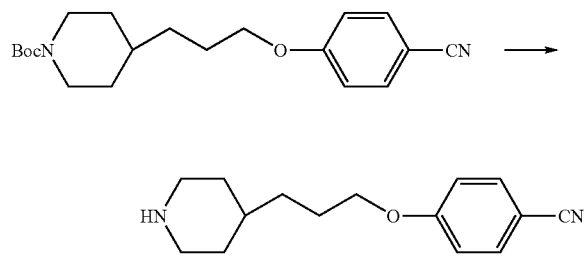

To a chloroform (100 mL) solution of 14.0 g of tert-butyl=4-[3-(4-cyanophenoxy)propyl]-1-piperidinecarboxylate was dropwise added 40 mL of trifluoroacetic acid under cooling with water over a period of 10 minutes. This mixture was stirred at the same temperature for 20 minutes, and then stirred at room temperature for 35 minutes. After distilling off the solvent under reduced pressure, chloroform and water were added. A sodium hydroxide aqueous solution was added thereto for adjustment to pH 13.0. The organic layer was separated, and the aqueous layer was extracted with chloroform. The organic layer and the extract were combined, which was then washed with a sodium hydroxide aqueous solution and dried with potassium carbonate, followed by distilling off the solvent under reduced pressure to provide 10.3 g of 4-[3-(4-piperidinyl)propoxy]benzonitrile as pale yellow solid form.

¹H-NMR (CDCl₃) . δvalue: 1.05-1.20(2H, m), 1.35-1.45 (3H, m), 1.65-1.90(4H, m), 2.50-2.65(2H, m), 3.00-3.15(2H, m), 3.99(2H, t, J=6.6 Hz), 4.78(1H, s), 6.93(2H, d, J=9.0Hz), 7.58(2H, d, J=9.0 Hz).

REFERENCE EXAMPLE 4

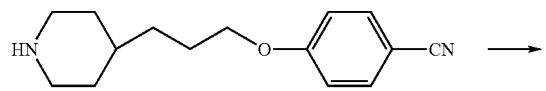

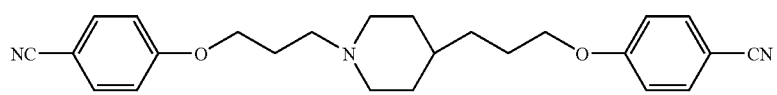

To an N,N-dimethylformamide (150 mL) solution of 10.2 g of 4-[3-(4-piperidinyl)propoxy]benzonitrile were sequentially added 11.2 g of potassium carbonate and 9.72 g of 4-(3-bromopropoxy)benzonitrile at room temperature, which was then stirred at the same temperature for 18 hours. Toluene and water were added to the reaction mixture. The precipitate was collected by filtration to provide 13.7 g of 4-(3-{4-[3-(4-cyanophenoxy)propyl]-1-piperidinyl}propoxy)benzonitrile as white solid form.

¹H-NMR (CDCl₃) . δvalue: 1.20-1.45(5H, m), 1.65-2.05 (8H, m), 2.40-2.55(2H, m), 2.85-3.00(2H, m), 3.99(2H, t, J=6.5 Hz), 4.06(2H, t, J=6.3 Hz), 6.93(2H, d, J=8.8 Hz), 6.94(2H, d, J=8.8 Hz), 7.57(2H, d, J=8.8 Hz), 7.57 (2H, d, J=8.8 Hz)

REFERENCE EXAMPLE 5

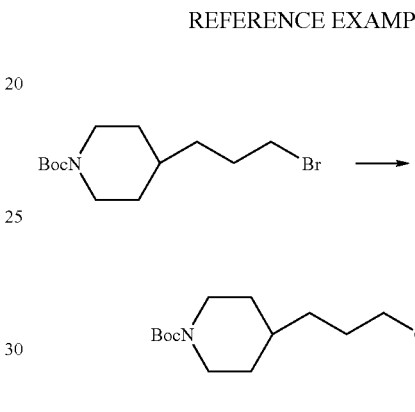

A 2-butanone (7.6 mL) solution of 1.12 g of tert-butyl=4-(3-bromopropyl)-1-piperidinecarboxylate was added to a 2-butanone (7.0 mL) mixture of 0.50 g of 2-fluoro-4-hydroxybenzonitrile and 0.56 g of potassium carbonate, which was then heated to reflux for 6 hours and 30 minutes. After cooling down to room temperature, the reaction mixture was added to a mixture of ethyl acetate and water. The organic layer was separated, washed with water, and dried with anhydrous magnesium sulfate, followed by distilling off the solvent under reduced pressure. The resultant residue was purified using silica gel column chromatography (eluent; hexane: ethyl acetate=4:1) to provide 0.72 g of tert-butyl=4-[3-(4-cyano-3-fluorophenoxy)propyl]-1-piperidinecarboxylate as colorless oily form.

¹H-NMR (CDCl₃) . δvalue: 1.05-1.20(2H, m), 1.35-1.45 (3H, m), 1.46(9H, s), 1.65-1.75(2H, m), 1.75-1.90(2H, m), 2.60-2.75(2H, m), 3.99(2H, t, J=6.3 Hz), 4.00-4.20(2H, m), 6.65-6.80(2H, m), 7.45-7.54(1H, m).

REFERENCE EXAMPLE 6

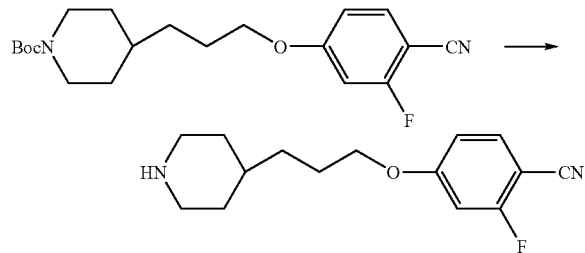

To a methylene chloride (5.5 mL) solution of 0.66 g of tert-butyl=4-[3-(4-cyano-3-fluorophenoxy)propyl]-1-piperidinecarboxylate was dropwise added 1.8 mL of trifluoroacetic acid under cooling with ice over a period of 2 minutes, which was then stirred at room temperature for 6 hours. The solvent was distilled off under reduced pressure, and chloroform and a 1.0 mol/L sodium hydroxide aqueous solution were added to the resultant residue. The organic layer was separated and dried with anhydrous magnesium sulfate, followed by distilling off the solvent under reduced pressure. The resultant residue was purified using silica gel column chromatography (eluent; chloroform:methanol=4:1) to provide 0.28 μg of 2-fluoro-4-[3-(4-piperidinyl)propoxy]benzonitrile as pale yellow oily form.

$^1$H-NMR (CDCl$_3$) δvalue: 1.05-1.20(2H, m), 1.30-1.45 (3H, m), 1.50-1.75(2H, m), 1.75-1.90(2H, m), 2.50-2.65(2H, m), 3.00-3.15(2H, m), 3.98(2H, t, J=6.5 Hz), 6.69(1H, dd, J=11.0, 2.3 Hz), 6.75(1H, dd, J=8.5, 2.3 Hz), 7.50(1H, dd, J=8.5, 8.5 Hz).

REFERENCE EXAMPLE 7

To an N,N-dimethylformamide solution (2.0 mL) of 0.10 g of 2-fluoro-4-[3-(4-piperidinyl)propoxy]benzonitrile were sequentially added 0.10 g of potassium carbonate and 0.13 g of 4-(3-bromopropoxy)benzonitrile at room temperature, which was then stirred at the same temperature for 13 hours. Ethyl acetate, water, and toluene were added to the reaction mixture. The organic layer was separated and dried with anhydrous sodium sulfate, followed by distilling off the solvent under reduced pressure. The resultant residue was purified using silica gel column chromatography (eluent; chloroform:methanol=4:1) to provide 68 mg of 4-(3-{1-[3-(4-cyanophenoxy)propyl]-4-piperidinyl}propoxy)-2-fluorobenzonitrile as white solid form.

$^1$H-NMR (CDCl$_3$) δvalue: 1.20-1.45(5H, m), 1.65-2.05 (8H, m), 2.40-2.55(2H, m), 2.85-3.00(2H, m), 3.98(2H, t, J=6.5 Hz), 4.06(2H, t, J=6.3 Hz), 6.69(1H, dd, J=11.0, 2.4 Hz), 6.74(1H, dd, J=8.8, 2.4 Hz), 6.94(2H, d, J=8.7 Hz), 7.45-7.55(1H, m), 7.57(2H, d, J=8.7 Hz).

REFERENCE EXAMPLE 8

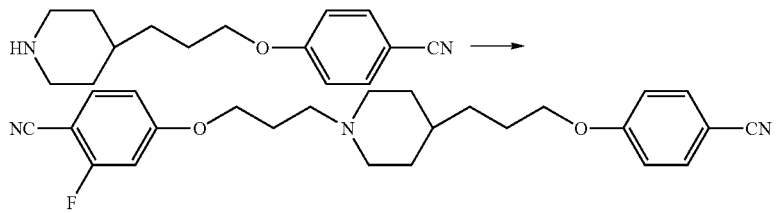

As described in Reference Example 7, 0.12 g of 4-[3-(4-piperidinyl)propoxy]benzonitrile and 0.15 g of 4-(3-bromopropoxy)-2-fluorobenzonitrile were used to provide 0.10 g of 4-(3-{4-[3-(4-cyanophenoxy)propyl]-1-piperidinyl}propoxy)-2-fluorobenzonitrile as white solid form.

$^1$H-NMR (CDCl$_3$) δvalue: 1.20-1.35(3H, m), 1.35-1.45 (2H, m), 1.60-2.05(8H, m), 2.40-2.50(2H, m), 2.85-3.00(2H, m), 3.99(2H, t, J=6.5 Hz), 4.06(2H, t, J=6.3 Hz), 6.70-6.80 (2H, m), 6.93(2H, d, J=9.0 Hz), 7.45-7.55(1H, m), 7.57(2H, d, J=9.0 Hz).

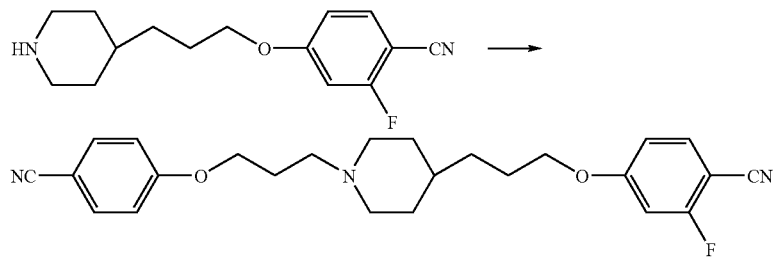

REFERENCE EXAMPLE 9

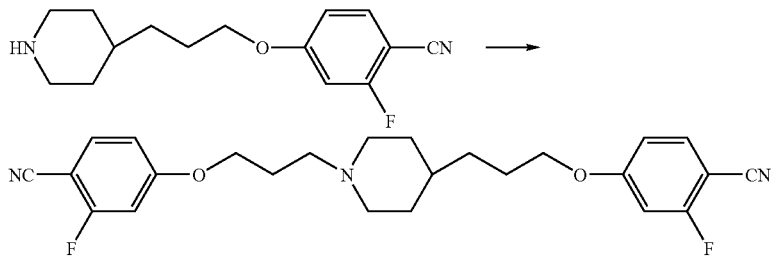

To a dimethylsulfoxide (4.0 mL) solution of 0.26 g of 2-fluoro-4-[3-(4-piperidinyl)propoxy]benzonitrile and 0.21 g of 4-(3-chloropropoxy)-2-fluorobenzonitrile was added 0.88 mL of N-ethyldiisopropylamine, which was then stirred at 80 to 90° C. for 8 hours and 15 minutes. The reaction mixture was cooled down to room temperature, to which water was then added, followed by extraction with ethyl acetate. The extract was washed twice with water and dried with anhydrous magnesium sulfate, followed by distilling off the solvent under reduced pressure. The resultant residue was purified using silica gel column chromatography (eluent; chloroform:methanol=10:1) to provide 0.25 g of 4-(3-{1-[3-(4-cyano-3-fluorophenoxy)propyl]-4-piperidinyl}propoxy)-2-fluorobenzonitrile as brown solid form.

$^1$H-NMR (CDCl$_3$) . δvalue: 1.20-1.45(5H, m), 1.65-2.05 (8H, m), 2.40-2.50(2H, m), 2.85-3.00(2H, m), 3.98(2H, t, J=6.5 Hz), 4.06(2H, t, J=6.3 Hz), 6.65-6.80(4H, m), 7.45-7.55(2H, m).

REFERENCE EXAMPLE 10

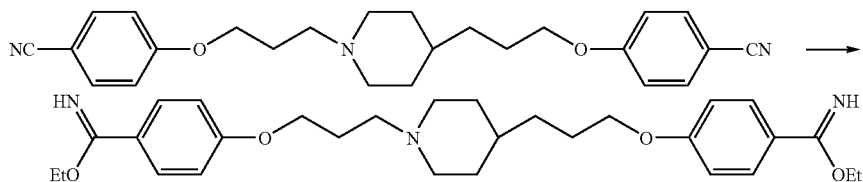

Hydrogen chloride was introduced into an ethanol (16 mL) suspension of 0.80 g of 4-(3-{4-[3-(4-cyanophenoxy)propyl]-1-piperidinyl}propoxy)benzonitrile under cooling with ice, which was then stirred at room temperature for 15 hours. The solvent was distilled off under reduced pressure, and the resultant residue was dissolved in chloroform and added to a mixture of a saturated sodium bicarbonate aqueous solution and chloroform. The organic layer was separated and dried with anhydrous magnesium sulfate, followed by distilling off the solvent under reduced pressure to provide 0.77 g of ethyl=4-{3-[4-(3-{4-[ethoxy(imino)methyl] phenoxy}propyl)-1-piperidinyl]propoxy}benzimidate as white solid form.

$^1$H-NMR (CDCl$_3$) . δvalue: 1.20-1.45(5H, m), 1.41(3H, t, J=7.1 Hz), 1.41(3H, t, J=7.1 Hz), 1.65-2.05(8H, m), 2.45-2.55(2H, m), 2.90-3.00(2H, m), 3.98(2H, t, J=6.5 Hz), 4.04 (2H, t, J=6.3 Hz), 4.20-4.40(4H, m), 6.89(2H, d, J=8.5 Hz), 6.90(2H, d, J=8.8 Hz), 7.60-7.80(4H, m).

REFERENCE EXAMPLE 11

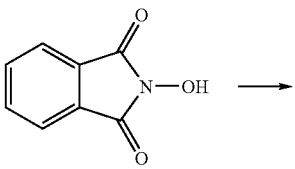

-continued

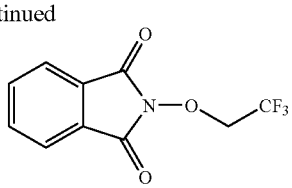

A dichloromethane (21 mL) solution of 3.9 mL of 2,2,2-trifluoroethanol and 4.3 mL of pyridine was added dropwise to a dichloromethane (83 mL) solution of 9.0 mL of trifluoromethanesulfonic anhydride under cooling with ice over a period of 25 minutes. Thereto was dropwise added a dichloromethane (60 mL) solution of 8.50 g of N-hydroxyphthalimide and 18.5 mL of N,N-diisopropylethylamine at the same temperature over a period of 45 minutes, which was then stirred for 22 hours. To the reaction mixture was added 100 mL of 1 mol/L hydrochloric acid. The organic layer was separated, washed sequentially with 1 mol/L hydrochloric acid and a saturated sodium chloride aqueous solution, and then dried with anhydrous magnesium sulfate, followed by distilling off the solvent under reduced pressure. The resultant residue was purified using silica gel column chromatography (eluent; hexane:ethyl acetate=3:1) and washed with hexane to provide 4.43 g of N-(2,2,2-trifluoroethoxy)phthalimide as white solid form.

$^1$H-NMR (CDCl$_3$) . δvalue: 4.56(2H, q, J=8.0 Hz), 7.75-7.95(4H, m).

REFERENCE EXAMPLE 12

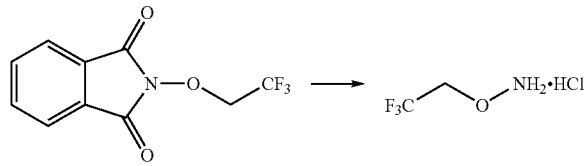

To a dichloromethane (45 mL)/methanol (5.9 mL) mixture of 4.30 g of N-(2,2,2-trifluoroethoxy)phthalimide was dropwise added 0.85 mL of hydrazine monohydrate at room temperature, which was then stirred at the same temperature for 3 hours. To the reaction mixture was added 10 mL of 2.9 mol/L hydrogen chloride/ethanol, followed by distilling off the solvent under reduced pressure to provide 2.65 g of O-(2,2,2-trifluoroethyl)hydroxylamine hydrochloride as white solid form.

$^1$H-NMR (DMSO-d$_6$). δvalue: 4.60(2H, q, J=9.0 Hz), 7.80-7.85(1H, m).

REFERENCE EXAMPLE 13

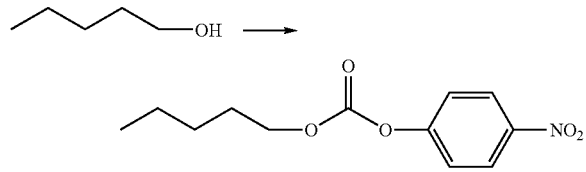

A tetrahydrofuran (10 mL) solution of 1.00 g of 4-nitrophenyl=chloroformate was added dropwise to a tetrahydrofuran (5 mL) solution of 0.44 g of pentanol and 0.76 mL of triethylamine under cooling with ice. The mixture was stirred at room temperature for 2 hours and 20 minutes, and ethyl acetate and water were then added to the reaction mixture. The organic layer was separated, washed sequentially with a 5% potassium carbonate aqueous solution and a saturated sodium chloride aqueous solution, and then dried with anhydrous magnesium sulfate, followed by distilling off the solvent under reduced pressure to provide 1.20 g of 4-nitrophenyl=pentyl=carbonate as colorless oily form.

$^1$H-NMR (CDCl$_3$) . δvalue: 0.94(3H, t, J=7.1 Hz), 1.30-1.50(4H, m), 1.70-1.85(2H, m), 4.29(2H, t, J=6.7 Hz), 7.39 (2H, d, J=9.3 Hz), 8.28(2H, d, J=9.3 Hz)

REFERENCE EXAMPLE 14

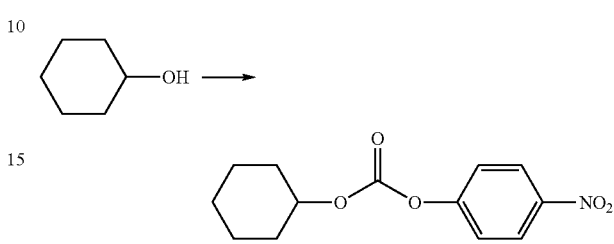

As described in Reference Example 13, 1.49 g of cyclohexyl=4-nitrophenyl=carbonate as white solid was obtained from 0-50 g of cyclohexanol and 1.00 g of 4-nitrophenyl=chloroformate.

$^1$H-NMR (CDCl$_3$) . δvalue: 1.20-1.65(6H, m), 1.75-1.85 (2H, m), 1.95-2.05(2H, m), 4.70-4.80(1H, m), 7.39(2H, d, J=9.0 Hz), 8.28(2H, d, J=9.0 Hz).

REFERENCE EXAMPLE 15

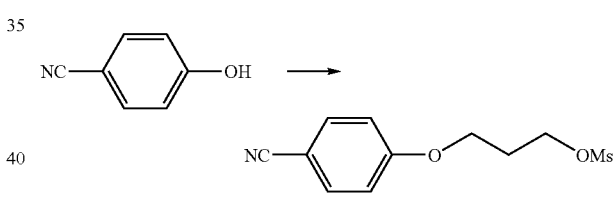

To an N,N-dimethylformamide (15 mL) suspension of 9.42 g of potassium=tert-butoxide were added 10.0 g of 4-cyanophenol and 7.02 mL of 3-chloro-1-propanol under cooling with water, which was then stirred at 100° C. for one hour. The reaction mixture was cooled down to room temperature, to which water and ethyl acetate were then added. The organic layer was separated, washed sequentially with a 5% potassium carbonate aqueous solution and a saturated sodium chloride aqueous solution, and then dried with anhydrous magnesium sulfate, followed by distilling off the solvent under reduced pressure. In 100 mL of dioxane was dissolved 11.9 g of the resultant oily matter. To this mixture was added 9.28 mL of triethylamine, to which 5.15 mL of methanesulfonyl chloride was then added dropwise under cooling with ice over a period of 8 minutes, followed by stirring at room temperature for 10 minutes. To the reaction mixture was dropwise added 100 mL of water, which was then stirred at room temperature for 45 minutes. The precipitate was collected by filtration and washed with water and 2-propanol to provide 12.3 g of 3-(4-cyanophenoxy) propyl=methanesulfonate as white solid form.

$^1$H-NMR (CDCl$_3$) . δvalue:

2.27(2H, tt, J=6.0, 6.0 Hz), 3.02(3H, s), 4.15(2H, t, J=6.0 Hz), 4.45(2H, t, J=6.0 Hz), 6.96(2H, d, J=8.9 Hz), 7.60(2H, d, J=8.9 Hz

REFERENCE EXAMPLE 16

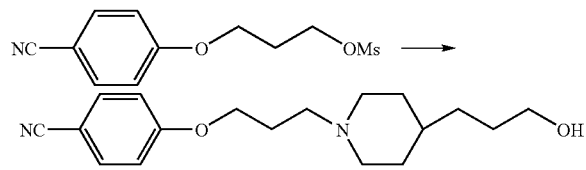

To an N,N-dimethylformamide (250 mL) solution of 50.0 g of 3-(4-cyanophenoxy)propyl=methanesulfonate were added 32.5 g of potassium iodide, 32.9 g of sodium bicarbonate, and 37.0 g of 3-(4-piperidinyl)-1-propanol hydrochloride at room temperature, which was then stirred at 70° C. for 6 hours and 50 minutes. The reaction mixture was cooled down to room temperature, to which water and toluene were then added, followed by adjustment to pH 1.0 using hydrochloric acid. The aqueous layer was separated, adjusted to pH 10.0 using a 20% sodium hydroxide aqueous solution, and stirred at room temperature for 15 minutes and then under cooling with ice for 30 minutes. The precipitate was collected by filtration and washed with water and toluene to provide 52.3 g of 4-{3-[4-(3-hydroxypropyl)-1-piperidinyl]propoxy}benzonitrile as white solid form.

$^1$H-NMR (CDCl$_3$) δvalue: 1.20-1.75(10H, m), 1.85-2.05(4H, m), 2.40-2.55(2H, m), 2.85-3.0-0(2H, m), 3.64(2H, t, J=6.6 Hz), 4.06(2H, t, J=6.3 Hz), 6.94(2H, d, J=9.0 Hz), 7.57(2H, d, J=9.0 Hz)

REFERENCE EXAMPLE 17

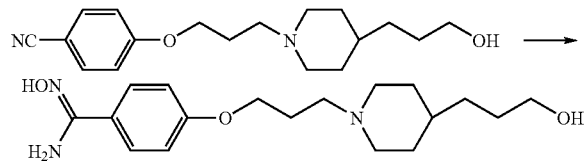

To a dimethylsulfoxide (200 mL) solution of 18.7 g of 4-{3-[4-(3-hydroxypropyl)-1-piperidinyl]propoxy}benzonitrile was added 8.92 mL of a 50% hydroxylamine aqueous solution at room temperature, which was then stirred at the same temperature for 5 hours and 30 minutes. Thereto was added 8.92 mL of a 50% hydroxylamine aqueous solution at room temperature, which was stirred at the same temperature for 15 hours and 50 minutes. To the reaction mixture were added 2-propanol and water, which was then stirred at room temperature for one hour. The precipitate was collected by filtration and washed with water to provide 17.5 g of N'-hydroxy-4-{3-[4-(3-hydroxypropyl)-1-piperidinyl]propoxy}benzamidine as white solid form.

$^1$H-NMR (DMSO-d$_6$) δvalue: 1.00-1.25(5H, m), 1.35-1.45(2H, m), 1.55-1.65(2H, m), 1.75-1.90(4H, m), 2.35-2.45(2H, m), 2.80-2.90(2H, m), 3.30-3.40(2H, m), 4.00(2H, t, J=6.5 Hz), 4.34(1H, t, J=5.1 Hz), 5.60-5.80(2H, broad), 6.90(2H, d, J=8.7 Hz), 7.58(2H, d, J=8.7 Hz), 9.43 (1H, s)

REFERENCE EXAMPLE 18

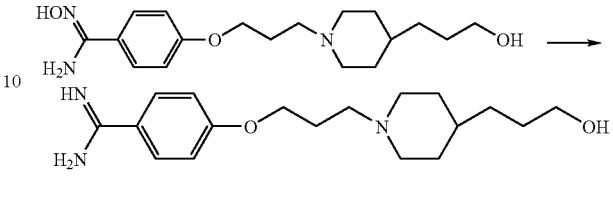

To an acetic acid (80 mL) suspension of 10.0 g of N'-hydroxy-4-{3-[4-(3-hydroxypropyl)-1-piperidinyl]propoxy}benzamidine were added 5.31 mL of acetic anhydride and 0.50 g of 5% palladium-carbon at room temperature, which was stirred at room temperature under hydrogen atmosphere for 12 hours and 50 minutes. After filtering off insoluble matter, the solvent was distilled off under reduced pressure. To the resultant residue was added 6 mol/L hydrochloric acid, followed by distilling off the solvent under reduced pressure before purification using silica gel column chromatography (silica gel: ODS-A from YMC, eluent; water). The eluate was concentrated to about 100 mL under reduced pressure and then adjusted to pH 12 using a 5 mol/L sodium hydroxide aqueous solution. The precipitate was collected by filtration and washed with water to provide 8.43 g of 4-{3-[4-(3-hydroxypropyl)-1-piperidinyl]propoxy}benzamidine as white solid form.

$^1$H-NMR (DMSO-d$_6$) δvalue: 1.00-1.25(5H, m), 1.35-1.45(2H, m), 1.55-1.65(2H, m), 1.75-1.90(4H, m), 2.30-2.45(2H, m), 2.80-2.90(2H, m), 3.30-3.40(2H, m), 4.03(2H, t, J=6.3 Hz), 6.95(2H, d, J=8.8 Hz), 7.72(2H, d, J=8.8 Hz).

REFERENCE EXAMPLE 19

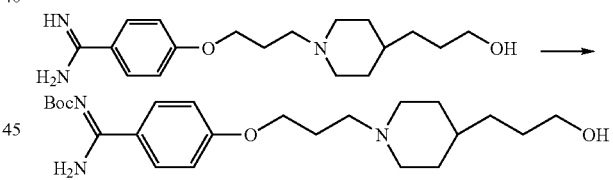

To a dioxane (10 mL) suspension of 2.00 g of 4-{3-[4-(3-hydroxypropyl)-1-piperidinyl]propoxy}benzamidine were sequentially added 1.37 g of di-tert-butyl=dicarbonate, 4 mL of N,N-dimethylformamide, and 10 mL of a 2.5 mol/L sodium hydroxide aqueous solution at room temperature, which was then stirred at the same temperature for 45 minutes. Thereto was added 1.37 g of di-tert-butyl=dicarbonate at room temperature, which was then stirred at the same temperature for 2 hours and 45 minutes. Insoluble matter was filtered off, and chloroform and water were added to the filtrate. The organic layer was separated, washed with a saturated sodium chloride aqueous solution, and then dried with anhydrous magnesium sulfate, followed by distilling off the solvent under reduced pressure. The resultant residue was purified using silica gel column chromatography (eluent; chloroform:methanol=4:1) to provide 2.35 g of tert-butyl=[1-amino-1-(4-{3-[4-(3-hydroxypropyl)-1-piperidinyl]propoxy}phenyl)methylidene]carbamate as pale red solid form.

¹H-NMR (CDCl₃) δvalue: 1.15-1.35(5H, m), 1.35-1.75 (4H, m), 1.55(9H, s), 1.85-2.05(4H, m), 2.45-2.55(2H, m), 2.85-3.00(2H, m), 3.64(2H, t, J=6.6 Hz), 4.05(2H, t, J=6.5 Hz), 6.91(2H, d, J=8.8 Hz), 7.83(2H, d, J=8.8 Hz).

REFERENCE EXAMPLE 20

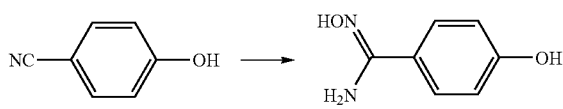

To a dimethylsulfoxide (100 mL) solution of 10.0 g of 4-cyanophenol was dropwise added 12.9 mL of a 50% hydroxylamine aqueous solution at room temperature over a period of 6 minutes, which was then stirred at the same temperature for 14 hours. Chloroform, a 1 mol/L sodium hydroxide aqueous solution, and water were added to the reaction mixture. The aqueous layer was separated and washed sequentially with toluene, chloroform, and toluene, to which water was then added, followed by adjustment to pH 7.2 using 6 mol/L hydrochloric acid. After stirring this mixture at room temperature for 30 minutes, the precipitate was collected by filtration and washed with water to provide 8.88 g of N', 4-dihydroxybenzamidine as white solid form.

¹H-NMR (DMSO-d₆) δvalue: 5.50-5.70(2H, broad), 6.73(2H, d, J=8.5 Hz), 7.47(2H, d, J=8.5 Hz), 9.34 (1H, s), 9.50-9.60(1H, broad).

REFERENCE EXAMPLE 21

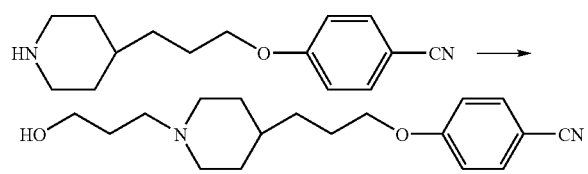

To an N,N-dimethylformamide (70 mL) solution of 9.81 g of 4-[3-(4-piperidinyl)propoxy]benzonitrile were added 8.02 g of potassium carbonate and 2.62 mL of 3-bromo-1-propanol at room temperature, which was then stirred at the same temperature for 2 hours and 15 minutes. Thereto was added 2.62 mL of 3-bromo-1-propanol, which was then stirred at the same temperature for 1 hour and 45 minutes. Chloroform and water were added to the reaction mixture. The organic layer was separated, washed sequentially with a 1 mol/L sodium hydroxide aqueous solution and a saturated sodium chloride aqueous solution, and then dried with anhydrous magnesium sulfate, followed by distilling off the solvent under reduced pressure. The resultant residue was purified using silica gel column chromatography (eluent; chloroform:methanol=4:1) to provide 4.28 g of 4-{3-[1-(3-hydroxypropyl)-4-piperidinyl]propoxy}benzonitrile as white solid form.

¹H-NMR (CDCl₃) δvalue: 1.15-1.45(5H, m), 1.65-2.00 (8H, m), 2.55-2.65(2H, m), 3.00-3.10(2H, m), 3.81(2H, t, J=5.2 Hz), 3.98(2H, t, J=6.5 Hz), 6.92(2H, d, J=8.5 Hz), 7.57(2H, d, J=8.5 Hz).

REFERENCE EXAMPLE 22

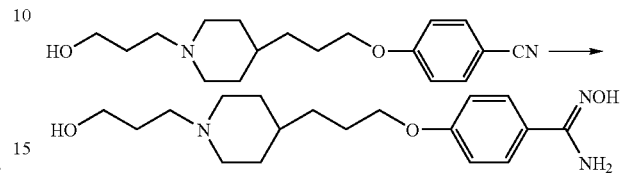

To a dimethylsulfoxide (43 mL) suspension of 4.27 g of 4-{3-[1-(3-hydroxypropyl)-4-piperidinyl]propoxy}benzonitrile was added 4.32 mL of a 50% hydroxylamine aqueous solution at room temperature, which was then stirred at 40 to 50° C. for 3 hours and 30 minutes. The reaction mixture was cooled down to room temperature, to which 50 mL of water was then added dropwise over a period of 10 minutes, followed by stirring at room temperature for 30 minutes. The precipitate was collected by filtration and washed with water to provide 4.59 g of N'-hydroxy-4-{3-[1-(3-hydroxypropyl)-4-piperidinyl]propoxy}benzamidine as white solid form.

¹H-NMR (DMSO-d₆) δvalue: 1.00-1.40(5H, m), 1.50-1.85(8H, m), 2.25-2.35(2H, m), 2.75-2.90(2H, m), 3.42(2H, t, J=6.2 Hz), 3.96(2H, t, J=6.5 Hz), 4.40-4.60(1H, broad), 5.60-5.80(2H, broad), 6.90(2H, d, J=8.8 Hz), 7.58(2H, d, J=8.8 Hz), 9.43 (1H, s).

REFERENCE EXAMPLE 23

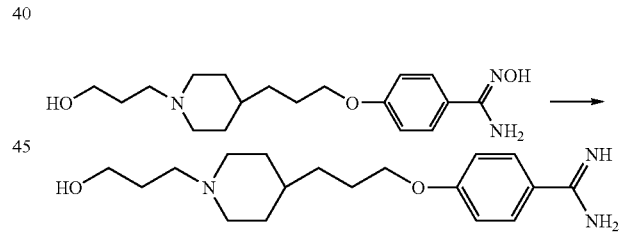

To an acetic acid (50 mL) suspension of 4.58 g of N'-hydroxy-4-{3-[1-(3-hydroxypropyl)-4-piperidinyl]propoxy}benzamidine was added 2.59 mL of acetic anhydride at room temperature, which was then stirred at the same temperature for one hour. To the reaction mixture was added 0.50 g of 5% palladium-carbon, which was then stirred at room temperature under hydrogen atmosphere for 5 hours and 30 minutes. Insoluble matter was filtered off, and the solvent was distilled off under reduced pressure. Water was added to the resultant residue, which was adjusted to pH 12.5 using a 5 mol/L sodium hydroxide aqueous solution. The precipitate was collected by filtration and washed with water to provide 4.82 g of 4-{3-[1-(3-hydroxypropyl)-4-piperidinyl]propoxy}benzamidine as white solid form.

¹H-NMR (DMSO-d₆) δvalue: 1.00-1.40(5H, m), 1.50-1.90(8H, m), 2.25-2.35(2H, m), 2.75-2.90(2H, m), 3.42(2H, t, J=6.2 Hz), 4.01(2H, t, J=6.5 Hz), 7.01(2H, d, J=8.8 Hz), 7.74(2H, d, J=8.8 Hz), 8.10-9.20(2H, broad).

REFERENCE EXAMPLE 24

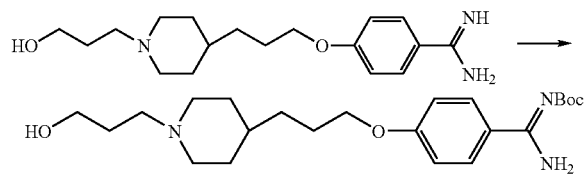

To a dioxane (10 mL) suspension of 2.00 g of 4-{3-[1-(3-hydroxypropyl)-4-piperidinyl]propoxy}benzamidine were added 2.05 g of di-tert-butyl=dicarbonate, 4 mL of N,N-dimethylformamide, and 10 mL of a 2.5 mol/L sodium hydroxide aqueous solution at room temperature, which was then stirred at the same temperature for 1 hour and 15 minutes. Subsequently, to the reaction mixture was added 10 mL of a 2.5 mol/L sodium hydroxide aqueous solution at room temperature, which was then stirred at the same temperature for 1 hour and 15 minutes. Chloroform and water were added to the reaction mixture. The organic layer was separated, and the aqueous layer was extracted with chloroform. The organic layer and the extract were combined, which was then washed with a saturated sodium chloride aqueous solution and further dried with anhydrous magnesium sulfate, followed by distilling off the solvent under reduced pressure. The resultant residue was purified using silica gel column chromatography (eluent; chloroform:methanol=4:1) to provide 1.75 g of tert-butyl=[1-amino-1-(4-{3-[1-(3-hydroxypropyl)-4-piperidinyl]propoxy}phenyl)methylidene]carbamate as white solid form.

$^1$H-NMR (CDCl$_3$). δvalue: 1.15-2.00(13H, m), 1.55(9H, s), 2.55-2.65(2H, m), 3.00-3.10(2H, m), 3.80(2H, t, J=5.2 Hz), 3.97(2H, t, J=6.5 Hz), 6.90(2H, d, J=8.9 Hz), 7.83(2H, d, J=8.9 Hz).

REFERENCE EXAMPLE 25

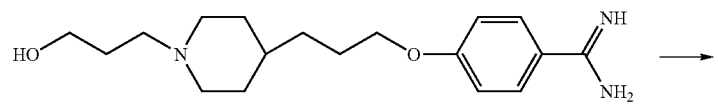

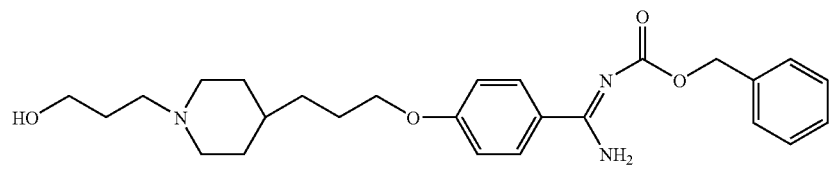

To an N,N-dimethylformamide (10 mL) suspension of 1.00 g of 4-{3-[1-(3-hydroxypropyl)-4-piperidinyl]propoxy}benzamidine was added 1.28 g of benzyl=4-nitrophenyl=carbonate at room temperature, which was then stirred at the same temperature for one hour. To the reaction mixture was added 1 mL of a 5 mol/L sodium hydroxide aqueous solution at room temperature, which was then stirred at the same temperature for 15 minutes. Thereto was added 5 mL of a 5 mol/L sodium hydroxide aqueous solution at room temperature, which was then stirred at the same temperature for 5 minutes. Chloroform and a 5% potassium carbonate aqueous solution were added to the reaction mixture. The organic layer was separated, washed sequentially with a 5% potassium carbonate aqueous solution and a saturated sodium chloride aqueous solution, and then dried with anhydrous magnesium sulfate, followed by distilling off the solvent under reduced pressure. The resultant residue was purified using silica gel column chromatography (eluent; chloroform:methanol=4:1) to provide 1.22 g of benzyl=[1-amino-1-(4-{3-[1-(3-hydroxypropyl)-4-piperidinyl]propoxy}phenyl)methylidene]carbamate as pale yellow solid form.

$^1$H-NMR (CDCl$_3$). δvalue: 1.15-1.45(5H, m), 1.75-2.00 (8H, m.), 2.55-2.65(2H, m), 3.00-3.10(2H, m), 3.75-3.85(2H, m), 3.98(2H, t, J=6.6 Hz), 5.21(2H, s), 6.91(2H, d, J=8.9 Hz),

REFERENCE EXAMPLE 26

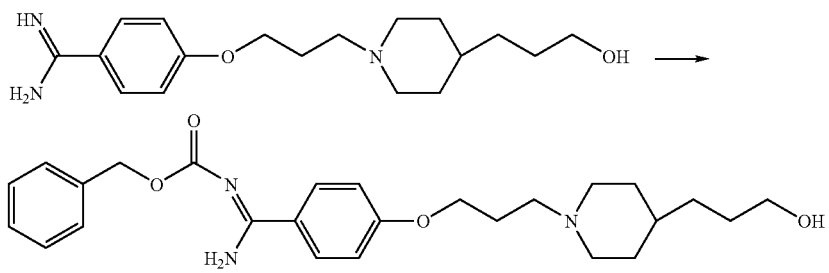

To an N,N-dimethylformamide (20 mL) solution of 1.00 g of 4-{3-[4-(3-hydroxypropyl)-1-piperidinyl]propoxy}benzamidine was added 2.14 g of benzyl=4-nitrophenyl=carbonate at room temperature, which was then stirred at the same temperature for 18 hours. Chloroform, water, and a 5% potassium carbonate aqueous solution were added to the reaction mixture. The organic layer was separated, washed sequentially with a 5% potassium carbonate aqueous solution and a saturated sodium chloride aqueous solution, and then dried with anhydrous magnesium sulfate, followed by distilling off the solvent under reduced pressure. The resultant residue was purified using silica gel column chromatography (eluent; chloroform:methanol=8:1) to provide 0.93 g of benzyl=[1-amino-1-(4-{3-[4-(3-hydroxypropyl)-1-piperidinyl]propoxy}phenyl)methylidene]carbamate as white solid form.

$^1$H-NMR (CDCl$_3$) . δvalue: 1.20-1.35(5H, m), 1.50-1.75 (4H, m), 1.85-2.05(4H, m), 2.45-2.55(2H, m), 2.85-3.00(2H, m), 3.62(2H, t, J=6.7 Hz), 4.04(2H, t, J=6.3 Hz), 5.21(2H, s), 6.88-6.93(2H, d, J=8.8 Hz), 7.25-7.50(5H, m), 7.84(2H, d, J=8.8 Hz).

EXAMPLE 1

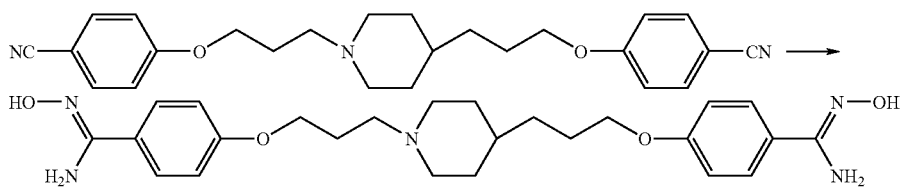

To a dimethylsulfoxide (126 mL) suspension of 12.6 g of 4-(3-{4-[3-(4-cyanophenoxy)propyl]-1-piperidinyl}propoxy)benzonitrile was added 19.1 mL of a 50% hydroxylamine aqueous solution, which was then stirred at 50° C. for 19 hours. The mixture was cooled down to room temperature, to which 260 mL of water was added dropwise over a period of 50 minutes, followed by stirring at room temperature for 30 minutes and then under cooling with water for 2 hours. The precipitate was collected by filtration to provide 15.0 g of 4-{3-[4-(3-{4-[amino(hydroxyimino)methyl]phenoxy}propyl)-1-piperidinyl]propoxy}-N'-hydroxybenzamidine as white solid form.

$^1$H-NMR (DMSO-d$_6$) . δvalue: 1.05-1.40(5H, m), 1.60-1.80(4H, m), 1.80-1.90(4H, m), 2.35-2.45(2H, m), 2.80-2.90 (2H, m), 3.96(2H, t, J=6.5 Hz), 4.01(2H, t, J=6.5 Hz), 5.65-5.75(4H, m), 6.85-6.95(4H, m), 7.55-7.65(4H, m), 9.43(1H, s), 9.43(1H, s).

EXAMPLE 2

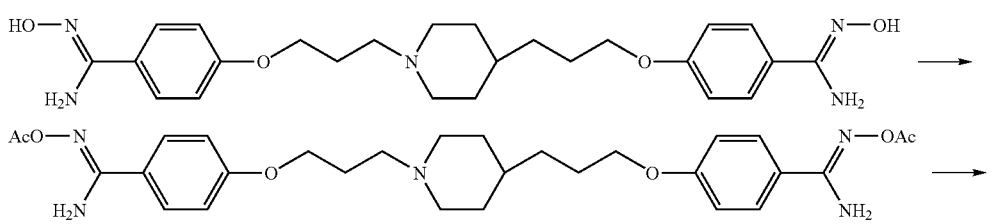

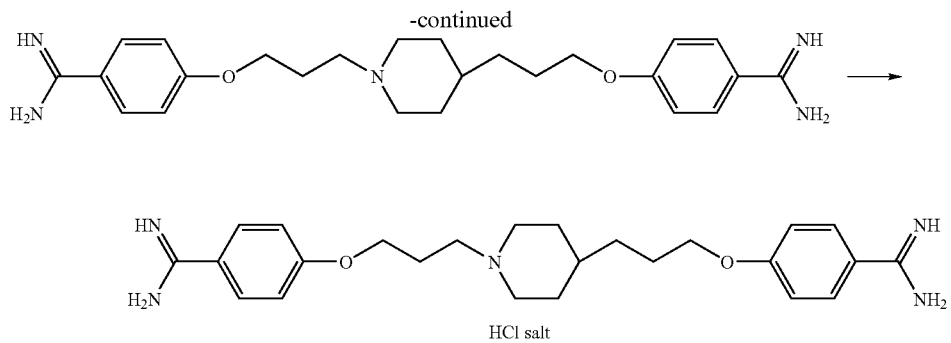

HCl salt (2-1)

To an acetic acid (10 mL) suspension of 1.07 g of 4-{3-[4-(3-{4-[amino(hydroxyimino)methyl]phenoxy}propyl)-1-piperidinyl]propoxy}-N'-hydroxybenzamidine was added 0.64 mL of acetic anhydride at room temperature, which was then stirred at room temperature for 40 minutes. To this mixture was added 0.10 g of 5% palladium-carbon, which was then stirred under hydrogen atmosphere for 2 hours and 15 minutes. Insoluble matter was filtered off before adding 4 mL of 6.0 mol/L hydrochloric acid, and insoluble matter was then filtered off, followed by distilling off the solvent under reduced pressure. A 5.0 mol/L sodium hydroxide aqueous solution was added to the resultant residue to adjust the pH to 12.5, followed by collecting the solid matter by filtration to provide 0.61 g of 4-{3-[4-(3-{4-[amino(imino)methyl]phenoxy}propyl)-1-piperidinyl]propoxy}benzamidine as white solid form.

(2-2)

To an acetic acid (150 mL) suspension of 14.9 g of 4-{3-[4-(3-{4-[amino(hydroxyimino)methyl]phenoxy}propyl)-1-piperidinyl]propoxy}-N'-hydroxybenzamidine was added 5.97 mL of acetic anhydride at room temperature, which was then stirred at room temperature for 1 hour and 20 minutes. To this mixture was added 1.50 g of 5% palladium-carbon, which was then stirred under hydrogen atmosphere for 4 hours and 40 minutes. Insoluble matter was filtered off, and 55 mL of 6.0 mol/L hydrochloric acid was then added. The solvent was distilled off under reduced pressure, and ethanol was added to the resultant residue. The solid matter was collected by filtration to provide 14.0 g of 4-{3-[4-(3-{4-[amino(imino)methyl]phenoxy}propyl)-1-piperidinyl]propoxy}benzamidine as white solid form.

$^1$H-NMR (DMSO-$d_6$) δvalue: 1.30-1.45(2H, m), 1.45-1.70(3H, m), 1.70-1.90(4H, m), 2.15-2.30(2H, m), 2.80-3.00 (2H, m), 3.10-3.20(2H, m), 3.45-3.55(2H, m), 4.10(2H, t, J=6.2 Hz), 4.19(2H, t, J=6.1 Hz), 7.15(2H, d, J=8.4 Hz), 7.16(2H, d, J=8.4 Hz), 7.84(2H, d, J=8.4 Hz), 7.86 (2H, d, J=8.4 Hz), 8.90-9.00(4H, m), 9.15-9.30(4H, m), 10.60-10.80 (1H, broad).

EXAMPLE 3

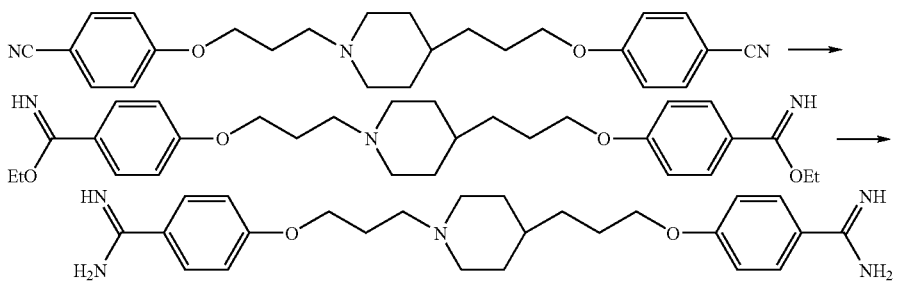

Hydrogen chloride was introduced into an ethanol (20 mL) suspension of 1.15 g of 4-(3-{4-[3-(4-cyanophenoxy)propyl]-1-piperidinyl}propoxy)benzonitrile under cooling with ice, which was then stirred at room temperature for 24 hours. The solvent was distilled off under reduced pressure, and the resultant residue was dissolved in 20 mL of ethanol. Thereto was added 1.54 g of ammonium acetate, which was then heated to reflux for 3 hours and 45 minutes. The reaction mixture was cooled down to room temperature, to which water was added, followed by distilling off ethanol under reduced pressure. Chloroform was added to the resultant residue, to which a 5.0 mol/L sodium hydroxide aqueous solution was then added to adjust the pH to 12.5. The precipitate was collected by filtration to provide 1.13 g of 4-{3-[4-(3-{4-[amino(imino)methyl]phenoxy}propyl)-1-piperidinyl]propoxy}benzamidine as white solid form.

$^1$H-NMR (DMSO-$d_6$) δvalue: 1.00-1.40(5H, m), 1.60-1.80(4H, m), 1.80-1.95(4H, m), 2.35-2.45(2H, m), 2.80-2.90 (2H, m), 3.98(2H, t, J=6.5 Hz), 4.03(2H, t, J=6.3 Hz), 6.30-7.20(4H, broad), 6.85-7.00(4H, m), 7.65-7.80(4H, m).

EXAMPLE 4

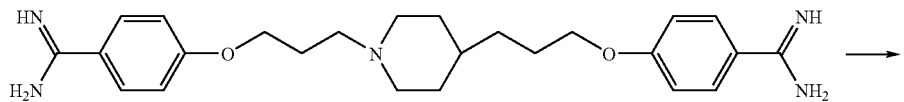

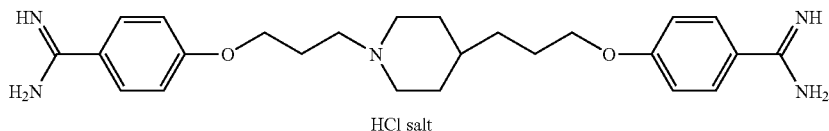
HCl salt

To an ethanol (10 mL) suspension of 0.50 g of 4-{3-[4-(3-{4-[amino(imino)methyl]phenoxy}propyl)-1-piperidinyl]propoxy}benzamidine was added 1.77 mL of a 2.6 mol/mL hydrogen chloride/ethanol solution at room temperature, which was then stirred at room temperature for 4 hours and 15 minutes. The precipitate was collected by filtration to provide 0.49 g of 4-{3-[4-(3-{4-[amino(imino)methyl]phenoxy}propyl)-1-piperidinyl]propoxy}benzamidine hydrochloride as colorless solid form.

$^1$H-NMR spectral data in DMSO-$d_6$ agreed with the values of EXAMPLE 2.

EXAMPLE 5

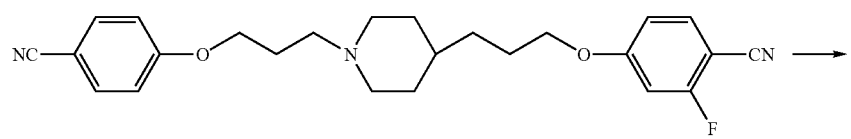

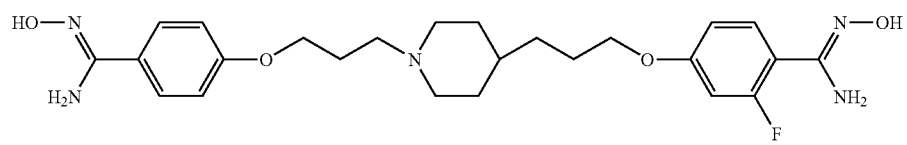

To a dioxane (3.0 mL) suspension of 67 mg of 4-(3-{1-[3-(4-cyanophenoxy)propyl]-4-piperidinyl}propoxy)-2-fluorobenzonitrile was added 1.0 mL of a 50% hydroxylamine aqueous solution, which was then heated to reflux for 2 hours. The mixture was cooled down to room temperature, to which 10 mL of water was then added dropwise, followed by stirring under cooling with ice for 30 minutes. The precipitate was collected by filtration to provide 63 mg of 4-{3-[1-(3-{4-[amino(hydroxyimino)methyl]phenoxy}propyl)-4-piperidinyl]propoxy}-2-fluoro-N'-hydroxybenzamidine as pale yellow solid form.

$^1$H-NMR (DMSO-$d_6$) $\delta$value: 1.00-1.40(5H, m), 1.60-1.80(4H, m), 1.80-1.95(4H, m), 2.35-2.45(2H, m), 2.80-2.90(2H, m), 3.98(2H, t, J=6.4 Hz), 4.00(2H, t, J=6.0 Hz), 5.60-5.80(4H, m), 6.70-6.85(2H, m), 6.90(2H, d, J=8.8 Hz), 7.35-7.45(1H, m), 7.58(2H, d, J=8.8 Hz), 9.43(1H, s), 9.50(1H, s).

EXAMPLE 6

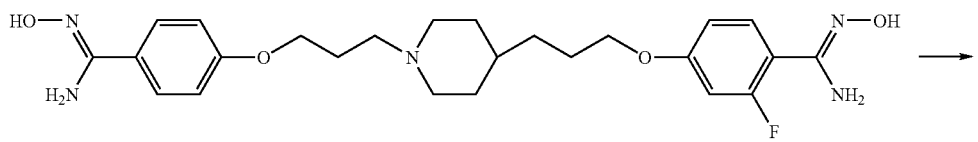

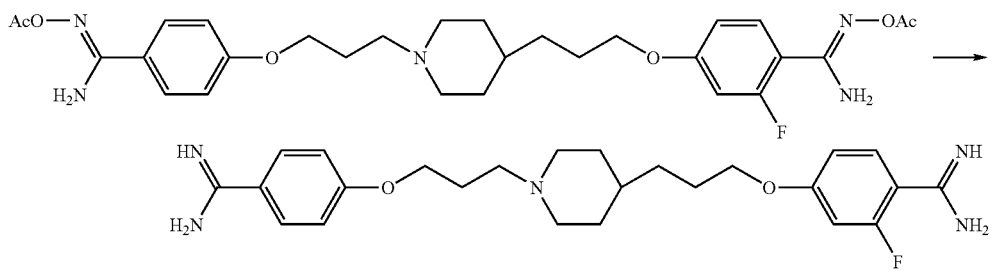

To an acetic acid (2.0 mL) suspension of 56 mg of 4-{3-[1-(3-{4-[amino(hydroxyimino)methyl]phenoxy}propyl)-4-piperidinyl]propoxy}-2-fluoro-N'-hydroxybenzamidine was added 0.043 mL of acetic anhydride at room temperature, which was then stirred at the same temperature for one hour. To this mixture was added 5.0 mg of 5% palladium-carbon, which was then stirred under hydrogen atmosphere for 2 hours. Insoluble matter was filtered off, and the solvent was distilled off under reduced pressure. Thereto were added 6.0 mol/L hydrochloric acid and water, followed by distilling off the solvent under reduced pressure. The resultant residue was purified using silica gel column chromatography (silica gel: ODS-1M120-S50 from YMC, eluent; water). The resultant residue was dissolved in 5.0 mL of water, to which a 5.0 mol/L sodium hydroxide aqueous solution was then added to adjust the pH to 12.2. The solution was stirred under cooling with ice for 20 minutes, and the precipitate was collected by filtration to provide 43 mg of 4-{3-[1-(3-{4-[amino(imino)methyl]phenoxy}propyl)-4-piperidinyl]propoxy}-2-fluorobenzamidine as white solid form.

$^1$H-NMR (DMSO-$d_6$) δvalue: 1.05-1.40(5H, m), 1.60-2.05(8H, m), 2.30-2.45(2H, m), 2.80-2.90(2H, m), 3.98(2H, t, J=6.5 Hz), 4.02(2H, t, J=6.3 Hz), 6.20-6.70(4H, broad), 6.75-6.85(2H, m), 6.92(2H, d, J=8.4 Hz), 7.45-7.55(1H, m), 7.71(2H, d, J=8.4 Hz).

EXAMPLE 7

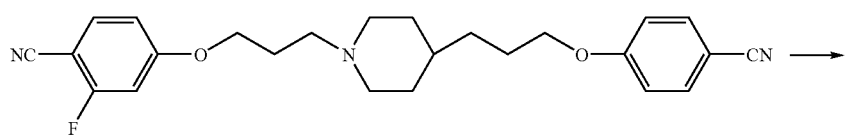

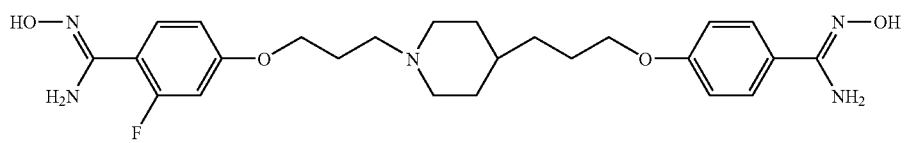

As described in Example 5, 0.10 g of 4-3-{4-[3-(4-cyanophenoxy)propyl]-1-piperidinyl}propoxy)-2-fluorobenzonitrile was used to provide 0.11 g of 4-{3-[4-(3-{4-[amino(hydroxyimino)methyl]phenoxy}propyl)-1-piperidinyl]propoxy}-2-fluoro-N'-hydroxybenzamidine as white solid form.

¹H-NMR (DMSO-d₆) δvalue: 1.00-1.40(5H, m), 1.60-1.75(4H, m), 1.75-1.90(4H, m), 2.30-2.40(2H, m), 2.80-2.90(2H, m), 3.96(2H, t, J=6.5 Hz), 4.03(2H, t, J=6.3 Hz), 5.65-5.80(4H, m), 6.75-6.90(2H, m), 6.90(2H, d, J=8.9 Hz), 7.35-7.45(1H, m), 7.58(2H, d, J=8.9 Hz), 9.43(1H, s), 9.50(1H, s).

EXAMPLE 8

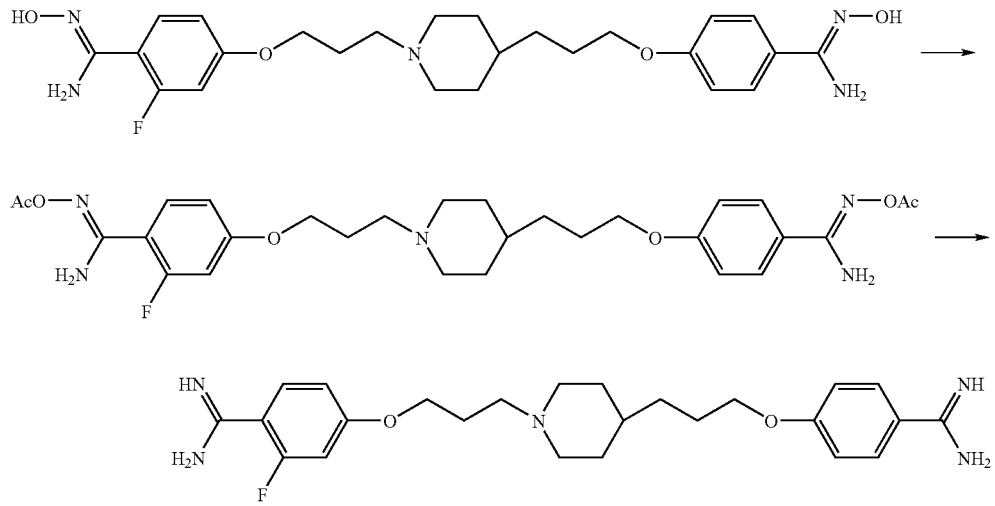

As described in Example 6, 90 mg of 4-{3-[4-(3-{4-[amino(hydroxyimino)methyl]phenoxy}propyl)-1-piperidinyl]propoxy}-2-fluoro-N'-hydroxybenzamidine was used to provide 34 mg of 4-{3-[4-(3-{4-[amino(imino)methyl]phenoxy}propyl)-1-piperidinyl]propoxy}-2-fluorobenzamidine as white solid form.

¹H-NMR (DMSO-d₆) δvalue: 1.05-1.40(5H, m), 1.60-1.90(8H, m), 2.30-2.45(2H, m), 2.80-20.90(2H, m), 3.98(2H, t, J=6.5 Hz), 4.03(2H, t, J=6.0 Hz), 6.30-6.75(4H, broad), 6.75-6.85(2H, m), 6.93(2H, d, J=8.7 Hz), 7.45-7.55(1H, m), 7.71(2H, d, J=8.7 Hz).

EXAMPLE 9

Hydrogen chloride was introduced into an ethanol (10 mL) suspension of 0.10 g of 4-(3-{1-[3-(4-cyano-3-fluorophenoxy)propyl]-4-piperidinyl}propoxy)-2-fluorobenzonitrile under cooling with ice, which was then stirred at the same temperature for 1 hour and 10 minutes and at room temperature for 17 hours. The solvent was distilled off under reduced pressure, and the resultant residue was suspended in 5.0 mL of ethanol, to which 44 mg of ammonium acetate was then added, followed by heating to reflux for 5 hours and 30 minutes. The solvent was distilled off under reduced pressure, and the resultant residue was dissolved in 8.0 mL of 1.0 mol/L hydrochloric acid, followed by distilling off the solvent under reduced pressure. The resultant residue was purified using silica gel column chromatography (silica gel: ODS-1M120-S50 from YMC, eluent; water) to provide 46 mg of 4-{3-[1-(3-{4-[amino(imino)methyl]-3-fluorophenoxy}propyl)-4-piperidinyl]propoxy}-2-fluorobenzamidine hydrochloride as white solid form.

¹H-NMR (DMSO-d₆) δvalue: 1.30-1.45(2H, m), 1.50-1.70(3H, m), 1.70-1.90(4H, m), 2.20-2.30(2H, m), 2.80-2.95

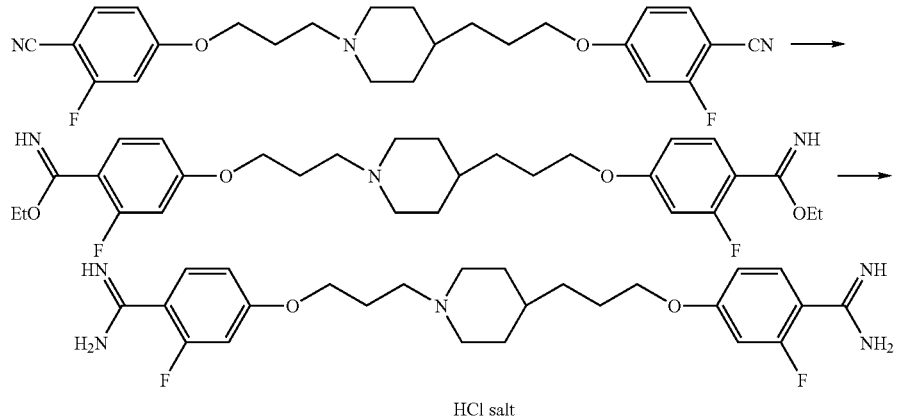

(2H, m), 3.10-3.20(2H, m), 3.40-3.55(2H, m), 4.10(2H, t, J=6.0 Hz), 4.20(2H, t, J=5.7 Hz), 6.95-7.05(2H, m), 7.05-7.15(2H, m), 7.60-7.75(2H, m), 9.20-9.50(8H, m), 10.95-11.10(1H, broad).

EXAMPLE 10

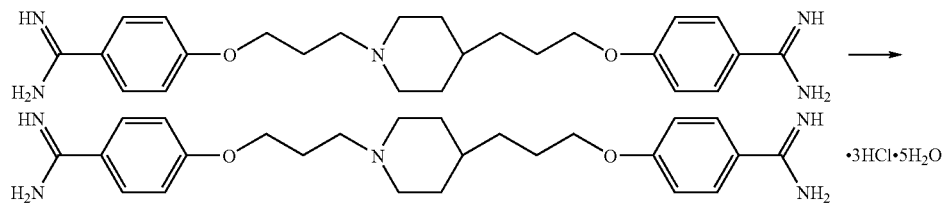

(10-1)

To a water (2.3 mL) suspension of 1.0 g of 4-{3-[4-(3-{4-[amino(imino)methyl]phenoxy}propyl)-1-piperidinyl]propoxy}benzamidine were added 0.72 g of hydrochloric acid, 6 mL of 2-propanol, and 0.5 mL of water at room temperature, which was then stirred at 40° C. Thereto was added 9 mL of 2-propanol, which was then stirred under cooling with ice for one hour. The precipitated crystals were collected by filtration to provide 1.4 g of 4-{3-[4-(3-{4-[amino(imino)methyl]phenoxy}propyl)-1-piperidinyl]propoxy}benzamidine trihydrochloride pentahydrate as colorless crystals. These crystals were used as seed crystals.

Water content: 14.5%

$^1$H-NMR spectral data in DMSO-$d_6$ agreed with the values of Example 2.

(10-2)

To a water (40 mL)/2-propanol (80 mL) suspension of 20.0 g of 4-{3-[4-(3-{4-[amino(imino)methyl]phenoxy}propyl)-1-piperidinyl]propoxy}benzamidine was added 14.3 g of hydrochloric acid, which was then stirred at 60° C. for 10 minutes. Thereto was added 120 mL of 2-propanol, to which 100 mg of seed crystals were added, followed by stirring at room temperature for 35 minutes and under cooling with ice for 2 hours. The precipitated crystals were collected by filtration to provide 28.3 g of 4-{3-[4-(3-{4-[amino(imino)methyl]phenoxy}propyl)-1-piperidinyl]propoxy}benzamidine trihydrochloride pentahydrate as colorless crystals.

Water content: 14.0%

Powder X-ray diffraction peaks (°): 6.6, 13.2, 16.1, 21.5, 25.5(2θ) (shown in FIG. 1)

$^1$H-NMR spectral data in DMSO-$d_6$ agreed with the values of Example 2.

EXAMPLE 11

As described in Example 10, 31.1 g of 4-{3-[4-(3-{4-[amino(imino)methyl]phenoxy}propyl)-1-piperidinyl]propoxy}benzamidine trimethanesulfonate dihydrate was obtained from 20.0 g of 4-{3-[4-(3-{4-[amino(imino)methyl]phenoxy}propyl)-1-piperidinyl]propoxy}benzamidine and 13.6 g of methanesulfonic acid.

Water content: 4.6%

$^1$H-NMR (DMSO-$d_6$) δvalue: 1.36-1.79(7H, m), 1.86-1.96(2H, m), 2.15-2.25(2H, m), 2.34(9H, s), 2.85-2.98(2H, m), 3.18-3.26(2H, m), 3.50-3.58(2H, m), 4.09(2H, t, J=6.3 Hz), 4.16(2H, t, J=5.9 Hz), 7.15(2H, d, J=8.8 Hz), 7.16(2H, d, J=9.0 Hz), 7.82(2H, d, J=8.5 Hz), 7.84 (2H, d, J=8.3 Hz), 8.77-8.87(3H, m), 9.10-9.18(3H, m).

EXAMPLE 12

As described in Example 10, 21.6 g of 4-{3-[4-(3-{4-[amino(imino)methyl]phenoxy}propyl)-1-piperidinyl]propoxy}benzamidine diacetate 1/2-hydrate was obtained from 20.0 g of 4-{3-[4-(3-{4-[amino(imino)methyl]phenoxy}propyl)-1-piperidinyl]propoxy}benzamidine and 8.5 g of acetic acid.

Water content: 1.4%

$^1$H-NMR (DMSO-$d_6$) δvalue: 1.10-1.40(5H, m), 1.62-1.80(6H, m), 1.75(6H, s), 2.40-2.47(2H, m), 2.50-2.60(2H, m), 2.84-2.92(2H, m), 4.00-4.15(4H, m), 7.10-7.15(4H, m), 7.78(4H, d, J=8.8 Hz).

EXAMPLE 13

As described in Example 10, 30.3 g of 4-{3-[4-(3-{4-[amino(imino)methyl]phenoxy}propyl)-1-piperidinyl]propoxy}benzamidine 3/2-sulfate trihydrate was obtained from 20.0 g of 4-{3-[4-(3-{4-[amino(imino)methyl]phenoxy}propyl)-1-piperidinyl]propoxy}benzamidine and 15.1 g of sulfuric acid.

Water content: 7.7%

$^1$H-NMR (DMSO-$d_6$) δvalue: 1.40-1.90(7H, m), 2.02-2.10(2H, m), 2.24-2.33(2H, m), 2.94-3.04(2H, m), 3.30-3.36 (2H, m), 3.62-3.69(2H, m), 4.17(2H, t, J=6.3 Hz), 4.25(2H, t, J=5.7 Hz), 7.14-7.16(4H, m), 7.78(2H, d, J=9.0 Hz), 7.78(2H, d, J=9.0 Hz).

EXAMPLE 14

As described in Example 10, 25.0 g of 4-{3-[4-(3-{4-[amino(imino)methyl]phenoxy}propyl)-1-piperidinyl]propoxy}benzamidine triphosphate dihydrate was obtained from 20.0 g of 4-{3-[4-(3-{4-[amino(imino)methyl]phenoxy}propyl)-1-piperidinyl]propoxy}benzamidine and 16.9 g of phosphoric acid.

Water content: 4.2%

$^1$H-NMR (DMSO-$d_6$) δvalue: 1.43-1.76(5H, m), 1.84-1.94(2H, m), 2.05-2.12(2H, m), 2.27-2.33(2H, m), 2.96-3.06 (2H, m), 3.32-3.38(2H, m), 3.64-3.70(2H, m), 4.19(2H, t, J=6.2 Hz), 4.27(2H, t, J=5.6 Hz), 7.17(4H, d, J=8.8 Hz), 7.80(2H, d, J=9.0 Hz), 7.80(2H, d, J=9.0 Hz).

EXAMPLE 15

As described in Example 10, 26.5 g of 4-{3-[4-(3-{4-[amino(imino)methyl]phenoxy}propyl)-1-piperidinyl]propoxy}benzamidine di-L-lactate 3/2-hydrate was obtained from 20.0 g of 4-{3-[4-(3-{4-[amino(imino)methyl]phenoxy}propyl)-1-piperidinyl]propoxy}benzamidine and 15.5 g of L-lactic acid.

Water content: 4.1%

$^1$H-NMR (DMSO-$d_6$) δvalue: 1.33-1.35(6H, m), 1.40-1.70(5H, m), 1.84-1.90(2H, m), 1.99-2.07(2H, m), 2.22-2.29(2H, m), 2.86-2.92(2H, m), 3.21-3.25(2H, m), 3.50-3.56(2H, m), 4.09-4.14(2H, m), 4.19(2H, t, J=6.5 Hz), 4.26(2H, t, J=5.7 Hz), 7.15-7.19(4H, m), 7.80(2H, d, J=9.0 Hz), 7.80(2H, d, J=8.3 Hz).

EXAMPLE 16

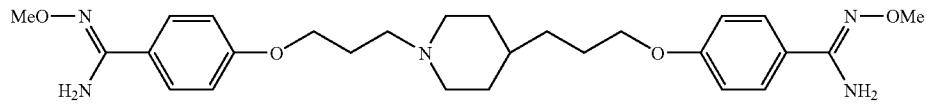

Hydrogen chloride was introduced into an ethanol (20 mL) suspension of 1.00 g of 4-(3-{4-[3-(4-cyanophenoxy)propyl]-1-piperidinyl}propoxy)benzonitrile under cooling with ice, which was then stirred for 18 hours. The solvent was distilled off under reduced pressure, and the resultant residue was dissolved in 60 mL of ethanol. To this solution was added 2.07 g of O-methylhydroxylamine hydrochloride, to which 10.4 mL of triethylamine was then dropwise added under cooling with ice over a period of 2 minutes. After stirring at room temperature for 18 hours, the reaction mixture was added to a mixture of water and chloroform, which was then adjusted to pH 10 using a 1.0 mol/L sodium hydroxide aqueous solution. The organic layer was separated, washed with water, and then dried with anhydrous sodium sulfate, followed by distilling off the solvent under reduced pressure. The resultant residue was purified using silica gel column chromatography (eluent; chloroform:methanol=30:1), to which ethanol was then added, followed by collecting the solid by filtration to provide 0.99 g of 4-{3-[4-(3-{4-[amino(methoxyimino)methyl]phenoxy}propyl)-1-piperidinyl]propoxy}benzamide=O-methyloxime as white solid form.

$^1$H-NMR (CDCl$_3$) δvalue: 1.20-1.45(5H, m), 1.65-1.84(4H, m), 1.88-2.04(4H, m), 2.45-2.55(2H, m), 2.90-2.98(2H, m), 3.90(6H, s), 3.96(2H, t, J=6.6 Hz), 4.02(2H, t, J=6.4 Hz), 4.74(4H, s), 6.88(2H, d, J=8.8 Hz), 6.90(2H, d, J=8.8 Hz), 7.55 (2H, d, J=8.8 Hz), 7.55(2H, d, J=8.8 Hz).

EXAMPLE 17

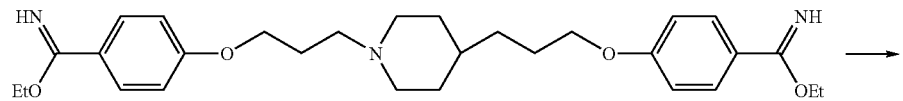

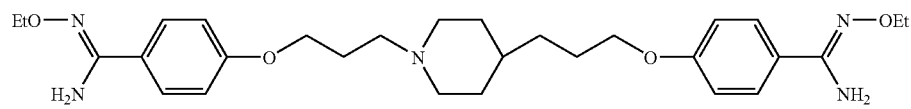

To an ethanol (8 mL) suspension of 0.20 g of ethyl=4-{3-[4-(3-{4-[ethoxy(imino)methyl]phenoxy}propyl)-1-piperidinyl]propoxy}benzimidate were sequentially added 0.39 g of O-ethylhydroxylamine hydrochloride and 0.84 mL of triethylamine under cooling with ice, which was then stirred at room temperature for 3.5 days. The reaction mixture was added to a mixture of chloroform and water, which was then adjusted to pH 9.7 using a 20% sodium hydroxide aqueous solution. The organic layer was separated, washed with water, and then dried with anhydrous sodium sulfate, followed by distilling off the solvent under reduced pressure. The resultant residue was purified using silica gel column chromatography (eluent; chloroform:ethanol=20:1) to provide 0.20 g of 4-{3-[4-(3-{4-[amino(ethoxyimino)methyl]phenoxy}propyl)-1-piperidinyl]propoxy}benzamide=O-ethyloxime as white solid form.

$^1$H-NMR (CDCl$_3$) δvalue: 1.20-1.45(5H, m), 1.32(3H, t, J=7.0 Hz), 1.32(3H, t, J=7.0 Hz), 1.65-1.85(4H, m), 1.85-2.05(4H, m), 2.45-2.52(2H, m), 2.90-3.00(2H, m), 3.96(2H, t, J=6.6 Hz), 4.02(2H, t, J=6.3 Hz), 4.14(2H, q, J=7.0 Hz), 4.14(2H, q, J=7.0 Hz), 4.74(4H, s), 6.88(2H, d, J=8.8 Hz), 6.89(2H, d, J=8.8 Hz), 7.55(2H, d, J=8.8 Hz), 7.55(2H, d, J=8.8 Hz).

EXAMPLE 18 of triethylamine at room temperature, which was then stirred at the same temperature for one week. Chloroform and water were added to the reaction solution. The organic layer was separated, washed with a saturated sodium chloride aqueous solution, and then dried with anhydrous magnesium sulfate, followed by distilling off the solvent under reduced pressure. The resultant residue was purified using silica gel column chromatography (eluent; chloroform:ethanol=30:1), to which hexane was then added, followed by collecting the solid by filtration to provide 0.12 g of 4-{3-[4-(3-{4-[amino(2,2,2-trifluoroethoxyimino)methyl]phenoxy}propyl)-1-piperidinyl]propoxy}benzamide=O-(2,2,2-trifluoroethyl)oxime as white solid form.

$^1$H-NMR (CDCl$_3$) δvalue: 1.20-1.45(5H, m), 1.65-2.05(8H, m), 2.45-2.55(2H, m), 2.90-3.00(2H, m), 3.96(2H, t, J=6.6 Hz), 4.03(2H, t, J=6.2 Hz), 4.43(2H, q, J=8.6 Hz),

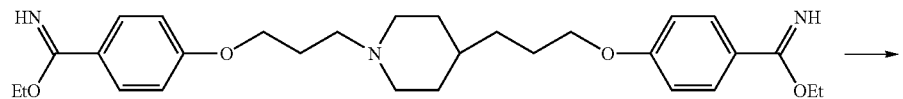

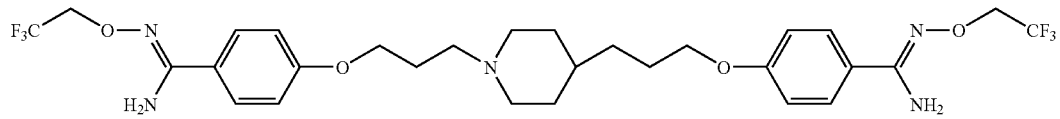

To an ethanol (6 mL) suspension of 0.20 g of ethyl=4-{3-[4-(3-{4-[ethoxy(imino)methyl]phenoxy}propyl)-1-piperidinyl]propoxy}benzimidate were added 0.61 g of O-(2,2,2-trifluoroethyl)hydroxylamine hydrochloride and 0.84 mL 4.43(2H, q, J=8.6 Hz), 4.82(4H, s), 6.89(2H, d, J=8.8 Hz), 6.90(2H, d, J=8.8 Hz), 7.54(2H, d, J=8.8 Hz), 7.54(2H, d, J=8.8 Hz).

EXAMPLE 19

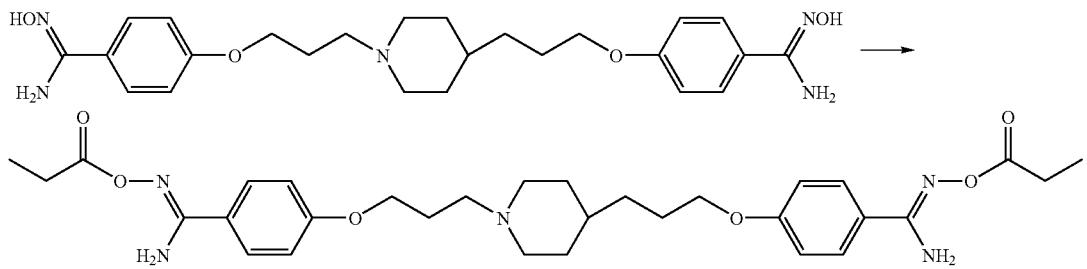

To an N-methyl-2-pyrrolidone (10 mL) solution of 0.35 g of propionic acid was added 0.76 g of 1,1'-carbonyldiimidazole at room temperature, which was then stirred at the same temperature for one hour. An N-methyl-2-pyrrolidone (10 mL) solution of 1.00 g of 4-{3-[4-(3-{4-[amino(hydroxyimino)methyl]phenoxy}propyl)-1-piperidinyl]propoxy}benzamide=oxime was added to the mixture at room temperature, which was then stirred for 15 hours. The reaction mixture was added to a mixture of chloroform and water. The precipitate was collected by filtration and washed with ethyl acetate to provide 0.58 g of 4-{3-[4-(3-{4-[amino(propionyloxyimino)methyl]phenoxy}propyl)-1-piperidinyl]propoxy}benzamide=O-(propionyl)oxime as white solid form.

$^1$H-NMR (DMSO-$d_6$) . δvalue: 1.08(3H, t, J=7.6 Hz), 1.08 (3H, t, J=7.6 Hz), 1.10-1.40(5H, m), 1.60-1.80(4H, m), 1.80-1.95(4H, m), 2.35-2.45(2H, m), 2.45(2H, q, J=7.6 Hz), 2.45 (2H, q, J=7.6 Hz), 2.80-2.90(2H, m), 3.99(2H, t, J=6.5 Hz), 4.04(2H, t, J=6.3 Hz), 6.65(4H, s), 6.95-7.00(4H, m), 7.60-7.70(4H, m).

EXAMPLE 20

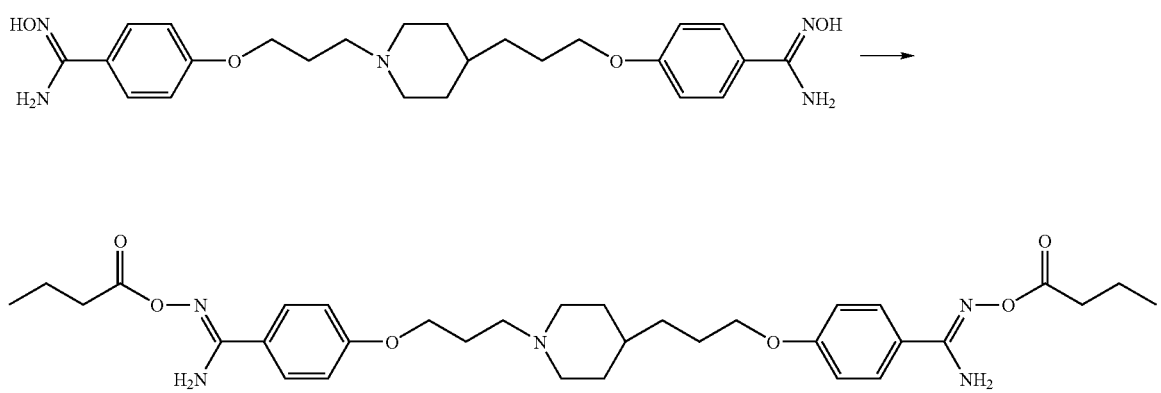

To an N-methyl-2-pyrrolidone (10 mL) solution of 0.42 g of butyric acid was added 0.76 g of 1,1'-carbonyldiimidazole at room temperature, which was then stirred at the same temperature for one hour. An N-methyl-2-pyrrolidone (10 mL) solution of 1.00 g of 4-{3-[4-(3-{4-[amino(hydroxyimino)methyl]phenoxy}propyl)-1-piperidinyl]propoxy}benzamide=oxime was added to the mixture at room temperature, which was then stirred at the same temperature for 14 hours. The reaction mixture was added to a mixture of ethyl acetate and water. The precipitate was collected by filtration and washed with ethyl acetate to provide 1.10 g of 4-{3-[4-(3-{4-[amino(n-butyloxyimino)methyl]phenoxy}propyl)-1-piperidinyl]propoxy}benzamide=O-(butyryl)oxime as white solid form.

$^1$H-NMR (DMSO-$d_6$) . δvalue: 0.92(3H, t, J=7.4 Hz), 0.92 (3H, t, J=7.4 Hz), 1.05-1.40(5H, m), 1.55-1.90(12H, m), 2.35-2.45(2H, m), 2.42(2H, t, J=7.3 Hz), 2.42(2H, t, J=7.3 Hz), 2.80-2.90(2H, m), 3.99(2H, t, J=6.5 Hz), 4.04(2H, t, J=6.5 Hz), 6.64(4H, s), 6.95-7.00(4H, m), 7.63-7.66(4H, m).

EXAMPLE 21

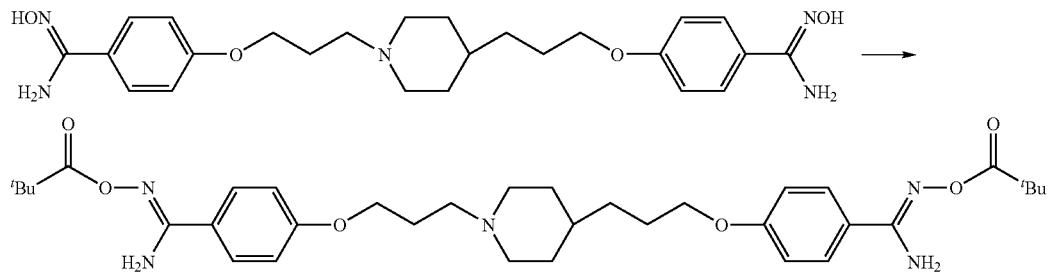

To an N-methyl-2-pyrrolidone (10 mL) solution of 0.47 g of pivalic acid was added 0.76 g of 1,1'-carbonyldiimidazole at room temperature, which was then stirred at the same temperature for 1 hour and 20 minutes. An N-methyl-2-pyrrolidone (10 mL) solution of 1.00 g of 4-{3-[4-(3-{4-[amino(hydroxyimino)methyl]phenoxy}propyl)-1-piperidinyl]propoxy}benzamide=oxime was added to the mixture at room temperature, which was then stirred at the same temperature for 2 hours. The reaction mixture was added a mixture of ethyl acetate and water. The precipitate was collected by filtration and washed with ethyl acetate to provide 0.81 g of 4-{3-[4-(3-{4-[amino(2,2-dimethylpropionyloxyimino)methyl]phenoxy}propyl)-1-piperidinyl]propoxy}benzamide=O-(2,2-dimethylpropionyl)oxime as white solid form.

$^1$H-NMR (CDCl$_3$) δvalue: 1.20-1.45(5H, m), 1.34(9H, s), 1.34(9H, s), 1.65-1.85(4H, m), 1.85-2.05(4H, m), 2.45-2.55(2H, m), 2.90-3.00(2H, m), 3.97(2H, t, J=6.5 Hz), 4.04 (2H, t, J=6.5 Hz), 4.92(4H, s), 6.90(2H, d, J=8.8 Hz), 6.91 (2H, d, J=8.8 Hz), 7.64(2H, d, J=8.8 Hz), 7.64(2H, d, J=8.8 Hz).

separated and dried with anhydrous magnesium sulfate, followed by distilling off the solvent under reduced pressure. Ethyl acetate and water were added to the resultant residue. The organic layer was separated, washed with water, and then dried with anhydrous magnesium sulfate, followed by distilling off the solvent under reduced pressure. The resultant residue was suspended in diisopropyl ether, and the solid matter was collected by filtration and washed with ethyl acetate and diisopropyl ether to provide 0.24 g of 4-(3-{4-[3-(4-{amino[(4-methoxy-4-oxobutylyl)oxyimino]methyl}phenoxy)propyl]-1-piperidinyl}propoxy)benzamide=O-[(4-methoxy-4-oxo)butylyl]oxime as white solid form.

$^1$H-NMR (CDCl$_3$) δvalue: 1.20-1.45(5H, m), 1.65-2.05 (8H, m), 2.45-2.55(2H, m), 2.70-2.80(4H, m), 2.80-2.90(4H,

EXAMPLE 22

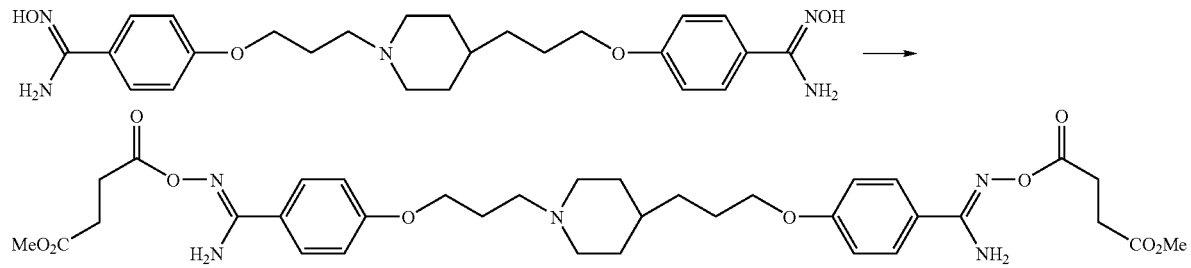

To an N-methyl-2-pyrrolidone (5 mL) solution of 0.42 g of methyl=hydrogen=succinate was added 0.52 g of 1,1'-carbonyldiimidazole at room temperature, which was then stirred at the same temperature for 2 hours. An N-methyl-2-pyrrolidone (10 mL) solution of 0.50 g of 4-{3-[4-(3-{4-[amino(hydroxyimino)methyl]phenoxy}propyl)-1-piperidinyl]propoxy}benzamide=oxime was added to the mixture at room temperature, which was then stirred at the same temperature for 3 hours. The reaction mixture was added to a mixture of ethyl acetate and water. Insoluble matter was filtered off, followed by adjustment to pH 7.0 using a 5 mol/L sodium hydroxide aqueous solution before adding a saturated sodium chloride aqueous solution. The organic layer was m), 2.90-3.00(2H, m), 3.71(3H, s), 3.71(3H, s), 3.97(2H, t, J=6.6 Hz), 4.04 (2H, t, J=6.3 Hz), 5.00-5.20(4H, broad), 6.90(2H, d, J=8.7 Hz), 6.91(2H, d, J=8.7 Hz), 7.63 (2H, d, J=8.7 Hz), 7.63(2H, d, J=8.7 Hz).

EXAMPLE 23

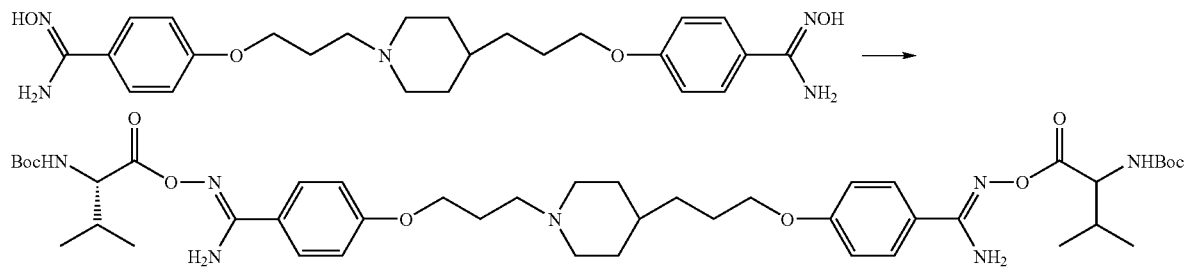

To an N-methyl-2-pyrrolidone (4 mL) solution of 0.23 g of N-(tert-butoxycarbonyl)-L-valine was added 0.18 g of 1,1'-carbonyldiimidazole at room temperature, which was then stirred at the same temperature for 3 hours. An N-methyl-2-pyrrolidone (6 mL) solution of 0.25 g of 4-{3-[4-(3-{4-[amino(hydroxyimino)methyl]phenoxy}propyl)-1-piperidinyl]propoxy}benzamide=oxime was added to the mixture at room temperature, which was then stirred at the same temperature for 18 hours. The reaction mixture was added to a mixture of ethyl acetate and water. The organic layer was separated, washed with a saturated sodium chloride aqueous solution, and then dried with anhydrous magnesium sulfate, followed by distilling off the solvent under reduced pressure. The resultant residue was suspended in diisopropyl ether, and the solid matter was collected by filtration and purified using silica gel column chromatography (eluent; chloroform:methanol=20:1) to provide 0.27 g of 4-(3-{4-[3-(4-{amino[(2S)-2-(tert-butoxycarbonyl)amino-3-methylbutylyloxyimino]methyl}phenoxy)propyl]-1-piperidinyl}propoxy)benzamide=O-[(2S)-2 (tert-butoxycarbonyl)amino-3-methylbutylyl]oxime as white solid form.

$^1$H-NMR (DMSO-$d_6$) δvalue: 0.90(6H, d, J=6.8 Hz), 0.90(6H, d, J=6.8 Hz), 1.05-1.45(5H, m), 1.41(9H, s), 1.41 (9H, s), 1.60-1.95(8H, m), 2.00-2.10(2H, m), 2.35-2.45(2H, m), 2.80-2.90(2H, m), 3.95-4.10(6H, m), 6.65-6.85(4H, broad), 6.97-7.00(4H, m), 7.30-7.40(2H, broad), 7.60-7.70 (4H, m).

EXAMPLE 24

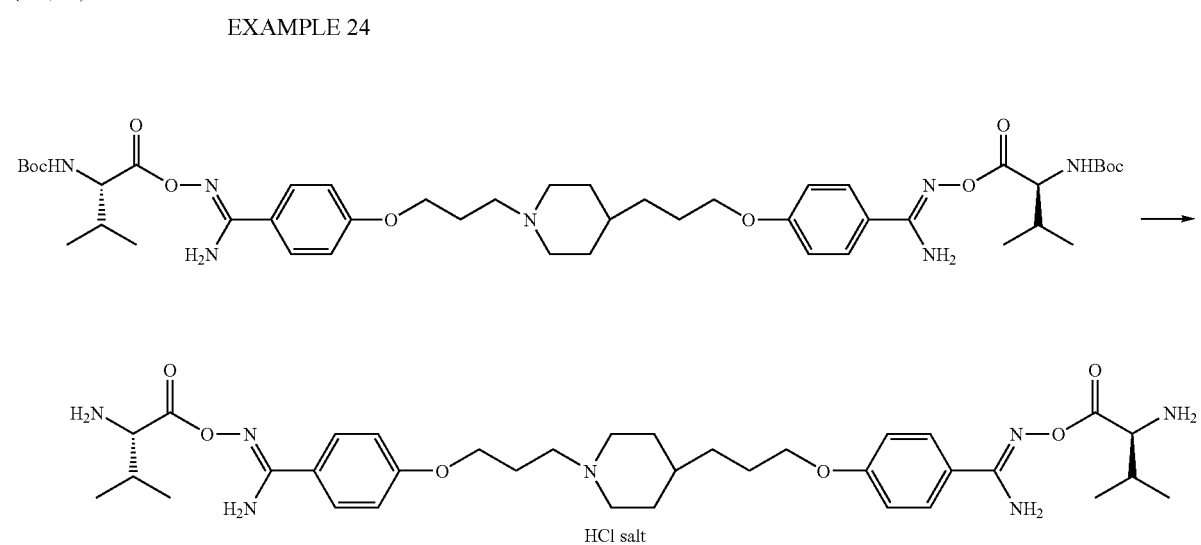

To an ethanol (2 mL) solution of 0.10 g of 4-(3-{4-[3-(4-{amino[(2S)-2-(tert-butoxycarbonyl)amino-3-methylbutylyloxyimino]methyl}phenoxy)propyl]-1-piperidinyl}propoxy)benzamide=O-[(2S)-2-(tert-butoxycarbonyl)amino-3-methylbutylyl]oxime was added 5 mL of 2.9 mol/L hydrogen chloride/ethanol at room temperature, which was then stirred at the same temperature for 18 hours and 30 minutes. Thereto was added 1 mL of 2.9 mol/L hydrogen chloride/ethanol, which was then stirred for 30 minutes. The solvent was distilled off under reduced pressure, and the resultant residue was suspended in diisopropyl ether, followed by collecting the solid matter by filtration before washing with diisopropyl ether to provide 80 mg of 4-{3-[4-(3-{4-[amino((2S)-2-amino-3-methylbutylyloxyimino)methyl]phenoxy}propyl)-1-piperidinyl]propoxy}benzamide=O-((2S)-2-amino-3-methylbutylyl)oxime hydrochloride as pale yellow solid form.

$^1$H-NMR (DMSO-$d_6$) δvalue: 1.00-1.07(12H, m), 1.30-1.95(9H, m), 2.10-2.35(4H, m), 2.30-2.50(2H, m), 2.80-3.00 (2H, m), 3.10-3.25(2H, m), 3.90-4.15(6H, m), 6.90-7.20(8H, m), 7.65-7.75(4H, m), 8.60-8.80(4H, broad).

EXAMPLE 25

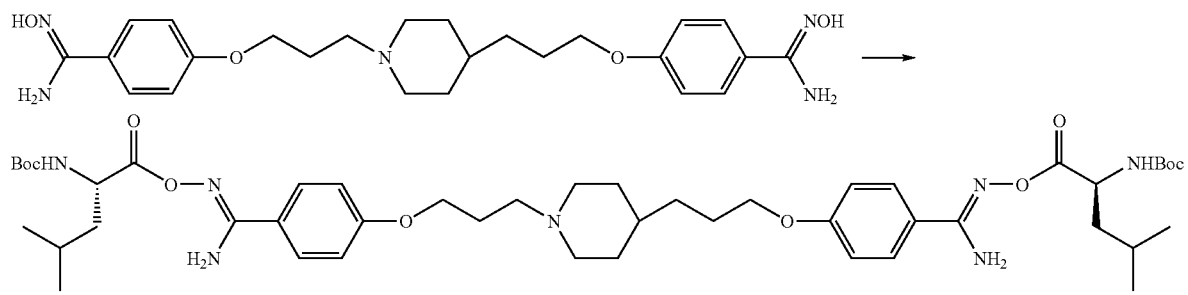

To an N-methyl-2-pyrrolidone (5 mL) solution of 0.23 g of N-(tert-butoxycarbonyl)-L-leucine monohydrate was added 0.34 g of 1,1'-carbonyldiimidazole at room temperature, which was then stirred at the same temperature for 1 hour and 30 minutes. An N-methyl-2-pyrrolidone (5 mL) solution of 0.20 g of 4-{3-[4-(3-{4-[amino(hydroxyimino)methyl]phenoxy}propyl)-1-piperidinyl]propoxy}benzamide=oxime was added to the mixture at room temperature, which was then stirred at the same temperature for 5 hours. The reaction mixture was added to a mixture of ethyl acetate and water. The organic layer was separated, washed with a saturated sodium chloride aqueous solution, and then dried with anhydrous magnesium sulfate, followed by distilling off the solvent under reduced pressure. The resultant residue was purified using silica gel column chromatography (eluent; chloroform:methanol=10:1) to provide 0.14 g of 4-(3-{4-[3-(4-{amino[(2S)-2-(tert-butoxycarbonyl)amino-4-methyl-pentanoyloxyimino]methyl}phenoxy)propyl]-1-piperidinyl}propoxy)benzamide=O-[(2S)-2 (tert-butoxycarbonyl)amino-4-methylpentanoyl]oxime as white solid form.

$^1$H-NMR (CDCl$_3$) .δvalue: 0.97(3H, d, J=5.9 Hz), 0.97 (3H, d, J=5.9 Hz), 0.99(3H, d, J=6.1 Hz), 0.99(3H, d, J=6.1 Hz), 1.25-1.90(15H, m), 1.45(9H, s), 1.45(9H, s), 1.95-2.15 (4H, m), 2.55-2.65(2H, m), 3.00-3.10(2H, m), 3.97(2H, t, J=6.3 Hz), 4.04(2H, t, J=6.3 Hz), 4.40-4.50(2H, m), 4.95-5.05(2H, m), 5.15-5.35(4H, broad), 6.88-6.91(4H, m), 7.63 (4H, d, J=8.4 Hz).

Example 26

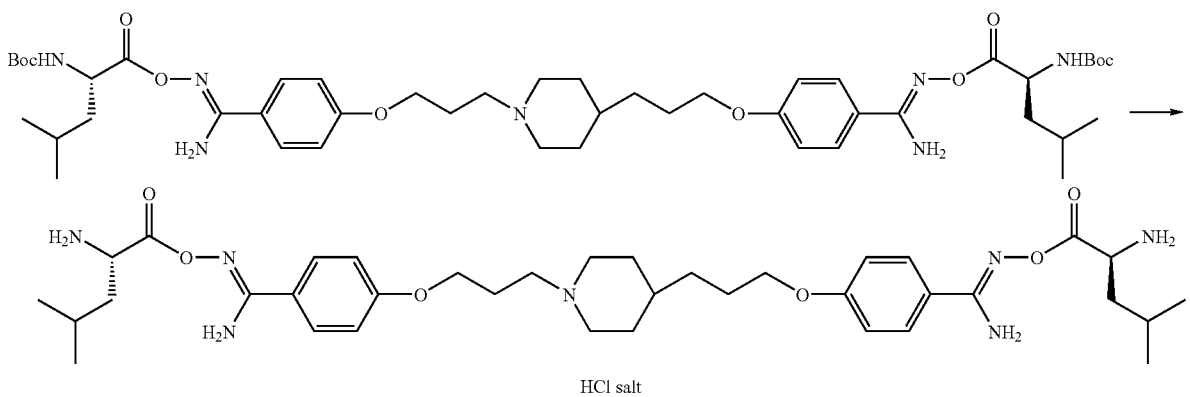

HCl salt

To a chloroform (5.0 mL) solution of 0.10 g of 4-(3-{4-[3-(4-{amino[(2S)-2-(tert-butoxycarbonyl)amino-4-methyl-pentanoyloxyimino]methyl}phenoxy)propyl]-1-piperidinyl}propoxy)benzamide=O-[(2S)-2-(tert-butoxycarbonyl)amino-4-methylpentanoyl]oxime was added 20 µL of trifluoroacetic acid under cooling with ice, which was then stirred at room temperature for 2 hours and 10 minutes. To the reaction mixture was added 0.1 mL of trifluoroacetic acid, which was then stirred for 21 hours. Thereto was further added 1 mL of trifluoroacetic acid, which was then stirred for 3 hours. The solvent was distilled off under reduced pressure, and 2.9 mol/L hydrogen chloride/ethanol was added, followed by distilling off the solvent under reduced pressure. The resultant solid was suspended in diisopropyl ether, followed by collecting solid matter by filtration before washing with diisopropyl ether to provide 0.04 g of 4-{3-[4-(3-{4-[amino((2S)-2-amino-4-methylpentanoyloxy)imino]methyl}phenoxy)propyl]-1-piperidinyl]propoxy}benzamide=O-((2S)-2-amino-4-methylpentanoyl) oxime hydrochloride as white solid form.

$^1$H-NMR (DMSO-d$_6$) .δvalue: 0.90(3H, d, J=6.6 Hz), 0.90(3H, d, J=6.6 Hz), 0.91(3H, d, J=6.3 Hz), 0.91(3H, d, J=6.3 Hz), 1.30-1.45(2H, m), 1.50-1.95(15H, m), 2.20-2.30 (2H, m), 2.80-2.95(2H, m), 3.10-3.20(2H, m), 3.75-4.30(6H, m), 7.10-7.20(4H, m), 7.65-7.80(4H, m), 8.25-8.40(2H, broad), 8.40-8.60(4H, broad), 11.05-11.20(2H, broad).

Example 27

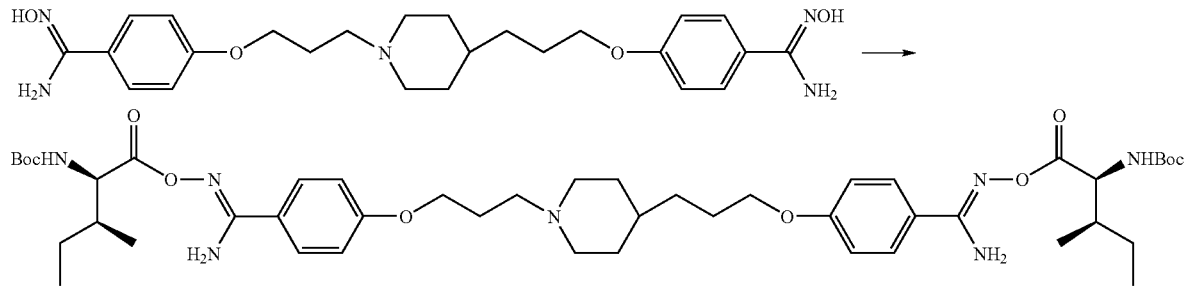

To an N-methyl-2-pyrrolidone (10 mL) solution of 0.65 g of N-(tert-butoxycarbonyl)-L-isoleucine ½-hydrate was added 1.14 g of 1,1'-carbonyldiimidazole at room temperature, which was then stirred at the same temperature for 1 hour and 30 minutes. An N-methyl-2-pyrrolidone (15 mL) solution of 1.00 g of 4-{3-[4-(3-{4-[amino(hydroxyimino)methyl]phenoxy}propyl)-1-piperidinyl]propoxy}benzamide=oxime was added to the mixture at room temperature, which was then stirred at the same temperature for 2 days. The reaction mixture was added to a mixture of ethyl acetate and water, and insoluble matter was filtered off. The organic layer was separated, washed with water, and then dried with anhydrous magnesium sulfate, followed by distilling off the solvent under reduced pressure. The resultant residue was purified using silica gel column chromatography (eluent; chloroform:methanol=30:1), and the resultant solid was suspended in diisopropyl ether, followed by collecting the solid matter by filtration before washing with diisopropyl ether to provide 0.38 g of 4-(3-{4-[3-(4-{amino[(2S,3S)-2-(tert-butoxycarbonyl)amino-3-methylpentanoyloxyimino]methyl}phenoxy)propyl]-1-piperidinyl}propoxy)benzamide=O-[(2S,3S)-2-(tert-butoxycarbonyl)amino-3-methylpentanoyl]oxime as white solid form.

$^1$H-NMR (CDCl$_3$) .δvalue: 0.95(3H, t, J=7.4 Hz), 0.95 (3H, t, J=7.4 Hz), 1.02(3H, d, J=6.8 Hz), 1.02(3H, d, J=6.8 Hz), 1.15-1.50(7H, m), 1.45(9H, s), 1.45(9H, s), 1.50-2.20 (12H, m), 2.60-2.70(2H, m), 3.05-3.20(2H, m), 3.97(2H, t, J=6.5 Hz), 4.04(2H, t, J=6.2 Hz), 4.25-4.40(2H, m), 5.10-5.25(4H, m), 6.85-6.95(4H, m), 7.60-7.65(4H, m).

Example 28

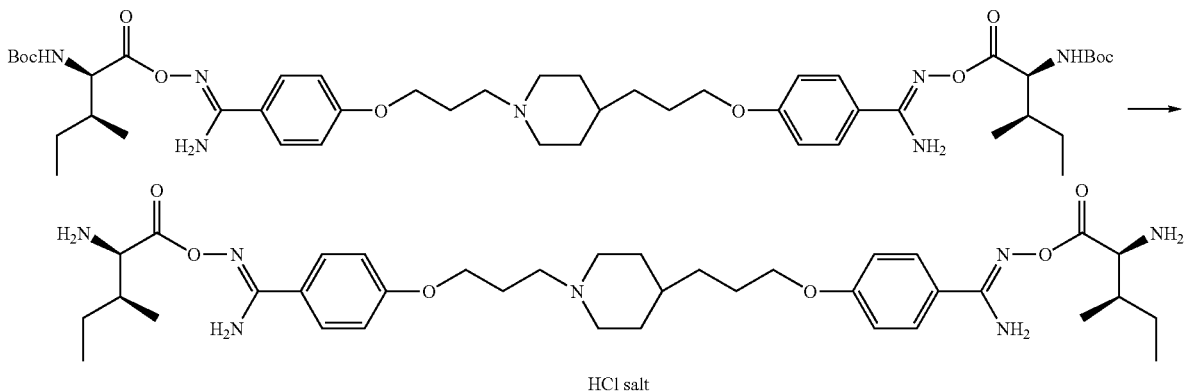

To an ethanol (5 mL) solution of 0.20 g of 4-(3-{4-[3-(4-{amino[(2S,3S)-2-(tert-butoxycarbonyl)amino-3-methylpentanoyloxyimino]methyl}phenoxy)propyl]-1-piperidinyl}propoxy)benzamide=O-[(2S,3S)-2 (tert-butoxycarbonyl)amino-3-methylpentanoyl]oxime was added 2 mL of 2.9 mol/L hydrogen chloride/ethanol at room temperature, which was then stirred at the same temperature for 5 hours. Thereto was added 2 mL of 2.9 mol/L hydrogen chloride/ethanol, which was then stirred for 26 hours. Thereto was further added 1 mL of 2.9 mol/L hydrogen chloride/ethanol, which was then stirred for 3 days. The solvent was distilled off under reduced pressure, and the resultant solid was suspended in diisopropyl ether, followed by collecting the solid matter by filtration before washing with diisopropyl ether to provide 0.13 g of 4-{3-[4-(3-{4-[amino((2S,3S)-2-amino-3-methylpentanoyloxyimino)methyl]phenoxy}propyl)-1-piperidinyl]propoxy}benzamide=O-((2S,3S)-2-amino-3-methylpentanoyl)oxime hydrochloride as white solid form.

$^1$H-NMR (DMSO-d$_6$) .δvalue: 0.85-0.95(6H, m), 0.99 (3H, d, J=6.8 Hz), 0.99(2H, d, J=6.8 Hz), 1.20-2.10(17H, m), 2.15-2.30(2H, m), 2.80-2.95(2H, m), 3.10-3.20(2H, m), 3.95-4.30(6H, m), 6.95-7.05(4H, m), 7.05-7.20(4H, m), 7.65-7.75 (4H, m), 8.50-8.60(2H, broad), 8.75-8.90(6H, broad).

Example 29

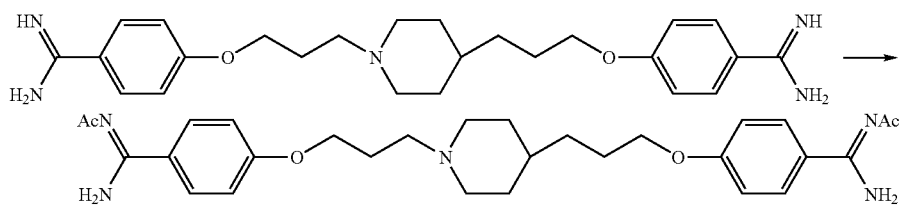

To an N,N-dimethylformamide (10 mL) suspension of 1.00 g of 4-{3-[4-(3-{4-[amino(imino)methyl] phenoxy}propyl)-1-piperidinyl]propoxy}benzamidine was added 4-nitrophenyl=acetate at room temperature, which was then stirred at the same temperature for 1 hour and 15 minutes. Chloroform and a 5% potassium carbonate aqueous solution were added to the reaction mixture, and insoluble matter was filtered off. The organic layer was separated, washed sequentially with a 5% potassium carbonate aqueous solution and a saturated sodium chloride aqueous solution, and then dried with anhydrous magnesium sulfate, followed by distilling off the solvent under reduced pressure. Ethyl acetate and water were added to the resultant residue, which was then adjusted to pH 3.0 using hydrochloric acid. The aqueous layer was separated and washed with ethyl acetate, which was then adjusted to pH 12.0 using a sodium hydroxide aqueous solution. The precipitate was collected by filtration to provide 0.80 g of N'-acetyl-4-{3-[4-(3-{4-[(acetylimino)(amino)methyl]phenoxy}propyl)-1-piperidinyl]propoxy}benzamidine as white solid form.

$^1$H-NMR (DMSO-$d_6$) $.\delta$value: 1.00-1.40(5H, m), 1.60-1.90(8H, m), 2.09(3H, s), 2.09(3H, s), 2.35-2.45(2H, m), 2.80-2.85(2H, m), 4.02(2H, t, J=6.3 Hz), 4.07(2H, t, J=6.3 Hz), 6.90-7.10(4H, m), 7.95-8.05(4H, m).

Example 30

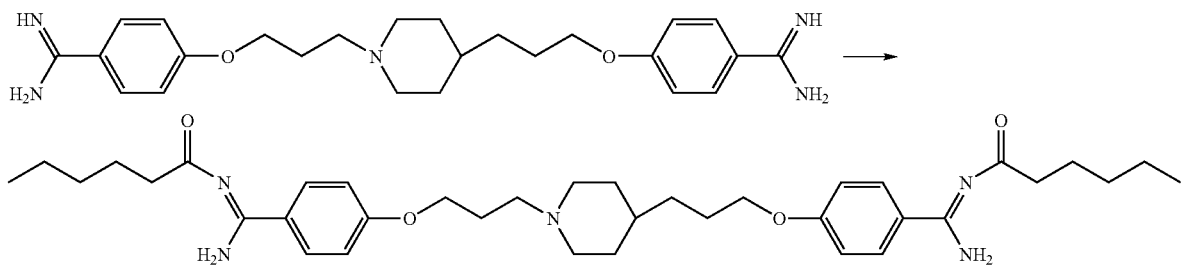

As described in Example 29, 0.62 g of 4-{3-[4-(3-{4-[amino(hexanoylimino)methyl]phenoxy}propyl)-1-piperidinyl]propoxy}-N'-(hexanoyl)benzamidine as white solid form was obtained from 0.50 g of 4-{3-[4-(3-{4-[amino(imino)methyl]phenoxy}propyl)-1-piperidinyl]propoxy}benzamidine and 0.68 g of 4-nitrophenyl=hexanoate.

$^1$H-NMR (CDCl$_3$) $.\delta$value: 0.91(3H, t, J=6.7 Hz), 0.91 (3H, t, J=6.7 Hz), 1.20-1.45(13H, m), 1.65-2.05(12H, m), 2.45-2.55(2H, m), 2.54(2H, t, J=7.5 Hz), 2.54(2H, t, J=7.5 Hz), 2.90-3.00(2H, m), 4.00(2H, t, J=6.5 Hz), 4.06(2H, t, J=6.3 Hz), 6.93(2H, d, J=8.7 Hz), 6.94(2H, d, J=8.7 Hz), 7.84(2H, d, J=8.7 Hz), 7.84 (2H, d, J=8.7 Hz).

Example 31

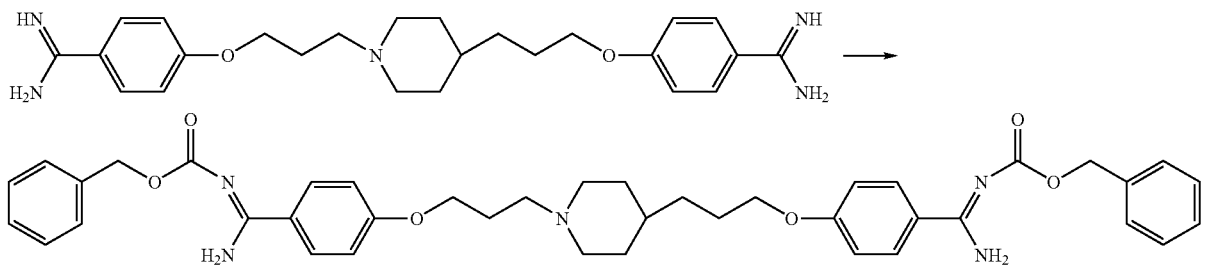

To an N,N-dimethylformamide (10 mL) suspension of 0.50 g of 4-{3-[4-(3-{4-[amino(imino)methyl]phenoxy}propyl)-1-piperidinyl]propoxy}benzamidine was added 0.78 g of benzyl=4-nitrophenyl=carbonate at room temperature, which was then stirred at the same temperature for 50 minutes. Chloroform and water were added to the reaction mixture. The organic layer was separated, washed sequentially with a 5% potassium carbonate aqueous solution and a saturated sodium chloride aqueous solution, and then dried with anhydrous magnesium sulfate, followed by distilling off the solvent under reduced pressure. The resultant residue was purified using silica gel column chromatography (eluent; chloroform:methanol=4:1) to provide 0.67 g of 4-{3-[4-(3-{4-[amino(benzyloxycarbonylimino)methyl]phenoxy}propyl)-1-piperidinyl]propoxy}-N'-(benzyloxycarbonyl)benzamidine as white solid form.

$^1$H-NMR (CDCl$_3$) δvalue: 1.20-1.45(5H, m), 1.65-2.05 (8H, m), 2.45-2.55(2H, m), 2.85-3.00(2H, m), 3.99(2H, t, J=6.6 Hz), 4.06(2H, t, J=6.3 Hz), 5.21(2H, s), 5.21(2H, s), 6.91(2H, d, J=8.7 Hz), 6.93(2H, d, J=8.7 Hz), 7.20-7.50(10H, m), 7.85(2H, d, J=8.7 Hz), 7.85(2H, d, J=8.7 Hz).

Example 32

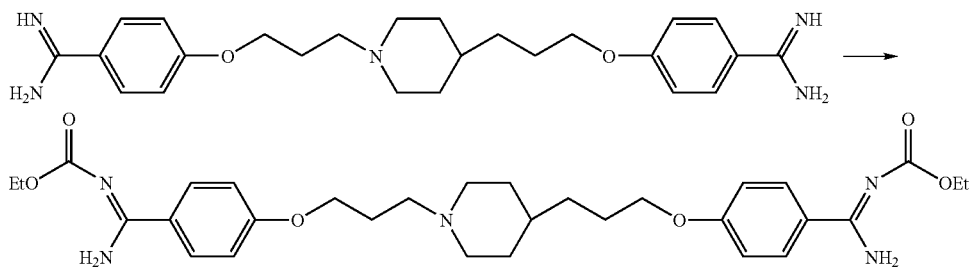

To an N,N-dimethylformamide (10 mL) suspension of 0.50 g of 4-{3-[4-(3-{4-[amino(imino)methyl]phenoxy}propyl)-1-piperidinyl]propoxy}benzamidine was added 0.60 g of ethyl=4-nitrophenyl=carbonate at room temperature, which was then stirred at the same temperature for 2 hours and 30 minutes. Chloroform and water were added to the reaction mixture. The organic layer was separated, washed sequentially with water, a 5% potassium carbonate aqueous solution, and a saturated sodium chloride aqueous solution, and then dried with anhydrous magnesium sulfate, followed by distilling off the solvent under reduced pressure. The resultant residue was purified using silica gel column chromatography (eluent; chloroform:ethanol=4:1) to provide 0.58 g of 4-{3-[4-(3-{4-[amino(ethoxycarbonylimino)methyl]phenoxy}propyl)-1-piperidinyl]propoxy}-N'-(ethoxycarbonyl)benzamidine as white solid form.

¹H-NMR (CDCl₃) δvalue: 1.20-1.45(5H, m), 1.36(3H, t, J=7.1 Hz), 1.36(3H, t, J=7.1 Hz), 1.65-2.05(8H, m), 2.45-2.55(2H, m), 2.90-3.00(2H, m), 4.00(2H, t, J=6.5 Hz), 4.06(2H, t, J=6.3 Hz), 4.22(2H, q, J=7.1 Hz), 4.22(2H, q, J=7.1 Hz), 6.92(2H, d, J=8.8 Hz), 6.93 (2H, d, J=8.8 Hz), 7.86(2H, d, J=8.8 Hz), 7.86(2H, d, J=8.8 Hz).

Example 33

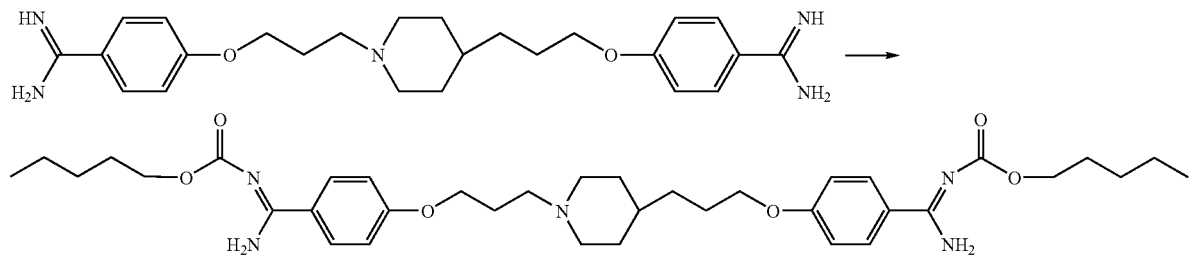

As described in Example 31, 0.23 g of 4-{3-[4-(3-{4-[amino(pentyloxycarbonylimino)methyl]phenoxy}propyl)-1-piperidinyl]propoxy}-N'-(pentyloxycarbonyl)benzamidine as white solid form was obtained from 0.50 g of 4-{3-[4-(3-{4-[amino(imino)methyl]phenoxy}propyl)-1-piperidinyl]propoxy}benzamidine and 1.20 g of 4-nitrophenyl=pentyl=carbonate.

¹H-NMR (CDCl₃) δvalue: 0.91(3H, t, J=7.1 Hz), 0.91 (3H, t, J=7.1 Hz), 1.20-2.05(25H, m), 2.45-2.55(2H, m), 2.90-3.00(2H, m), 3.99(2H, t, J=6.6 Hz), 4.06(2H, t, J-6.6 Hz), 4.15(2H, t, J=6.8 Hz), 4.15(2H, t, J=6.8 Hz), 6.92(2H, d, J=8.6 Hz), 6.93 (2H, d, J=8.6 Hz), 7.85(2H, d, J=8.6 Hz), 7.85(2H, d, J=8.6 Hz).

Example 34

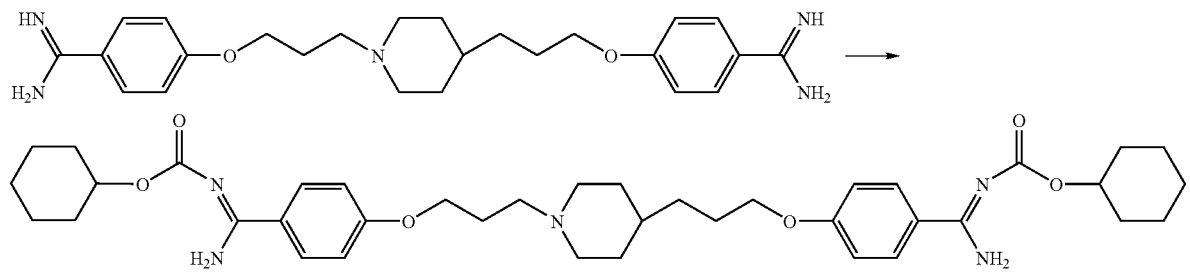

As described in Example 31, 0.33 g of 4-{3-[4-(3-{4-[amino(cyclohexyloxycarbonylimino)methyl]phenoxy}propyl)-1-piperidinyl]propoxy}-N'-(cyclohexyloxycarbonyl)benzamidine as white solid form was obtained from 0.50 g of 4-{3-[4-(3-{4-[amino(imino)methyl]phenoxy}propyl)-1-piperidinyl]propoxy}benzamidine and 0.76 g of cyclohexyl=4-nitrophenyl=carbonate.

¹H-NMR (CDCl₃) δvalue: 1.15-2.10(33H, m), 2.45-2.55(2H, m), 2.90-3.00(2H, m), 3.99(2H, t, J=6.5 Hz), 4.06(2H, t, J=6.3 Hz), 4.60-4.75(2H, m), 6.91(2H, d, J=8.8 Hz), 6.92(2H, d, J=8.8 Hz), 7.85(2H, d, J=8.8 Hz), 7.85(2H, d, J=8.8 Hz).

Example 35

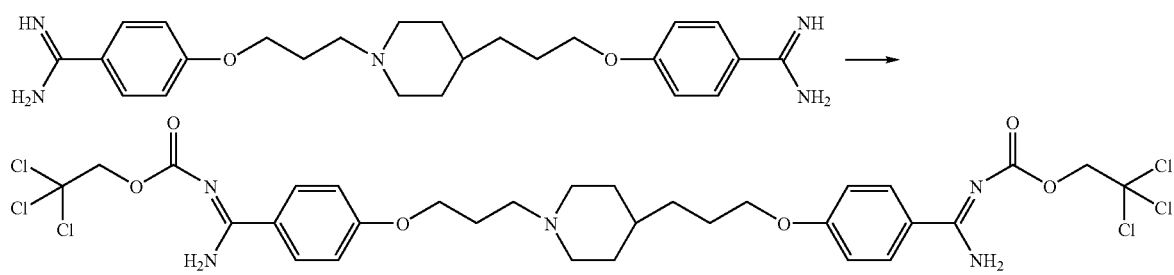

As described in Example 31, 0.72 g of 4-{3-[4-(3-{4-[amino(2,2,2-trichloroethoxycarbonylimino)methyl]phenoxy}propyl)-1-piperidinyl]propoxy}-N'-(2,2,2-trichloroethoxycarbonyl)benzamidine as white solid form was obtained from 0.50 g of 4-{3-[4-(3-{4-[amino(imino)methyl]phenoxy}propyl)-1-piperidinyl]propoxy}benzamidine and 0.90 g of 4-nitrophenyl=2,2,2-trichloroethyl=carbonate.

$^1$H-NMR (CDCl$_3$) .δ value: 1.20-1.45(5H, m), 1.65-2.05 (8H, m), 2.45-2.55(2H, m), 2.90-3.00(2H, m), 4.01(2H, t, J=6.5 Hz), 4.08(2H, t, J=6.3 Hz), 4.87(2H, s), 4·87(2H, s), 6.94(2H, d, J=8.8 Hz), 6.95(2H, d, J=8.8 Hz), 7.89 (2H, d, J=8.8 Hz), 7.90(2H, d, J=8.8 Hz).

Example 36

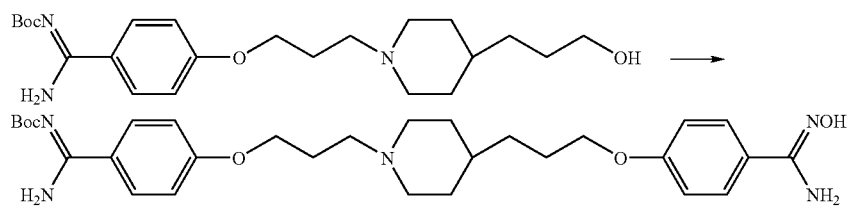

To a chloroform (20 mL) solution of 2.17 g of tert-butyl=[1-amino-1-(4-{3-[4-(3-hydroxypropyl)-1-piperidinyl]propoxy}phenyl)methylidene]carbamate was added 0.86 mL of triethylamine at room temperature, to which 0.48 mL of methanesulfonyl chloride was added dropwise under cooling with ice, followed by stirring at room temperature for one hour. To this mixture were added 0.36 mL of triethylamine and 0.20 mL of methanesulfonyl chloride under cooling with ice, which was then stirred at room temperature for 50 minutes. Water was added to the reaction mixture. The organic layer was separated, washed with a saturated sodium chloride aqueous solution, and then dried with anhydrous magnesium sulfate, followed by distilling off the solvent under reduced pressure. The resultant residue was dissolved in 20 mL of dimethylsulfoxide, to which 1.43 g of potassium carbonate and 0.79 g of N', 4-dihydroxybenzamidine were added, followed by stirring at 70° C. for one hour. The reaction mixture was cooled down to room temperature, to which water, chloroform, and a sodium hydroxide aqueous solution were then added. The organic layer was separated, washed sequentially with a sodium hydroxide aqueous solution and a saturated sodium chloride aqueous solution, and then dried with anhydrous magnesium sulfate, followed by distilling off the solvent under reduced pressure. The resultant residue was purified using silica gel column chromatography (eluent; chloroform:methanol=4:1) and suspended in a mixture of chloroform and a sodium hydroxide aqueous solution, followed by collecting the solid matter by filtration to provide 0.38 g of tert-butyl=[1-amino-1-(4-{3-[4-(3-{4-[amino(hydroxyimino)methyl]phenoxy}propyl)-1-piperidinyl]propoxy}phenyl)methylidene]carbamate as white solid form.

$^1$H-NMR (DMSO-d$_6$) .δvalue: 1.05-1.40(5H, m), 1.44 (9H, s), 1.60-1.80(4H, m), 1.80-1.95(4H, m), 2.35-2.45(2H, m), 2.80-2.90(2H, m), 3.96(2H, t, J=6.6 Hz), 4.06(2H, t, J=6.3 Hz), 5.70(2H, s), 6.90(2H, d, J=8.8 Hz), 6.98(2H, d, J=8.8 Hz), 7.58(2H, d, J=8.8 Hz), 7.94(2H, d, J=8.8 Hz), 8.70-9.30(2H, broad), 9.43(1H, s).

Example 37

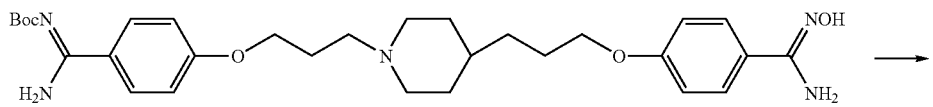

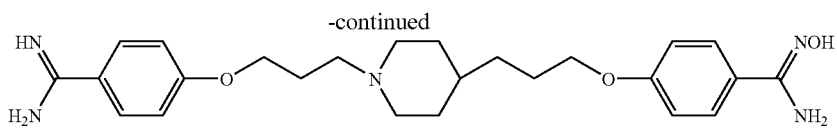

To an ethanol (5 mL) suspension of 0.30 g of tert-butyl=[1-amino-1-(4-{3-[4-(3-{4-[amino(hydroxyimino)methyl]phenoxy}propyl)-1-piperidinyl]propoxy}phenyl)methylidene]carbamate was added 5 mL of hydrochloric acid at room temperature, which was then stirred at the same temperature for 15 hours. The solvent was distilled off under reduced pressure, and water was subsequently added to the resultant residue, which was then adjusted to pH 12.5 using a 1 mol/L sodium hydroxide aqueous solution. The precipitate was collected by filtration and washed with water to provide 0.22 g of 4-{3-[4-(3-{4-[amino(hydroxyimino)methyl]phenoxy}propyl)-1-piperidinyl]propoxy}benzamidine as white solid form.

$^1$H-NMR (DMSO-$d_6$) $\delta$value: 1.05-1.40(5H, m), 1.60-1.90(8H, m), 2.35-2.45(2H, m), 2.80-2.90(2H, m), 3.96(2H, t, J=6.3 Hz), 4.02(2H, t, J=6.2 Hz), 5.70(2H, s), 6.85-6.95 (4H, m), 7.58(2H, d, J=8.8 Hz), 7.71(2H, d, J=8.5 Hz).

1.05 g of potassium carbonate and 0.58 g of N', 4-dihydroxybenzamidine were then added, followed by stirring at 60 to 70° C. for one hour. The reaction mixture was cooled down to room temperature, to which chloroform and water were then added, followed by collecting the precipitate by filtration to provide 2.23 g of tert-butyl=[1-amino-1-(4-{3-[1-(3-{4-[amino(hydroxyimino)methyl]phenoxy}propyl)-4-piperidinyl]propoxy}phenyl)methylidene]carbamate as white solid form.

$^1$H-NMR (DMSO-$d_6$) $\delta$value: 1.00-1.50(5H, m), 1.44 (9H, s), 1.60-1.90(8H, m), 2.35-2.55(2H, m), 2.80-2.90(2H, m), 3.95-4.05(4H, m), 5.70(2H, s), 6.90(2H, d, J=8.8 Hz), 6.98(2H, d, J=8.8 Hz), 7.58(2H, d, J=8.8 Hz), 7.93(2H, d, J=8.8 Hz), 8.60-9.40(2H, broad), 9.43(1H, s).

Example 38

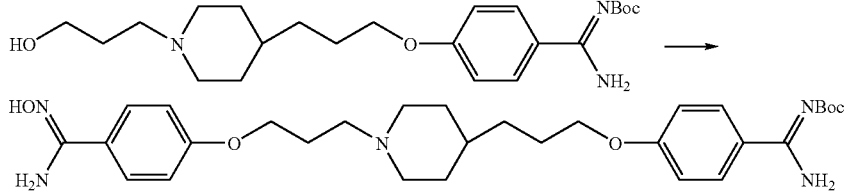

To a tetrahydrofuran (20 mL) suspension of 1.59 g of tert-butyl=[1-amino-1-(4-{3-[1-(3-hydroxypropyl)-4-piperidinyl]propoxy}phenyl)methylidene]carbamate were added 10 mL of methylene chloride and 0.63 mL of triethylamine at room temperature. To this mixture was dropwise added 0.35 mL of methanesulfonyl chloride under cooling with ice, which was then stirred at room temperature for 20 minutes. Chloroform and water were added to the reaction mixture. The organic layer was separated, washed with a saturated sodium chloride aqueous solution, and then dried with anhydrous magnesium sulfate, followed by distilling off the solvent under reduced pressure. The resultant residue was dissolved in 20 mL of N,N-dimethylformamide, to which

Example 39

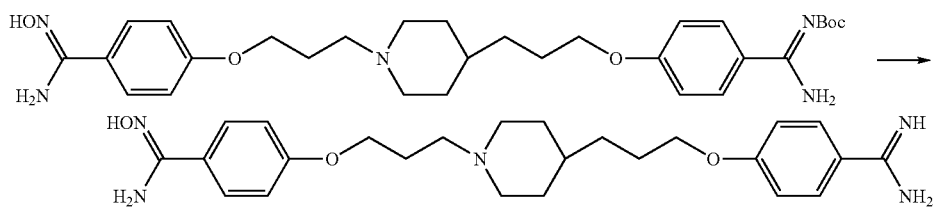

To an ethanol (5 mL) suspension of 0.50 g of tert-butyl=[1-amino-1-(4-{3-[1-(3-{4-[amino(hydroxyimino)methyl]phenoxy}propyl)-4-piperidinyl]propoxy}phenyl)methylidene]carbamate was added 1 mL of hydrochloric acid at room temperature, which was then stirred at the same temperature for 15 hours and 30 minutes. To the reaction mixture was added 4 mL of hydrochloric acid at room temperature, which was then stirred at the same temperature for 2 hours and 30 minutes. The solvent was distilled off under reduced pressure, and water was then added, followed by adjustment to pH 12.5 using a 5 mol/L sodium hydroxide aqueous solution. The precipitate was collected by filtration and washed with water. The resultant solid was dissolved in 1 mol/L hydrochloric acid, followed by distilling off the solvent under reduced pressure before purification using silica gel column chromatography (silica gel: ODS-A from YMC, eluent; water:ethanol=95:5). The eluate was concentrated to about 20 mL, which was then adjusted to pH 12.5 using a 5 mol/L sodium hydroxide aqueous solution. The precipitate was collected by filtration and washed with water to provide 0.17 g of 4-{3-[4-(3-{4-[amino(imino)methyl]phenoxy}propyl)-1-piperidinyl]propoxy}-N'-hydroxybenzamidine as white solid form.

$^1$H-NMR (DMSO-d$_6$) .δvalue: 1.05-1.40(5H, m), 1.60-1.85(8H, m); 2.35-2.45(2H, m), 2.80-2.90(2H, m), 3.95-4.05 (4H, m), 5.70(2H, s), 6.90(2H, d, J=8.7 Hz), 6.91(2H, d, J=8.7 Hz), 7.58(2H, d, J=8.7 Hz), 7.71(2H, d, J=8.7 Hz).

Example 40 organic layer was separated, washed with a saturated sodium chloride aqueous solution, and then dried with anhydrous magnesium sulfate, followed by distilling off the solvent under reduced pressure. The resultant residue was dissolved in 20 mL of N,N-dimethylformamide, to which 0.36 g of N', 4-dihydroxybenzamidine and 0.65 g of potassium carbonate were then added, followed by stirring at 60° C. for 40 minutes. The reaction mixture was cooled down to room temperature, to which ethyl acetate and a 5% potassium carbonate aqueous solution were then added. The precipitate was collected by filtration and washed sequentially with water and ethyl acetate to provide 0.55 g of benzyl=[1-amino-1-(4-{3-[1-(3-{4-[amino(hydroxyimino)methyl]phenoxy}propyl)-4-piperidinyl]propoxy}phenyl)methylidene]carbamate as white solid form.

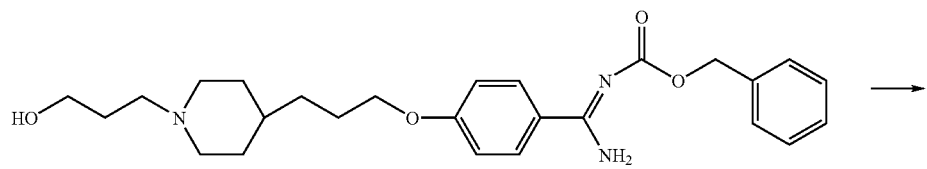

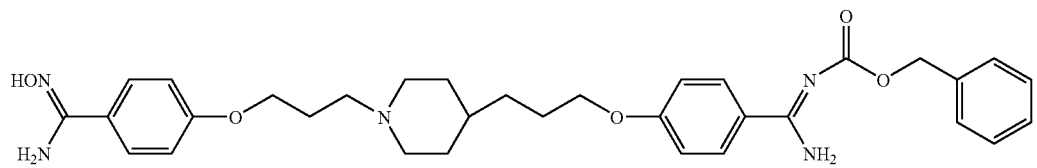

To a tetrahydrofuran (10 mL) solution of 1.06 g of benzyl=[1-amino-1-(4-{3-[1-(3-hydroxypropyl)-4-piperidinyl]propoxy}phenyl)methylidene]carbamate was added 0.39 mL of triethylamine under cooling with ice. Thereto was dropwise added 0.22 mL of methanesulfonyl chloride, which was then stirred at the same temperature for 15 minutes. Chloroform and water were added to the reaction mixture. The $^1$H-NMR (DMSO-d$_6$) .δvalue: 1.05-1.40(5H, m), 1.60-1.90(8H, m), 2.30-2.45(2H, m), 2.80-2.90(2H, m), 3.95-4.05 (4H, m), 5.09(2H, s), 5.70(2H, s), 6.90(2H, d, J=8.9 Hz), 7.00 (2H, d, J=8.9 Hz), 7.25-4.45(5H, m), 7.58(2H, d, J=8.9 Hz), 7.97(2H, d, J=8.9 Hz), 8.90-9.60(3H, broad).

Example 41

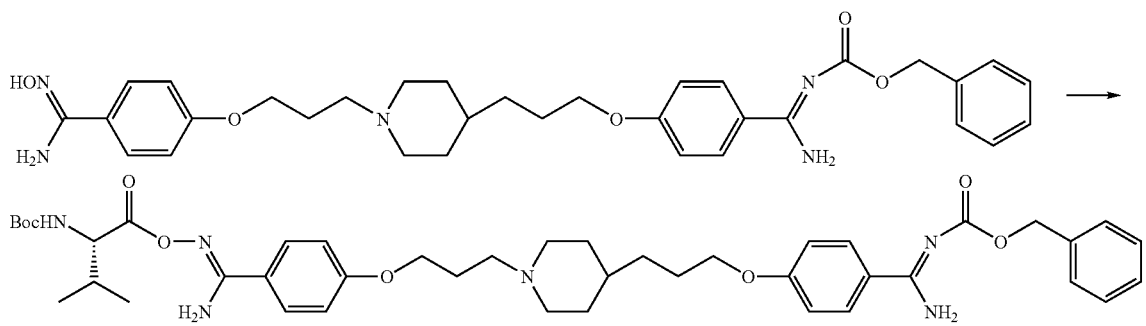

To an N,N-dimethylformamide (5 mL) solution of 89 mg of N-(tert-butoxycarbonyl)-L-valine was added 66 mg of 1,1'-carbonyldiimidazole at room temperature, which was then stirred at the same temperature for 2 hours and 30 minutes. To this mixture was added 0.20 g of benzyl=[1-amino-1-(4-{3-[1-(3-{4-[amino(hydroxyimino)methyl]phenoxy}propyl)-4-piperidinyl]propoxy}phenyl)methylidene]carbamate at room temperature, which was then stirred at the same temperature for 3 days. Ethyl acetate and water were added to the reaction mixture. The organic layer was separated, washed with a saturated sodium chloride aqueous solution, and then dried with anhydrous magnesium sulfate, followed by distilling off the solvent under reduced pressure. The resultant residue was purified using silica gel column chromatography (eluent; chloroform:methanol=4:1) to provide 0.34 g of 4-{3-[4-(3-{4-[amino(benzyloxycarbonylimino)methyl]phenoxy}propyl)-1-piperidinyl]propoxy}benzamide=O-[(2S)-2-(tert-butoxycarbonyl)amino-3-methylbutylyl]oxime as white solid form.

$^1$H-NMR (CDCl$_3$) $\delta$value: 1.01(3H, d, J=6.8 Hz), 1.05 (3H, d, J=6.6 Hz), 1.25-1.50(5H, m), 1.45(9H, s), 1.65-1.85 (4H, m), 1.95-2.05(4H, m), 2.10-2.25(1H, m), 2.50-2.60(2H, m), 2.95-3.05(2H, m), 3.99(2H, t, J=6.5 Hz), 4.04(2H, t, J=6.3 Hz), 4.25-4.35(1H, m), 5.05-5.20(3H, m), 5.21(2H, s), 6.85-6.95(4H, m), 7.25-7.50(5H, m), 7.60-7.65(2H, m), 7.80-7.90(2H, m).

Example 42 was added 2 mL of trifluoroacetic acid at room temperature, which was then stirred at the same temperature for one hour. The solvent was distilled off under reduced pressure, and 2.9 mol/L hydrogen chloride/ethanol was then added, followed by distilling off the solvent under reduced pressure. The resultant solid was suspended in diisopropyl ether, and solid matter was collected by filtration and washed with diisopropyl ether to provide 0.04 g of 4-{3-[4-(3-{4-[amino(benzyloxycarbonylimino)methyl]phenoxy}propyl)-1-piperidinyl]propoxy}benzamide=O-((2S)-2-amino-3-methylbutylyl)oxime hydrochloride as white solid form.

$^1$H-NMR (DMSO-d$_6$) $\delta$value: 1.01(3H, d, J=6.8 Hz), 1.03(3H, d, J=6.8 Hz), 1.30-1.95(9H, m), 2.10-2.35(3H, m), 2.80-3.00(2H, m), 3.10-3.20(2H, m), 3.45-3.55(2H, m), 3.90-4.00(1H, m), 4.05-4.20(4H, m), 5.36(2H, s), 7.02(2H, d, J=9.0 Hz), 7.05-7.15(2H, broad), 7.15(2H, d, J=8.8 Hz), 7.35-

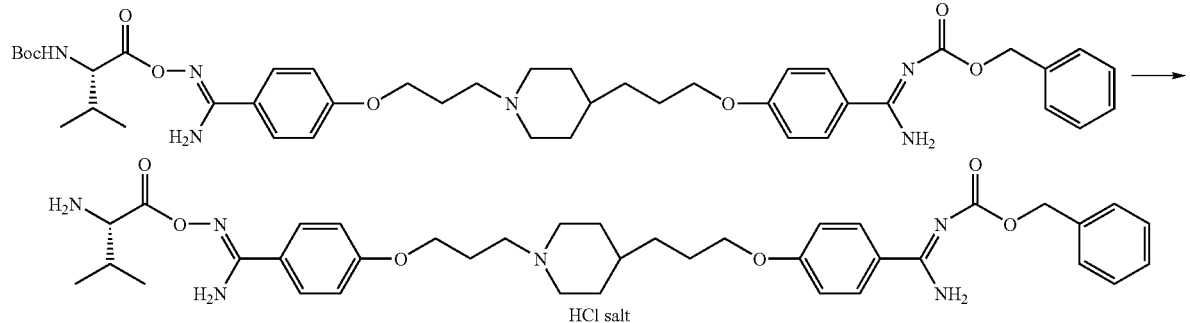

To a chloroform (10 mL) solution of 0.10 g of 4-{3-[4-(3-{4-[amino(benzyloxycarbonylimino)methyl]phenoxy}propyl)-1-piperidinyl]propoxy}benzamide=O-[(2S)-2-(tert-butoxycarbonyl)amino-3-methylbutylyl]oxime 7.55(5H, m), 7.69(2H, d, J=8.8 Hz), 7.81(2H, d, J=9.0 Hz), 8.60-8.75(3H, broad).

Example 43

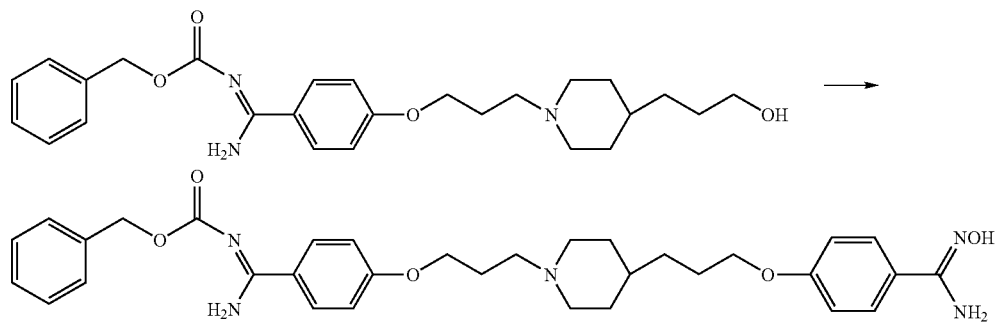

To a tetrahydrofuran (20 mL) solution of 0.93 g of benzyl=[1-amino-1-(4-{3-[4-(3-hydroxypropyl)-1-piperidinyl]propoxy}phenyl)methylidene]carbamate was added 0.37 mL of triethylamine at room temperature, to which 0.19 mL of methanesulfonyl chloride was then added under cooling with ice, followed by stirring at room temperature for 30 minutes. Ethyl acetate, water, and a saturated sodium chloride aqueous solution were added to the reaction mixture. The organic layer was separated and dried with anhydrous magnesium sulfate, followed by distilling off the solvent under reduced pressure. The resultant oily matter was dissolved in 20 mL of N,N-dimethylformamide, to which 0.25 g of N',4-dihydroxybenzamidine and 0.45 g of potassium carbonate were then added, followed by stirring at 70° C. for 4 hours. Thereto was added 0.12 g of N',4-dihydroxybenzamidine, which was then stirred at 70° C. for one hour. The reaction mixture was cooled down to room temperature, and then added to a mixture of ethyl acetate and water. The organic layer was separated, washed with water, and then dried with anhydrous magnesium sulfate, followed by distilling off the solvent under reduced pressure. The resultant residue was suspended in diisopropyl ether, and the solid matter was collected by filtration and purified using silica gel column chromatography (eluent; chloroform:methanol=5:1) to provide 0.22 g of benzyl=[1-amino-1-(4-{3-[4-(3-{4-[amino(hydroxyimino)methyl]phenoxy}propyl)-1-piperidinyl]propoxy}phenyl)methylidene]carbamate as white solid form.

$^1$H-NMR (CDCl$_3$) δvalue: 1.20-1.45(5H, m), 1.65-2.05 (8H, m), 2.45-2.55(2H, m), 2.90-3.00(2H, m), 3.96(2H, t, J=6.5 Hz), 4.06(2H, t, J=6.3 Hz), 4.79(2H, s), 5.21(2H, s), 6.89(2H, d, J=8.5 Hz), 6.93(2H, d, J=8.8 Hz), 7.25-7.60(5H, m), 7.55(2H, d, J=8.5 Hz), 7.85(2H, d, J=8.8 Hz).

Example 44

To an N-methyl-2-pyrrolidone (10 mL) solution of 44 mg of N-(tert-butoxycarbonyl)-L-valine was added 33 mg of 1,1'-carbonyldiimidazole at room temperature, which was then stirred at the same temperature for 3 hours. Thereto was added 0.10 g of benzyl=[1-amino-1-(4-{3-[4-(3-{4-[amino(hydroxyimino)methyl]phenoxy}propyl)-1-piperidinyl]propoxy}phenyl)methylidene]carbamate at room temperature, which was then stirred at the same temperature for 17 hours. The reaction mixture was added to a mixture of ethyl acetate and water. The organic layer was separated, washed with water, and then dried with anhydrous magnesium sulfate, followed by distilling off the solvent under reduced pressure. The resultant residue was purified using silica gel column chromatography (eluent; chloroform:methanol=30:1) to provide 0.11 g of 4-(3-{4-[3-(4-{amino[(2S)-2-(tert-butoxycarbonyl)amino-3-methylbutylyloxyimino]methyl}phenoxy)propyl]-1-piperidinyl}propoxy)-N'-benzyloxycarbonylbenzamidine as white solid form.

$^1$H-NMR (CDCl$_3$) δvalue: 1.01(3H, d, J=6.8 Hz), 1.05 (3H, d, J=6.8 Hz), 1.25-1.45(5H, m), 1.45(9H, s), 1.60-2.25 (9H, m), 2.50-2.60(2H, m), 2.95-3.05(2H, m), 3.97(2H, t, J=6.5 Hz), 4.06(2H, t, J=6.3 Hz), 4.25-4.35(1H, m), 5.05-5.20(2H, m), 5.21(2H, s), 6.85-6.95(4H, m), 7.25-7.40(3H, m), 7.40-7.50(2H, m), 7.60-7.70(2H, m), 7.80-7.90(2H, m).

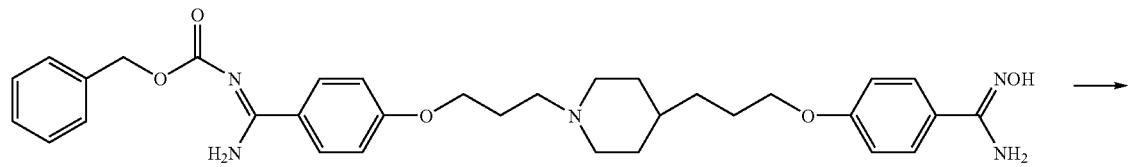

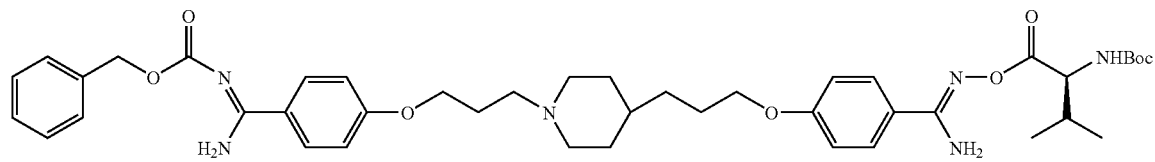

Example 45

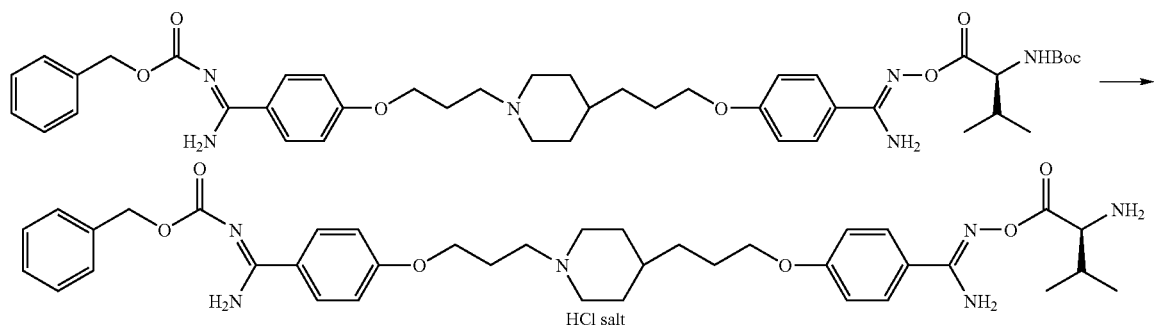

To a chloroform (1.0 mL) solution of 0.02 g of 4-(3-{4-[3-(4-{amino[(2S)-2-(tert-butoxycarbonyl)amino-3-methylbutylyloxyimino]methyl}phenoxy)propyl]-1-piperidinyl}propoxy)-N'-benzyloxycarbonylbenzamidine was added 0.5 mL of trifluoroacetic acid at room temperature, which was then stirred at the same temperature for 2 hours. The solvent was distilled off under reduced pressure, and 2.9 mol/L hydrogen chloride/ethanol was then added to the resultant residue, followed by distilling off the solvent under reduced pressure. The resultant residue was suspended in diisopropyl ether, and the solid matter was collected by filtration and washed with diisopropyl ether to provide 14 mg of 4-{3-[4-(3-{4-[amino((2S)-2-amino-3-methylbutylyloxyimino)methyl]phenoxy}propyl)-1-piperidinyl]propoxy}-N'-benzyloxycarbonylbenzamidine hydrochloride as pale brown solid form.

$^1$H-NMR (DMSO-$d_6$). δ value: 1.01(3H, d, J=6.8 Hz), 1.02(3H, d, J=6.8 Hz), 1.30-1.65(5H, m), 1.70-1.95(4H, m), 2.15-2.35(3H, m), 2.80-2.95(2H, m), 3.10-3.25(2H, m), 3.45-3.55(2H, m), 3.90-4.25(5H, m), 5.36(2H, s), 7.00(2H, d, J=8.8 Hz), 7.15(2H, d, J=9.0 Hz), 7.38-7.50(5H, m), 7.65-7.75(2H, m), 7.83(2H, d, J=8.8 Hz), 8.55-8.65(2H, broad).

acetic anhydride at room temperature, which was then stirred at the same temperature for one hour. The solvent was distilled off under reduced pressure, and the resultant residue was subsequently added to a mixture of water and chloroform, which was then adjusted to pH 7.5 using a saturated sodium bicarbonate aqueous solution. The precipitate was collected by filtration and washed with water and chloroform to provide 1.07 g of 4-{3-[4-(3-{4-[amino(acetyloxyimino) methyl]phenoxy}propyl)-1-piperidinyl] propoxy}benzamide=O-acetyloxime as white solid form.

$^1$H-NMR (DMSO-$d_6$). δ value: 1.05-1.40(5H, m), 1.60-1.80(4H, m), 1.80-1.95(4H, m), 2.12(3H, s), 2.12(3H, s), 2.35-2.45(2H, m), 2.80-2.90(2H, m), 3.99(2H, t, J=6.5 Hz), 4.03(2H, t, J=6.3 Hz), 6.60-6.80(4H, broad), 6.95-7.00(4H, m), 7.64(2H, d, J=7.6 Hz), 7.64(2H, d, J=7.6 Hz).

Example 46

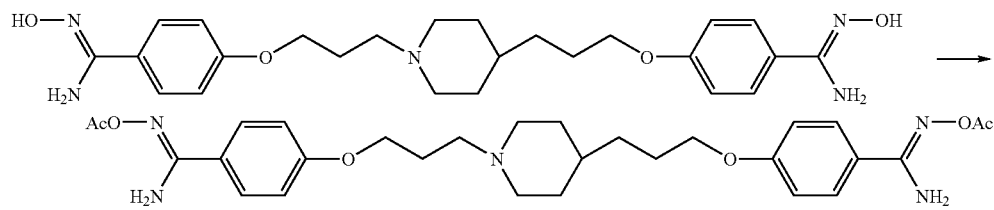

To an acetic acid (15 mL) suspension of 1.00 g of 4-{3-[4-(3-{4-[amino(hydroxyimino)methyl]phenoxy}propyl)-1-piperidinyl]propoxy}benzamide=oxime was added 0.48 mL of

Example 47

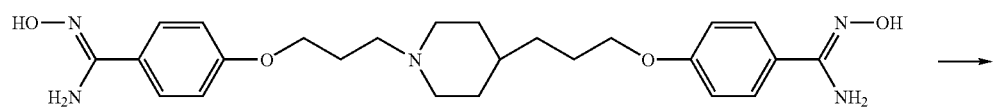

-continued

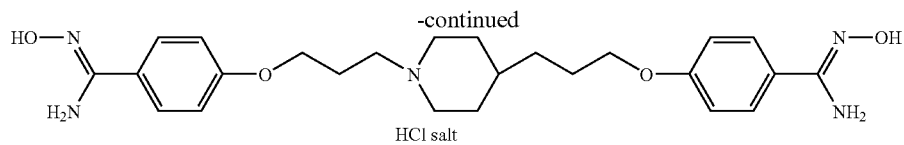
HCl salt

To a 2-propanol (20 mL) suspension of 4.00 g of 4-{3-[4-(3-{4-[amino(hydroxyimino)methyl]phenoxy}propyl)-1-piperidinyl]propoxy}benzamide=oxime were added 4 mL of water and 2.37 mL of hydrochloric acid at room temperature, which was then heated to reflux for 3 minutes. The mixture was cooled down to room temperature, to which 10 mL of 2-propanol was then added under cooling with ice, followed by stirring at the same temperature for one hour. The precipitate was collected by filtration and washed with a 90% (v/v) 2-propanol aqueous solution to provide 3.94 g of 4-{3-[4-(3-{4-[amino(hydroxyimino)methyl]phenoxy}propyl)-1-piperidinyl]propoxy}benzamide=oxime hydrochloride.

$^1$H-NMR (DMSO-$d_6$) . δvalue: 1.30-1.65(5H, m), 1.70-1.95(4H, m), 2.15-2.30(2H, m), 2.80-3.00(2H, m), 3.10-3.20 (2H, m), 3.45-3.55(2H, m), 4.08(2H, t, J=6.3 Hz), 4.17(2H, t, J=6.1 Hz), 7.05-7.20(4H, m), 7.70-7.80(4H, m), 8.50-9.50 (4H, broad), 10.70-10.90(1H, broad), 11.00-11.20(2H, broad).

Example 48 was then stirred at the same temperature for 2 hours. Thereto was added 0.50 g of 4-{3-[4-(3-{4-[amino(hydroxyimino)methyl]phenoxy}propyl)-1-piperidinyl]propoxy}benzamide=oxime at room temperature, which was then stirred at the same temperature for 3 hours and 40 minutes. The reaction mixture was added to a mixture of ethyl acetate and water, and the precipitate was collected by filtration to provide 0.82 g of 4-(3-{4-[3-(4-{amino[(2S)-2-(tert-butoxycarbonyl)amino-3-phenylpropionyloxyimino]methyl}phenoxy)propyl]-1-piperidinyl}propoxy)-N'-[(2S)-2-(tert-butoxycarbonyl)amino-3-phenylpropionyloxy]benzamidine as white solid form.

$^1$H-NMR (CDCl$_3$) . δvalue: 1.24-1.28(3H, m), 1.43(9H, s), 1.43(9H, s), 1.65-1.85(4H, m), 1.90-2.10(5H, m), 2.45-2.50(2H, m), 2.90-2.95(2H, m), 3.05-3.40(5H, m), 3.90-4.05 (4H, m), 4.75-4.85(4H, m), 5.15-5.20(2H, m), 6.85-6.90(4H, m), 7.20-7.35(10H, m), 7.55-7.60(4H, m).

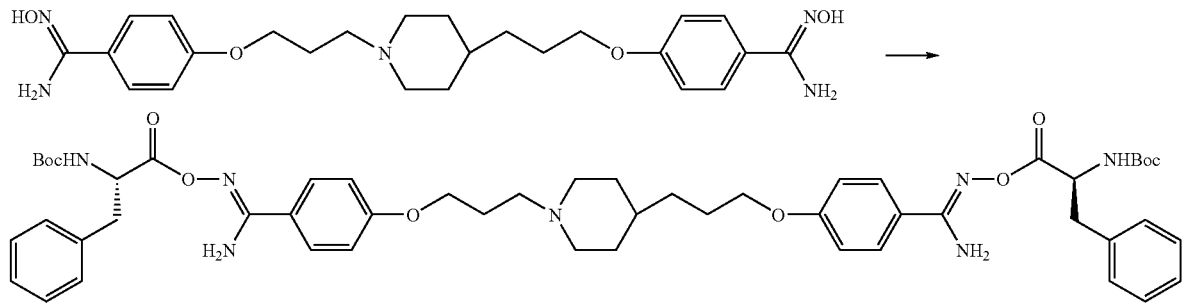

To an N-methyl-2-pyrrolidone (10 mL) solution of 0.56 g of N-(tert-butoxycarbonyl)-L-phenylalanine was added 0.35 g of 1,1'-carbonyldiimidazole at room temperature, which Example 49

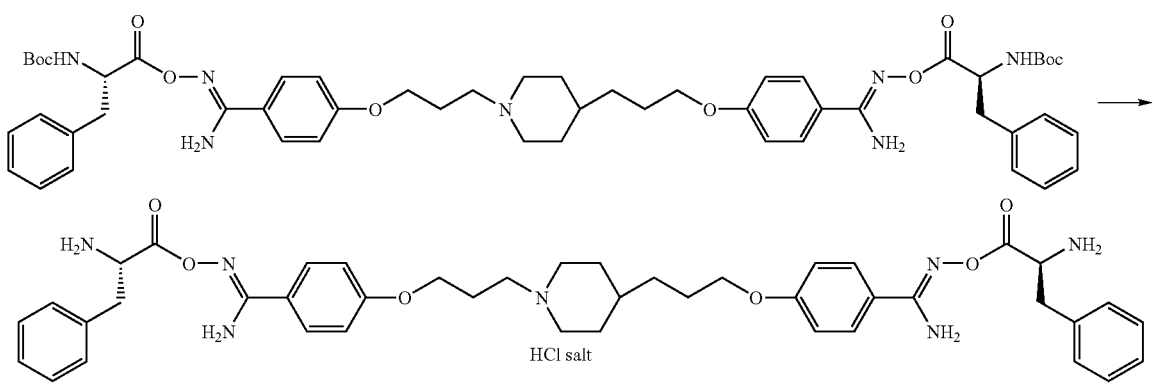
HCl salt

To an ethanol (10 mL) suspension of 0.50 g of 4-(3-{4-[3-(4-{amino[(2S)-2-(tert-butoxycarbonyl)amino-3-phenylpropionyloxyimino]methyl}phenoxy)propyl]-1-piperidinyl}propoxy)-N'-[(2S)-2-(tert-butoxycarbonyl)amino-3-phenylpropionyloxy]benzamidine was added 5 mL of 2.9 mol/L hydrogen chloride/ethanol under cooling with ice, which was then stirred at the same temperature for 20 minutes, followed by allowing to stand at room. temperature for 26 hours. The solvent was distilled off under reduced pressure, and the resultant residue was suspended in chloroform, followed by collecting solid matter by filtration to provide 0.50 g of 4-{3-[4-(3-{4-[amino((2S)-2-amino-3-phenylpropionyloxyimino)methyl]phenoxy}propyl)-1-piperidinyl]propoxy}-N'-((2S)-2-amino-3-phenylpropionyloxy)benzamidine hydrochloride as slightly pale yellow solid form.

$^1$H-NMR (DMSO-$d_6$) $\delta$value: 1.35-1.40(2H, m), 1.55-1.70(3H, m), 1.70-1.95(5H, m), 2.20-2.30(2H, m), 2.85-2.95(2H, m), 3.10-3.35(4H, m), 3.45-3.50(2H, m), 4.05-4.15(4H, m), 4.15-4.25(3H, m), 7.10-7.20(4H, m), 7.25-7.40(10H, m), 7.70-7.80(4H, m).

Formulation Example 1

In water for injection were dissolved 1.25 g of the compound obtained in Example 2 and 5.0 g of D-mannitol so as to provide a total amount of 100 ml. The solution was filtered through a 0.22-μm membrane filter, and 10 mL of the resultant drug solution was packed in an ampule and sealed, followed by steam sterilization to provide an injection.

Formulation Example 2

In water for injection were dissolved 1.02 g of the compound obtained in Example 10 and 31.5 g of sodium chloride so as to provide a total amount of 3.5 L. The solution was filtered through a 0.22-μm membrane filter, and 10 mL of the resultant drug solution was packed in an ampule and sealed, followed by steam sterilization to provide an injection.

Formulation Example 3

There were mixed 500 mg of the compound obtained in Example 1, 350 mg of lactose, 250 mg of corn starch, and 400 mg of crystalline cellulose (trade name: Ceolus PH101; Asahi Kasei Chemicals Corporation), to which 0.6 mL of a 5% hydroxypropylcellulose aqueous solution and water were then added before kneading. The resultant mixture was dried at 60° C., followed by adding 100 mg of crospovidone (trade name: Kollidon CL: BASF), 100 mg of light anhydrous silicic acid, and 20 mg of magnesium stearate before mixing. Into the form of a round tablet 8 mm in diameter was tableted 175 mg of the mixture to provide a tablet.

Formulation Example 4

There were mixed 500 mg of the compound obtained in Example 1, 200 mg of lactose, and 530 mg of corn starch, to which 0.6 mL of a 5% hydroxypropylcellulose aqueous solution and water were then added before kneading. The resultant mixture was dried at 60° C., followed by adding 70 mg of crosspovidone (trade name: Kollidon CL: BASF), 180 mg of crystalline cellulose (trade name: Ceolus PH302; Asahi Kasei Chemicals Corporation), and 20 mg of magnesium stearate before mixing. In a No. 3 gelatine capsule was packed 150 mg of the mixture to provide a capsule.

INDUSTRIAL APPLICABILITY

The compound of the present invention is useful as an excellent antifungal agent because it is highly active against fungi including those resistant to azole agents and has excellent physical properties as well as being highly safe in the repeated-dose toxicity tests, and also useful as an antiprotozoan because it has an excellent antiprotozoan activity.

Figure 1:
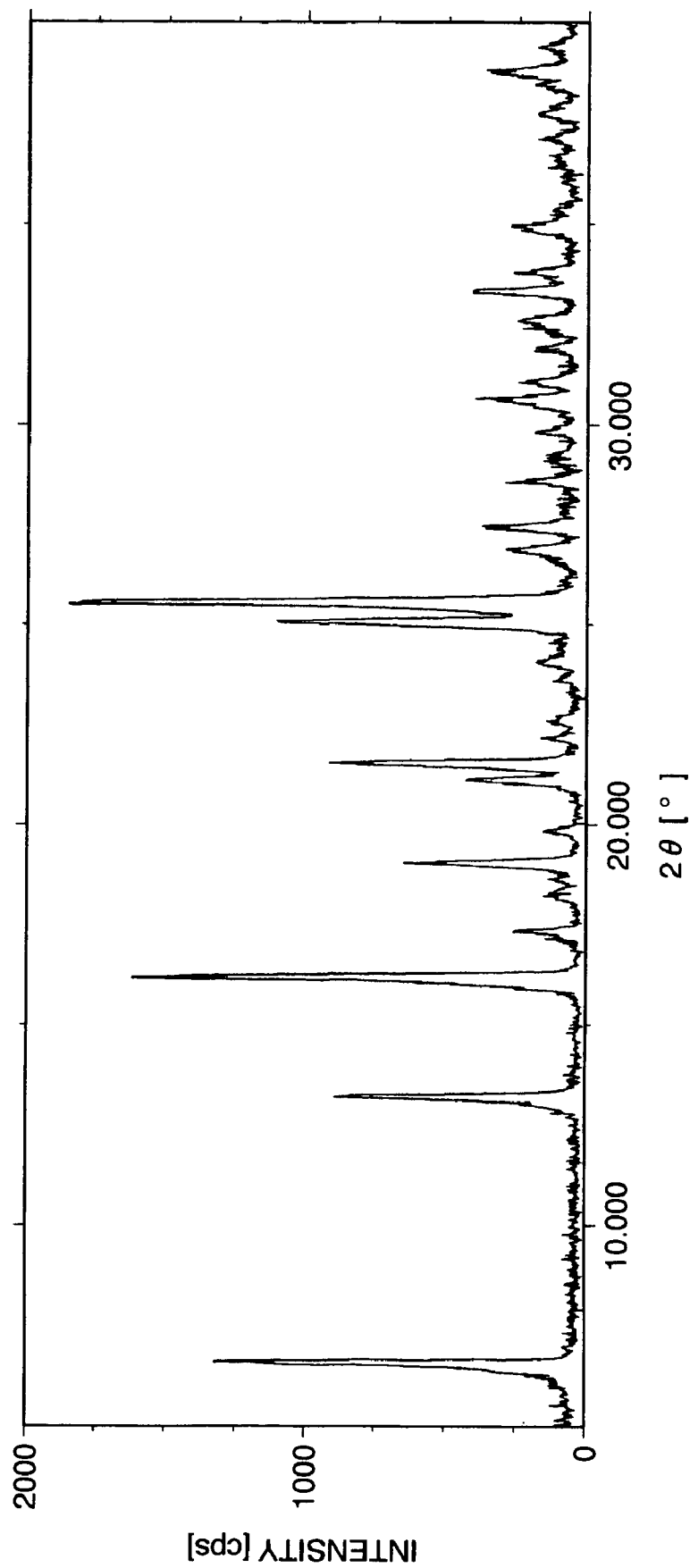
FIG. 1 is a powder X-ray diffraction pattern of 4-{3-[4-(3-{4-[amino(imino)methyl]phenoxy}propyl)-1-piperidinyl]propoxy}benzamidine trihydrochloride pentahydrate.

The invention claimed is:

1. 4-{3-[4-(3-{4-[amino(imino)methyl]phenoxy}-propyl)-1-piperidinyl]propoxy}benzamidine trihydrochloride pentahydrate.

2. An antifungal composition comprising 4-{3-[4-(3-{4-[amino(imino)methyl]phenoxy}propyl)-1-piperidinyl]propoxy}benzamidine trihydrochloride pentahydrate.

3. The antifungal composition according to claim 2, further comprising at least one of an excipient, a carrier, and a diluent.

* * * * *